United States Patent
Roan et al.

(10) Patent No.: US 11,413,388 B2
(45) Date of Patent: Aug. 16, 2022

(54) PORTABLE DEVICE WITH DISPOSABLE RESERVOIR FOR COLLECTION OF INTERNAL FLUID AFTER SURGERY FROM A PLURALITY OF SITES SIMULTANEOUSLY

(71) Applicant: Somavac Medical Solutions, Inc., Memphis, TN (US)

(72) Inventors: Esra Roan, Memphis, TN (US); Joshua D. Herwig, Memphis, TN (US)

(73) Assignee: Somavac Medical Solutions, Inc., Memphis, TN (US)

(*) Notice: Subject to any disclaimer, the term of this patent is extended or adjusted under 35 U.S.C. 154(b) by 4 days.

(21) Appl. No.: 16/550,214

(22) Filed: Aug. 24, 2019

(65) Prior Publication Data

US 2021/0052786 A1 Feb. 25, 2021

Related U.S. Application Data

(63) Continuation-in-part of application No. 15/604,254, filed on May 24, 2017, now Pat. No. 11,078,898.

(60) Provisional application No. 62/409,400, filed on Oct. 18, 2016, provisional application No. 62/340,853, filed on May 24, 2016.

(51) Int. Cl.
*A61M 1/00* (2006.01)
*A61M 39/24* (2006.01)

(52) U.S. Cl.
CPC ............ *A61M 1/631* (2021.05); *A61M 1/962* (2021.05); *A61M 39/24* (2013.01); *A61M 2205/273* (2013.01); *A61M 2205/3324* (2013.01); *A61M 2205/3389* (2013.01); *A61M 2205/3553* (2013.01); *A61M 2209/088* (2013.01)

(58) Field of Classification Search
CPC ...... A61M 1/631; A61M 1/962; A61M 39/24; A61M 1/0023; A61M 2205/3389; A61M 2209/088; A61M 2205/273; A61M 2205/84
See application file for complete search history.

(56) References Cited

U.S. PATENT DOCUMENTS 3,723,030 A * 3/1973 Gelfand .............. F04B 43/1292
417/475
5,041,096 A * 8/1991 Beuchat .................. A61M 1/80
604/118

(Continued)

*Primary Examiner* — Susan S Su
*Assistant Examiner* — Eric Rassavong
(74) *Attorney, Agent, or Firm* — Young Basile Hanlon & MacFarlane, P.C.

(57) ABSTRACT

A system, method, and apparatus for the collection of surgical/wound fluid from a subject patient with the capability of simultaneous fluid removal from a plurality of such wounds and/or wound through the utilization of a single pump device worn by such a patient. Such a system, method, and apparatus allow for such a single pump device to collect surgical/wound fluid within a single site collection component attached to or associated with such a single pump device. Multiple fluid transfer lines may be incorporated with the single pump device leading to such plurality of wounds and/or wound sites for greater versatility and comfort for the subject patient, as well as cleaner removal capabilities than in the standard apparatus systems and method currently undertaken within the industry.

20 Claims, 75 Drawing Sheets

(56) References Cited

U.S. PATENT DOCUMENTS

| | | | | |
|---|---|---|---|---|
| 5,064,358 A | * | 11/1991 | Calari | F04B 43/1253 |
| | | | | 417/475 |
| 5,460,490 A | * | 10/1995 | Carr | A61M 1/0058 |
| | | | | 417/44.2 |
| 7,670,323 B2 | * | 3/2010 | Hunt | A61M 27/00 |
| | | | | 604/320 |
| 9,907,901 B2 | * | 3/2018 | Orczy-Timko | A61M 3/0258 |
| 2010/0179493 A1 | * | 7/2010 | Heagle | A61M 1/784 |
| | | | | 604/313 |
| 2013/0131616 A1 | * | 5/2013 | Locke | A61M 1/0023 |
| | | | | 604/321 |

* cited by examiner

PORTABLE DEVICE WITH DISPOSABLE RESERVOIR FOR COLLECTION OF INTERNAL FLUID AFTER SURGERY FROM A PLURALITY OF SITES SIMULTANEOUSLY

CROSS-REFERENCE TO CORRELATED APPLICATIONS

This application is a continuation-in-part of co-pending U.S. Non-Provisional patent application Ser. No. 15/604,254, filed on May 24, 2017, which claims benefit of and priority to U.S. Provisional Applications Nos. 62/340,853, filed May 24, 2016, and 62/409,400, filed Oct. 18, 2016, and is entitled to priority to those filing dates. The entirety of the specifications, drawings, appendices, and complete disclosures of the parent application as well as the grandparent Provisional Applications Nos. 62/340,853 and 62/409,400 are incorporated herein by specific reference for all purposes.

FIELD OF THE DISCLOSURE

This invention relates to medical devices, particularly those used to drain serous or serosanguinous fluid from the percutaneous site after surgery.

BACKGROUND OF THE PRIOR ART

In order to drain the fluid which naturally builds up after surgeries such as mastectomies, abdominoplasties, panniculectomies, hernia repair, and the like, surgeons place drains attached to reservoirs which collect the bodily fluids for a period of time ranging from several days to several months. Once the bulbs are filled, the patient or an aide empties the contents into a measuring cup, measures and reports the amounts of collected fluid to the healthcare provider. The daily collected amount is the determinant of the clinical decision, i.e., the removal of the drains. Patients strongly dislike the drains due to quality of life issues, but yet it is their self-reported values that determine the clinical course. This conflict of interest jeopardizes the optimal care of the patient.

Despite prior attempts to reduce the risk of postoperative seromas due to large flap forming surgeries, no single technique has been shown to eliminate the risk completely. Current solutions are passive, tend to clog, are ineffective in removing fluid, are much disliked by patients and healthcare providers, and lack any diagnostic capability.

One of the major issues with post-surgical fluid management is the storage of the collected fluids. There are large amounts of fluid that is collected in patients who undergo large void-forming surgeries. This results in large volumes to be collected, measured, and emptied. The patients wear graduated bulbs in which fluid is collected and measured by patients themselves. Multiple issues relate to this: (1) fluid is collected only after all the air is removed from the abdomen; (2) patients have to pour the fluid in a measuring cup, measure, record, and report to their healthcare provider, (3) maintenance of sterility is difficult. In order to effectively remove the fluid in a continuous manner, air must be removed from the collection reservoir. Otherwise, either the reservoir is filled quickly with air/liquid mixture and emptying must take place to remove fluid often, or the reservoir overfills leading to high pressure levels and possibly backflow.

Devices which are designed to remove serous or serosanguinous fluid from the internal percutaneous space of a patient after surgery are cumbersome for patients to manage, and apply severely limited pressure to the internal space resulting in ineffective drainage and the development of blockages in the drainage lines.

Accordingly, there is a need for a device that that addresses these problems and issues with a comprehensive approach.

Additionally, there is lacking the ability to provide efficient and effective surgical (or wound) fluid removal from more than one site by a single device simultaneously within the prior art. There are instances where a patient undergoes a plurality of surgical procedures, or, alternatively, suffers multiple wounds during an accident, as examples, that require more than one active fluid removal actions at the same time. Whether in terms of a surface injury with a deep tissue wound at the same site or with a surface injury and a separate surface injury at different sites or deep tissue wounds at different sites or surface and deep tissue wounds at different sites, with, of course, the potential for more than two such injuries in whatever combination possible, there is no fluid removal device that provides a single point of fluid intake and thus removal from all such sites simultaneously. The closest type is of the potential for a surface incision having fluid removed therefrom with a deeper intake provided below the exact incision. In such a situation, the system utilized is specific to such a configuration and requires exactness as to the layout with the lower intake component just below the surface, not within a deep tissue position, and certainly not within the ability to provide such fluid removal at any other location other than strictly at the same surgical incision location. As such, again, there is no teaching that provides a single device capability for simultaneous surgical (or wound) fluid removal from multiple sites. To the contrary, then, a further development provides such a beneficial and effective method and system.

SUMMARY OF THE DISCLOSURE

In various exemplary embodiments, the present disclosure comprises a system and apparatus for the collection of serous or serosanguinous fluid from the percutaneous site after surgery. There are large amounts of fluid that collect in patients who undergo large void-forming surgeries. This results in large volumes to be collected, measured, and emptied. In order to effectively remove the fluid in a continuous manner, air must be removed from the collection reservoir. Otherwise, either the reservoir is filled quickly with air/liquid mixture and emptying must take place to remove fluid often, or the reservoir overfills leading to high pressure levels and possibly backflow.

In several embodiments, the present invention makes use of a powered source of negative pressure which helps overcome clogging observed in prior art devices, and one or more reservoirs which allow excess air to be removed. The invention comprises disposable reservoirs with one-way valves that are easy to handle while maintaining sterility and a seal to prevent the loss of vacuum. The present invention further provides continuous negative pressure suction which assists in providing constant drainage. Prior art devices do not provide a means of applying continuous negative pressure to the percutaneous wound site.

In addition, the measurements of the output can be performed automatically, relieving the need for the patient to perform measurements directly (and thus resolving the potential conflict of interest in self-measuring so that the best clinical decisions can be made). The measurements of output can be relayed to the caregiver, doctor, or the nurse via wired or wireless communications, and enables patients who do not have companions to manage their drain care. There is a potential diagnostic value in taking various measurements associated with the collected fluid. Measurements can include and are not limited to collected fluid amount, pH, certain known harmful mediators (cytokines, chemokines, reactive oxygen species), protein levels, blood content, etc. For example, amount of fluid collected can be an indicator of possible seroma development in some hernia surgeries. Additionally, pH has also been shown to act as an indicator of possible seroma formation. The present invention thus allows for the detection of infectious materials, and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds.

The ability to provide simultaneous removal from different surgical and/or wound sites with the same vacuum device creates significant efficiencies, particularly through the avoidance of "grenades" at multiple sites. In other words, the standard "grenade" type surgical fluid removal devices required a plurality at each site to ensure any degree of fluid transfer. The ability to utilize a single vacuum device with multiple reliable suction lines thus allows for a much cleaner, far less cumbersome, and superiorly effective manner of providing safer conditions for subject patients to heal.

As noted herein, any standard type of vacuum device may be utilized to perform such multiple location fluid removal actions simultaneously; however, it has been found and realized that peristaltic pumps provide certain benefits that allow for greater reliability and, overall, safer results. In particular, the ability for such peristaltic pumps to stop quickly, but further to reverse easily and without any appreciable, let alone potential, harm to the motor(s) therein, provides significant improvements over standard air pumps (and other like types). For instance, regardless of the type of device utilized for such fluid removal, a vacuum is applied, thereby leaving the system susceptible to potential problems due to clogging of the fluid removal line. Alternatively, such a device has no indicator available providing the user (or health care provider, for that matter) if the total amount of fluid present at the surgical/wound site has been truly transferred external of the subject patient. Thus, the system may suffer from a situation wherein the device continues to apply suction and such an action results in a back up due to either of a clog or the lack of any further fluid to be removed. A typical vacuum device (air pump, grenade type, for instance) has no way to determine what problem may be encountered, leaving the user or provider with removing the line from the patient to check for a clog empirically. If no clog is present, it may be surmised that the device has completed the desired fluid removal from the target site. To the contrary, however, is the ability to determine any such problem (clog or finished removal) without having to remove (and thus deal with a cumbersome if not "messy" situation) the vacuum line from the patient. The inclusion of appropriately situated sensors within the target line combined with the ability to reverse a peristaltic pump without harming the device and/or system, overcomes any such issues. For example, with a sensor located at the line's end within the patient (e.g., adjacent the fluid ingress point within the line itself), if the device exhibits a vacuum lock (due to a clog or completed fluid removal), the user or provider may simply stop the peristaltic pump and reverse for a short period (1-2 seconds, for instance). With the sensor in place, if a clog is present, the sensor will either indicate the movement of the clog back out of the line, or no movement at all of fluid or anything else, essentially denoting the clog is rather strong and thus requires manual removal. If the fluid removal has finished, the reversal will force any fluid within the line back within the patient through the line, particularly without any push back force (due to a clog, for example). Thus, such a peristaltic pump device allows for such a determination. If the fluid removal has completed, the line can then be removed without any excess fluid flowing therefrom as it is being taken from the subject patient. If a clog is present, either the reverse direction of the pump will dislodge it or the user/provider will know it is serious enough to require manual removal, thereby allowing for preparation of such a line removal, as well. In any event, such a peristaltic pump device allows for such simplified manners of system monitoring, combined with the cleaner and less cumbersome practice related thereto, particularly as compared with "grenade" type fluid removal devices. Again, although standard air (or even hydraulic, etc.) pumps may be utilized for the multiple location removal systems disclosed herein for simultaneously fluid removal from a plurality of surgical/wound sites, the peristaltic pump device(s) further disclosed herein are potentially preferred, particularly in view of the beneficial reversible pressure applications (on the fly, for that matter) for improved operations (e.g., again, determine clog, system finishing, etc.), and thus overall greater reliability and, ostensibly, cleaner operations, as well.

The utilization of a single vacuum device with multiple vacuum assemblies allows, again, for the placement of a single unit for such a purpose, thereby permitting a user (patient) the potential for a more comfortable placement of such a device as worn during fluid removal operations. The multiple vacuum assemblies thus further accord the ability to access a plurality of different surgical wound (or other like) sites on a single patient for simultaneous draining capabilities. As noted throughout, such sites may be deep wounds (such as well below the cutaneous and possibly subcutaneous layers thereof) as well as surface wounds (such as within cutaneous and possibly subcutaneous layers). The utilization of two vacuum assemblies within the same device simultaneously (with attached fluid removal lines leading through the device to collection chambers) thus may allow for access to fluid within a deep wound and a surface wound, two deep wounds, or two surface wounds, again, simultaneously. Additionally, however, due to the vacuum strength involved, the user (patient) may be configured with even more fluid removal lines attached to two vacuum assemblies within the same device (and leading to at least one, potentially more, collection chambers, particularly within or attached the same vacuum device) for access to even more wound sites. For instance, a first fluid removal line leading from a vacuum component (pump) may lead to a splitter device that includes two or more separate fluid removal lines leading therefrom to two or more wound sites. A second fluid removal line leading from the same device, but the other vacuum component (pump) may also lead to a separate splitter device that includes another st of separate fluid removal lines in the same manner Thus, instead of just two wound sites involved for fluid removal simultaneously, the number may be doubled, even tripled, or even higher, on demand Such a splitter device may thus be completely open in terms of continuous vacuum pressure application for fluid removal from each accessed wound site, or such may be controlled through, for example, a stopcock, or like device, that may allow for one line to remain open while one or more of the others is closed, permitting selected fluid removal (for instance, if one wound site is of a larger type generating a greater amount of fluid, or, perhaps, as another non-limiting alternative, the user, or health care professional aiding with such an activity, desires to access one or more wound sites for fluid removal for analytical reasons for a certain time period). In any event, such an overall capability allows for selective or, at least, continuous access for fluid removal purposes with a single vacuum device. It should be evident, as well, that even if the vacuum device has two separate vacuum components (pumps) such a plurality wound site access potential may be achieved through the utilization of only one such pump with a single fluid removal line leading to a splitter for multi-fluid removal line access purposes, as alluded to above. Thus, the system(s) and method(s) disclosed herein permit significant versatility with a single worn vacuum device, providing the user (patient) and, for the most part, the health care field, a noticeable improvement in terms of comfort, cleanliness, and overall efficiency as it concerns effective and desirable surgical and/or wound fluid removal.

The plurality of sites for fluid removal with a single device and/or system, as well as the beneficial operations due to safe reversible vacuum application on demand, are discussed in greater detail below.

DETAILED DESCRIPTION OF EXEMPLARY EMBODIMENTS

In various exemplary embodiments, the present invention comprises a system and apparatus for the collection of serous or serosanguinous fluid from the percutaneous site after surgery. There are large amounts of fluid that collect in patients who undergo large void-forming surgeries. This results in large volumes to be collected, measured, and emptied. In order to effectively remove the fluid in a continuous manner, air must be removed from the collection reservoir. Otherwise, either the reservoir is filled quickly with air/liquid mixture and emptying must take place to remove fluid often, or the reservoir overfills leading to high pressure levels and possibly backflow.

In several embodiments, the present invention makes use of a powered source of negative pressure which helps overcome clogging observed in prior art devices, and one or more reservoirs which allow excess air to be removed. The invention comprises disposable reservoirs with one-way valves that are easy to handle while maintaining sterility and a seal to prevent the loss of vacuum. The present invention further provides continuous negative pressure suction which assists in providing constant drainage. Prior art devices do not provide a means of applying continuous negative pressure to the percutaneous wound site.

In addition, the measurements of the output can be performed automatically, relieving the need for the patient to perform measurements directly (and thus resolving the potential conflict of interest in self-measuring so that the best clinical decisions can be made). The measurements of output can be relayed to the caregiver, doctor, or the nurse via wired or wireless communications, and enables patients who do not have companions to manage their drain care. There is a potential diagnostic value in taking various measurements associated with the collected fluid. Measurements can include and are not limited to collected fluid amount, pH, certain known harmful mediators (cytokines, chemokines, reactive oxygen species), protein levels, blood content, etc. For example, amount of fluid collected can be an indicator of possible seroma development in some hernia surgeries. Additionally, pH has also been shown to act as an indicator of possible seroma formation. The present invention thus allows for the detection of infectious materials, and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds.

Figure 1:
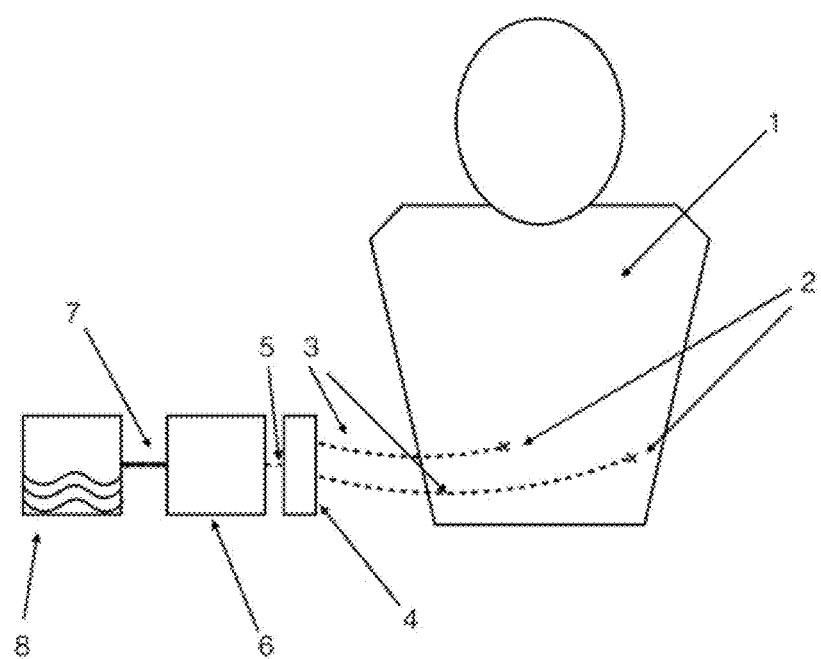
FIG. 1 is a perspective view of an exemplary embodiment of the device and patient.

FIG. 1 shows an exemplary embodiment of the present system. Drainage structures 3 begin in the percutaneous space, extend through the percutaneous tissue at an exit site 2 and terminate in the multiple-drainage-structure manifold 4. A pump 6 creates a negative pressure in the connection 5 between the pump 6 and manifold 4 and imparts a negative pressure to the single or multiple drainage structures 3. The pump 6, by employing either a peristaltic mechanism, positive displacement, or some other source conveys positive pressure to the collected fluid after it enters the pump unit, which causes the fluid to be transported to the disposable reservoir 8. A series of one way valves which may be placed at either one or all of the following locations ensure the prevention of backflow: at the manifold entrance, pump entrance and exit, and reservoir entrance.

The pump 6 is controlled by means of an onboard processor which may take as inputs from the user the following: on/off; desired pump pressure; and device communication parameters (i.e., mobile device connectivity and the selection of default mobile device). Additionally, the onboard processor may take as inputs from the device the following: pump pressure differential (between exit 2 and pump entrance); flow rate at manifold (for each individual drainage structure or for all drainage structures combined); motor current draw; device orientation with respect to force of gravity (from accelerometer); presence of bacterial or pathogenic substances; immune system indicators; battery charge level; or any value relevant to the operation of the device.

The device may communicate via Bluetooth or some other communication protocol (e.g., BLE, NFC) to a mobile device or to a larger cellular network in order to provide information regarding the performance of the device (e.g., battery charge level, need to change reservoir, device temperature, current magnitude of negative pressure, presence of blockage in tubing, or any other relevant information which may be of benefit to either the patient, their nurse, their doctor, their caregivers, their family, or any interested party) and the characteristics of the collected fluids. These characteristics may include, but are not limited to, the following: total collected amount (either total or per drainage structure); rate of fluid collection (total or per drainage structure) over one or more time scales (e.g., hours, days, or weeks); presence of infectious materials; and the presence of any other chemicals or substances which may indicate infection or the presence of some medical condition which may naturally arise in response to the surgical procedure, initial pathology, or additional complications (of either the surgical procedure or the initial pathology) in the fluid collected from percutaneous (internal) wounds. This information may be relayed to a mobile computing device, personal computer, or any computer or database system which may be accessed by the staff of an inpatient or outpatient medical center, the patient, their nurse, their doctor, their caregivers, their family, or any interested party as allowed by law. This information may be accessed by a purposefully designed mobile application on the mobile computing devices of the patient, their nurse, their doctor, their caregivers, their family, or any interested party as allowed by law.

Figure 2:
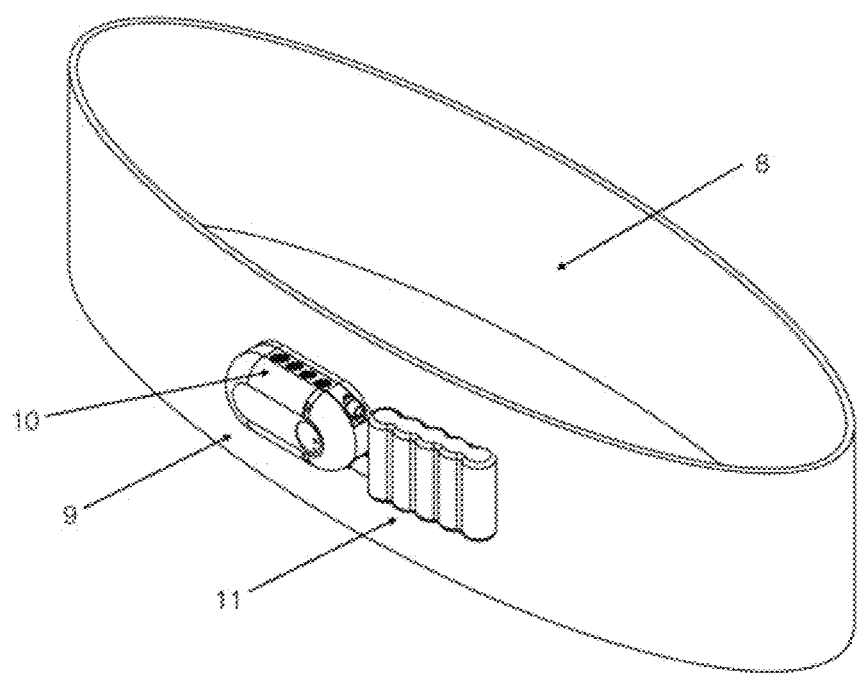
FIG. 2 is a perspective view of one embodiment of the device incorporated into an abdominal binder.

FIG. 2 shows a perspective view of a pump 9, manifold 10, and disposable reservoir 11 placed onto an abdominal binder 8. This arrangement comprises a single unit generally placed at the end of the surgical procedure. The device components may connect to the binder by means of a removable fastening system so that it may be removed from the binder to facilitate patient comfort. Additionally, the binder may incorporate some means to secure the drainage structure (drainage tubing) at the surgical exit site, and along its path to the pump unit. Furthermore the binder may fasten to itself (forming a continuous loop) by means of hook-and-loop fabric connection, buckle connector, or button snap connector(s). The location at which the pump unit attaches to the abdominal binder may incorporate some means of heat mitigation, such as, but not limited to, an open-cell foam pad, or gel-filled plastic pouch type pad.

Figure 3:
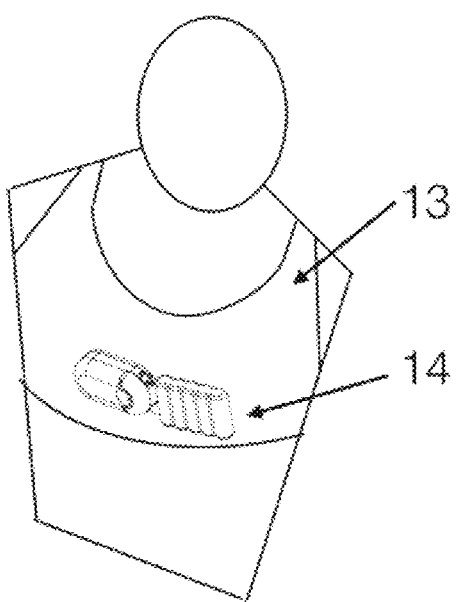
FIG. 3 is a perspective view of one embodiment of the device incorporated into a bra for use after mastectomy.

In an alternative embodiment, FIG. 3 shows a perspective view of a combined pump, manifold, and disposable reservoir unit 14 placed on a bra 13 or mastectomy binder, which is commonly used following a mastectomy procedure. This allows a single unit which is generally to be placed at the end of the surgical procedure. The device 14 may connect or be attached to the bra 13 by means of a removable fastener (as described above) so that it may be removed from the binder to facilitate patient comfort. Additionally, the bra may incorporate some means to secure the drainage structure (drainage tubing) at the surgical exit site, and along its path to the pump unit.

Figure 4A:
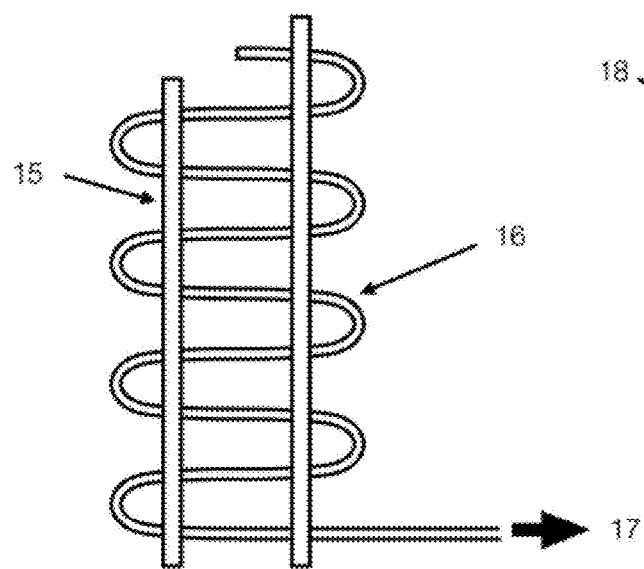
FIGS. 4A-B are views of exemplary embodiments of drainage structures which may be connected to the source of negative pressure.
Figure 4B:
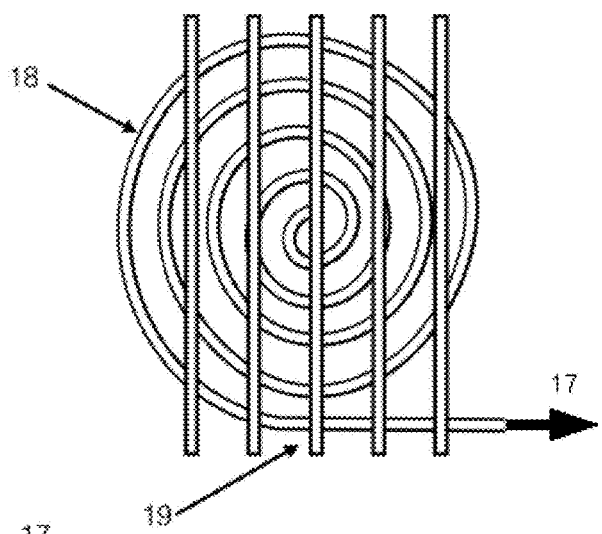

FIGS. 4A-B shows views of possible internal drainage structures placed inside of the percutaneous space at the time of surgery. A hollow flexible tube 16, 18 may be perforated, or may incorporate some cross section which facilitates the drainage of fluid and prevents tissue ingrowth into the tubing. Scaffolding 15, 19 holds the drainage structure in the conformation which increases surface area. The scaffolding units may be biodegradable or resorbable, and may incorporate different geometry, number, or conformation than shown in the figures. Additionally, these scaffolding units may incorporate antibacterial substances, or any substance which may aid in the tissue apposition of the wound space, healing, infection prevention, blood clot formation, or any other medically useful property. The scaffolding may adhere to the surface of the drainage tubing, or may incorporate such geometry as is necessary to allow the scaffolding to completely encapsulate the drainage tubing at the points of intersection. The drainage structure continues 17 through the percutaneous tissue through the exit site and terminates at the fluid collection unit or drainage bulb. While the drainage structures shown in FIGS. 4A-B are embodiments of the unique drainage structure, many other possible configurations are possible which utilize resorbable or biodegradable scaffolds to form the geometry of the drainage suture.

Figure 5:
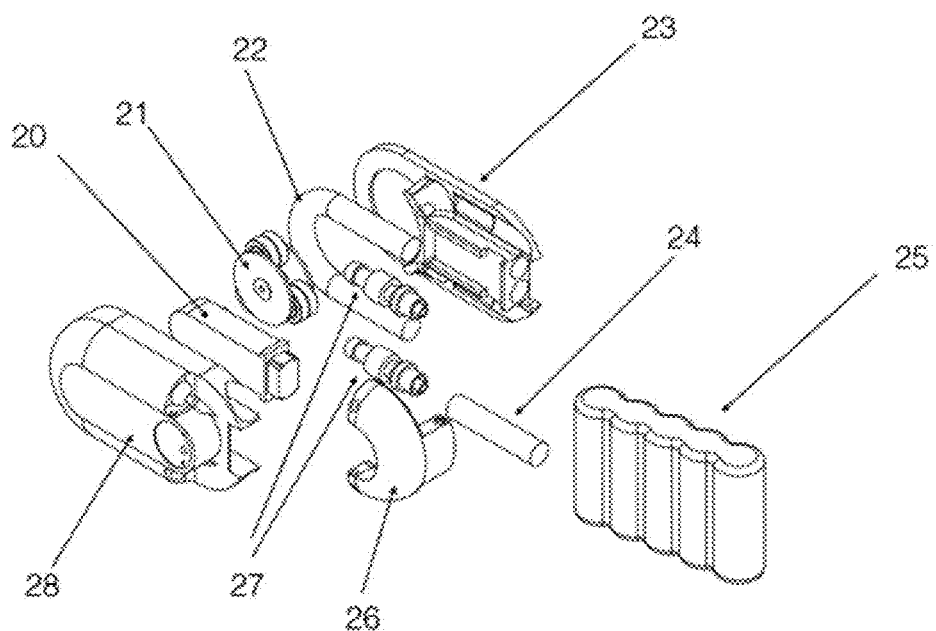
FIG. 5 is a perspective view of one embodiment of the pump device.

FIG. 5 shows a perspective view of one embodiment of the pump mechanism. The top housing (front 28 and rear 23) provides the main structural support for the device, and may also provide the contact path necessary for the peristaltic action or positive displacement to occur. Furthermore, it may house all necessary electronic components which include, but are not limited to, the microprocessor/microcontroller, the battery charging components, the user interface components (buttons, switches, displays), the communication components and circuitry, and all necessary wiring and small components. The peristaltic action is accomplished by the central rolling mechanism 21 sequentially compressing the internal tubing 22 which may consist of silicone rubber or any similar flexible material which may have desirable properties for this application. The driving force needed to rotate the central rolling mechanism is provided by an electric motor 20 which may be powered by either a rechargeable or a non-rechargeable battery source. In one embodiment, the motor is a 6V DC motor with a 90 degree output shaft in order to reduce the overall device profile. The majority of the electrical components are contained within the rear device housing 23. This also provides some storage space for batteries.

Sterile, one-way valves 27 prevent backflow of the fluid at both the pump entrance, and also at the pump exit (reservoir entrance). Fluid is transferred from the pump to the reservoir 25 through either direct connection or via additional tubing 24 to allow the reservoir to be placed at a distance away from the pump. The reservoir may be either soft flexible plastic or a hard, rigid container, or a combination of both in which a flexible plastic pouch is placed within a rigid outer container. As the reservoir 24 is placed downstream from the pump unit, it must provide for the release of excess air which may otherwise become trapped in the reservoir. Air-permeable, liquid-impermeable membranes may be incorporated into the reservoir in order to allow this air to escape. Furthermore the entire reservoir may be comprised of an air-permeable, liquid-impermeable material.

The pump unit may have features which allows it to be easily attached to an abdominal binder, mastectomy binder, or other means of securing the device to the patient. Additionally, an insulator (not illustrated) may be attached to the external surface of the rear device housing 23 to protect the patient/user from any excess heat generated by the device itself during operation. In a further exemplary embodiment, a sound insulator/reduction component or structure to reduce the sound waves generated by the unit may also be attached to the external surface of the rear device housing. The sound insulator/reduction component may reduce both actual sound volume as well as amplitude thereof, in order to provide a more comfortable situation for the patient/user.

Figure 6:
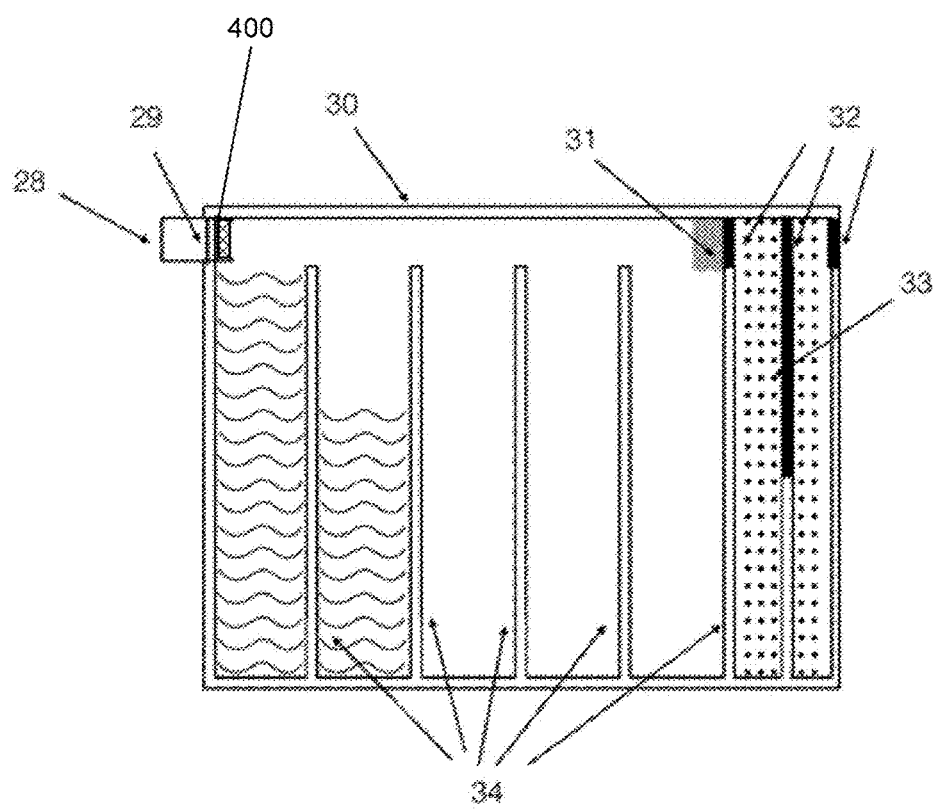
FIG. 6 is a perspective view of one embodiment of the fluid reservoir.

FIG. 6 shows a cutaway view of an embodiment of the reservoir. The reservoir is compartmentalized by segmenting structures 34 (in the case of a rigid reservoir) or by the heat-sealed or pressed structure (in the case of a flexible pouch-like reservoir). These segmenting structures prevent the splashing or excessive or irregular movement of fluid 200 in the reservoir, and provide a sequential filling order of the reservoir to limit the amount of fluid present in the final segment, in which gas-permeable, liquid-impermeable membranes 32 allow the escape of air. Fluid 200 is transferred from the pump unit into the reservoir through a quick-release connection 28. A one-way valve 29 prevents the backflow of fluid when disconnecting the reservoir from the pump unit. A significant distinction between this reservoir and prior art devices is that the reservoir of the present invention is designed to be disposed of and replaced by a new, clean reservoir each time the fluid fills a reservoir. This significantly improves the patient experience in that they no longer must empty the drain reservoir and replace it.

At the end of the reservoir furthest from the intake connection 28 is a chamber which may contain some compound 33, such as activated carbon, which both hinders the flow of fluid should it gain entry to the chamber, but also removes any odor from the air which is to be released from the reservoir. A mesh (foam or otherwise) filter 31 prevents excess fluid from backing up against the first gas-permeable, liquid-impermeable membrane 32. The end segment is constructed in such a way as to maximize gas release, and minimize the leakage of fluid. In the embodiment shown, three sequential membranes 32 are utilized in order to prevent the escape of fluid from the reservoir.

Additionally, the reservoir may make use of an onboard system (electronic or otherwise) for measuring certain characteristics of the collected fluid. These characteristics may include, but are not limited to, the following: total collected amount; rate of fluid collection on the time scales of hours, days, or weeks; presence of infectious materials; and any other chemicals or substances which may indicate infection; or the presence of some medical condition which may naturally arise in response to the surgical procedure, initial pathology, or additional complications (of either the surgical procedure or the initial pathology) in the fluid collected from percutaneous (internal) wounds.

For example, in one embodiment the reservoir may make use of a fluorescent-based assay for detecting the presence of bacteria, by using a photosensitive sensor to detect the light emitted by excitation of the fluorescent compound in the presence of bacteria. The reservoir may also make use of external graduation markings in combination with a transparent material to allow easy monitoring of fluid collection. Furthermore, in the case of a flexible reservoir design, the reservoir may comprise an internal pouch and an external rigid structure. As the pouch expands and reaches its maximum fill level, it may actuate a limit switch or proximity switch indicating the reservoir is nearing total capacity.

Figure 7:
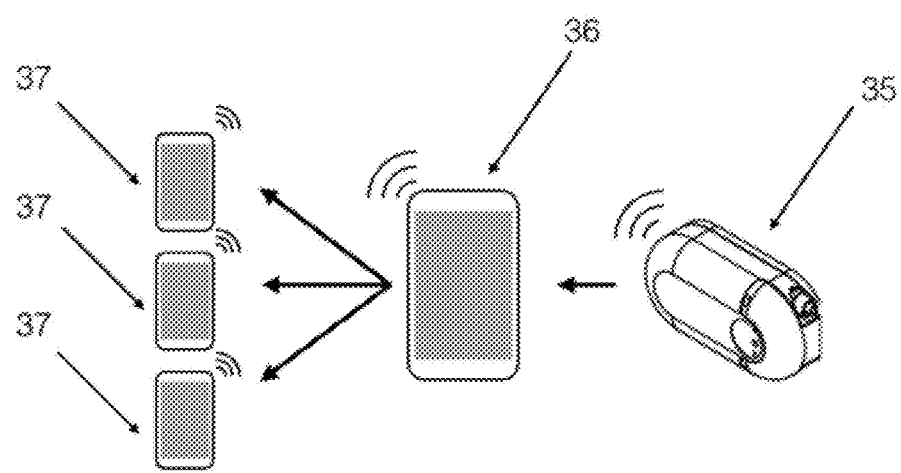
FIG. 7 is a schematic of one embodiment of the device communication features.

FIG. 7 shows a schematic of one embodiment of a communication channel between the pump device 35 and the devices 35, 36 of the staff of an inpatient or outpatient medical center, the patient, their nurse, their doctor, their caregivers, their family, or any interested party as allowed by law. This communication is designed to relay information regarding the function of the device, or the characteristics of the collected fluid, as described previously. The pump device 35 communicates wirelessly with the patient's mobile device 36, tablet computer, or personal computer by either device-to-device communication or by utilizing a local wireless local area network or a cell network. The information received by the patient's device is then relayed in a like fashion (device-to-device, wireless local area network, cell network) to the mobile devices 37, tablet computers, or personal computers of the staff of an inpatient or outpatient medical center, the patient's nurse, their doctor, their caregivers, their family, or any interested party as allowed by law. Any of these devices, or the pump device itself, may make treatment recommendations or diagnoses based on the information gained from the collected fluid.

Figure 8:
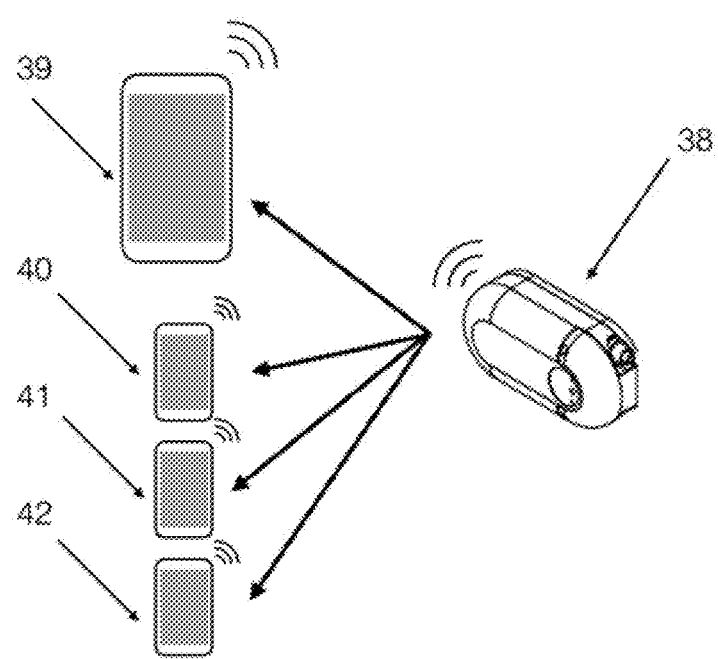
FIG. 8 is a schematic of a different embodiment of the device communication features.

FIG. 8 shows another embodiment of a communication channel between the pump device 38 and the devices 39, 40, 41, 42 of the staff of an inpatient or outpatient medical center, the patient, their nurse, their doctor, their caregivers, their family, or any interested party as allowed by law. This communication is designed to relay information regarding the function of the device, or the characteristics of the collected fluid as described previously. The pump device 38 communicates wirelessly with the mobile devices, tablet computers, or personal computers of the staff of an inpatient or outpatient medical center, the patient 39, the patient's nurse, their doctor, their caregivers, their family, or any interested party as allowed by law 40, 41, 42. Any of these devices, or the pump device itself may make treatment recommendations or diagnoses based on the information gained from the collected fluid.

Figure 9:
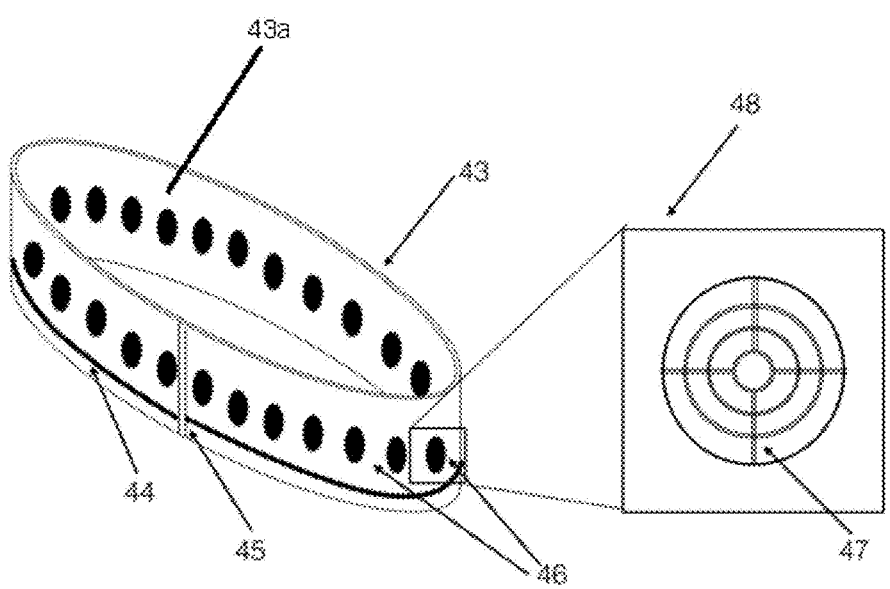
FIG. 9 is a perspective view of one embodiment of a device used to fasten the device to the patient (e.g., abdominal binder, mastectomy bra, and the like).

FIG. 9 is a perspective view of an exemplary embodiment of an apparatus 43 which may function as an abdominal binder, mastectomy bra, or any other means of attaching the pump device and reservoir to the patient. The apparatus 43 is constructed from fabric or other suitable material, and is backed with a padding or other material 43a which increases the comfort to the patient, such as, but not limited to, foam or gel padding. A series of ports 46 which allow the drainage tubing to pass through the apparatus are provided at various locations around the apparatus, and may be present in a repeating pattern or spacing. The apparatus may incorporate a greater or lesser number of these ports than shown in FIG. 9.

A tubing channel 44 is provided in the apparatus to allow convenient routing of the drainage tubing. This channel may secure the tubing by means of folding a section hook-and-loop fastener fabric over the tubing along the length of device or portions thereof. The channel also may comprise several snap-fit clamps along the length of the apparatus.

A magnified view 48 of the pass-through ports 46 shows in detail the construction of the port. The port comprises a foam portion which has been pre-punched or pre-cut 47 in such a way as to allow easy removal of the section of foam which has a diameter close to the diameter of the desired drainage tubing. By incorporating this feature, surgeons may make use of any diameter drainage tubing, or may utilize several different sizes of tubing at different locations.

A fastening feature 45 allows the apparatus to be removed easily. The feature may function by means of hook-and-loop fabric, button snaps, buckle fasteners, or clasps. The apparatus may also include some feature for mounting the pump and reservoir, or any other desired peripheral devices. This feature will match a corresponding feature on the pump and reservoir to allow quick and easy removal, in a manner similar to that described above. The device also may feature some other means of securing the drainage tubing.

Figure 10:
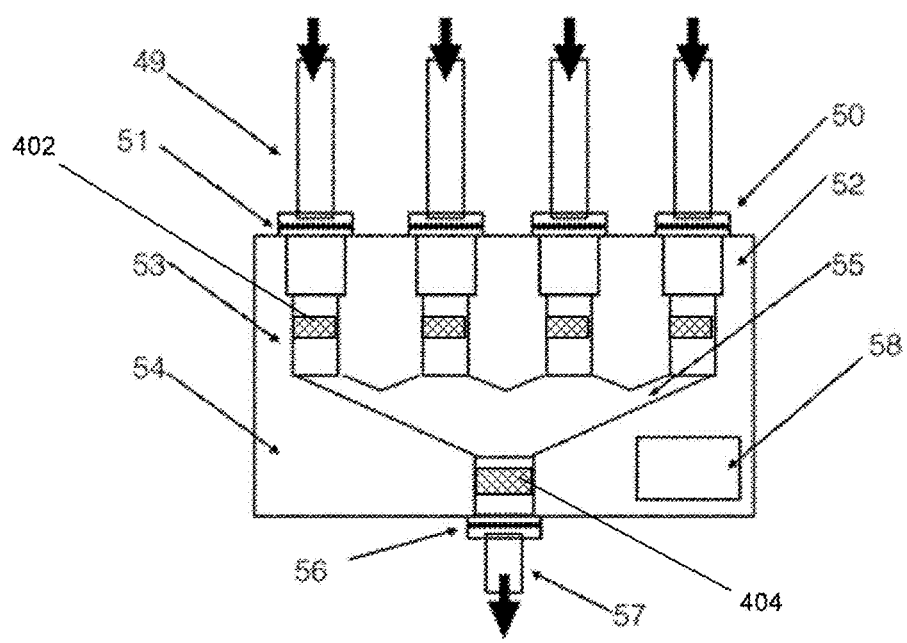
FIG. 10 is a cutaway view of one embodiment of the multiple tubing input manifold.

FIG. 10 is a cutaway view of one embodiment of the manifold at the pump entrance. This manifold allows the connection of one or many drainage inputs. In this embodiment, four input connections are shown; however the manifold may comprise fewer inputs or greater inputs. Each drainage tubing line 49 is secured to the manifold by a connector 50 (which may be a barbed fitting and quick-disconnect combination). This connector 50 may allow for the input of many different sizes of drainage tubing via adaptor fittings or through inherent design. Downstream of the connector is a one-way valve 51 which prevents backflow of the fluid.

Within the body 54 of the manifold are channels 52 which accept the fluid after the one-way valve 51. These channels 52 direct the fluid into separate measurement units 53 which collect information about the characteristics of the collected fluid. These characteristics may include, but are not limited to, the following: total collected amount; rate of fluid collection on the time scales of hours, days, or weeks; presence of infectious materials; and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds. This information may then be relayed to an onboard processor 58 for additional processing before being forwarded on to the processor in the pump device. A collection unit 55 channels all fluid into single channel. The manifold may include another one-way valve 56 at the exit 57 which may make use of a quick-disconnect connector or may transfer the fluid directly the pump unit. In this embodiment, the manifold, itself, does not possess any means of moving the collected fluid but rather relies on the action of the downstream pump device. The manifold may be separable from the pump device or may be a continuous molded unit with the body of the pump device.

Figure 11:
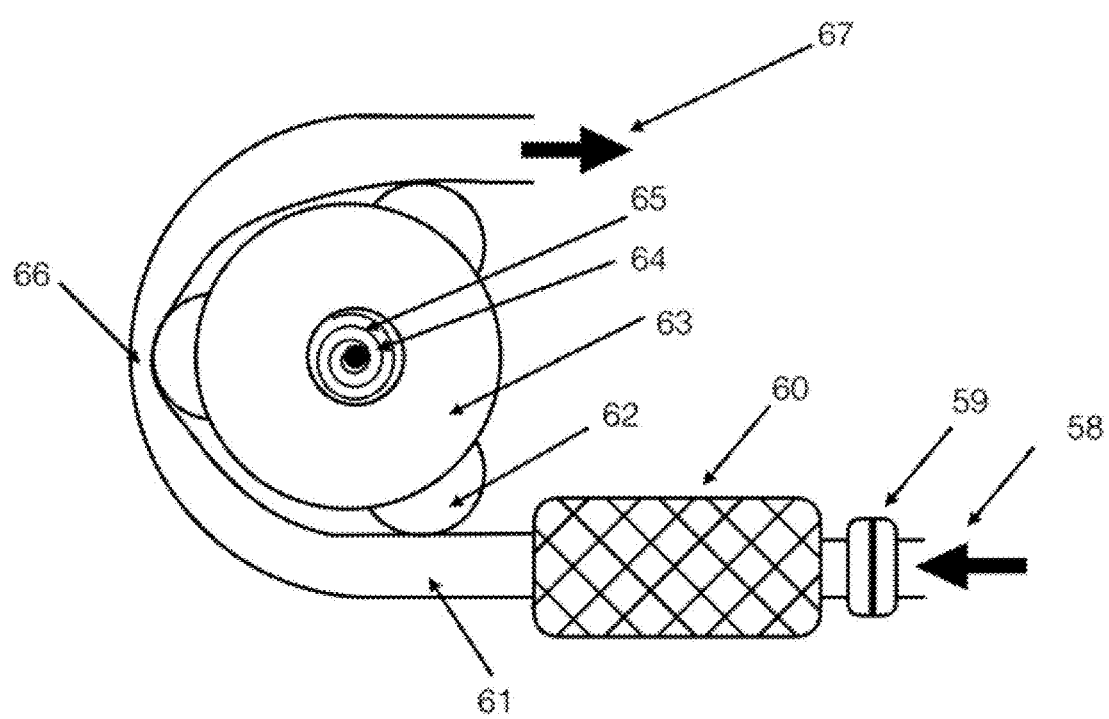
FIG. 11 is a view of one embodiment of a mechanism to prevent excess pressure for building up against the outlet one-way valve.

FIG. 11 shows an overview of a unique mechanism within the peristaltic pump device which prevents a high pressure in the system downstream from the central rolling unit 63. This is useful particularly when the reservoir is removed from its connection to the upstream collected fluid. A one-way valve or valves may be positioned both before and after the reservoir connection, and the upstream valve likely will have some residual pressure against it which may cause an amount of fluid to leak when the reservoir is disconnected. This mechanism allows the central rolling unit to automatically reverse, i.e., turn in a direction opposite the direction it must turn to normally pump the fluid. This is achieved via a spring 65 at the attachment between the motor output shaft 64 and the body of the central rolling unit 63. When the motor is stopped the spring naturally unwinds or uncoils, causing the central rolling unit to turn with it some amount. This causes the point at which the rollers contact the tubing 66 to shift, causing the fluid to be pushed backwards opposite its normal flow direction. A section of compliant tubing 60 allows the influx of excess fluid without causing a higher than optimal pressure to develop in the tubing. A one-way valve 59 prevents the fluid from back flowing through the pump entrance 58. The arrows 58 and 67 show the normal direction of fluid transport. The direction of fluid transport caused by this mechanism (when the motor is stopped) is opposite the direction denoted by the arrows. Not shown is the pump housing, which holds all components and allows the peristaltic action of the pump.

Figure 12:
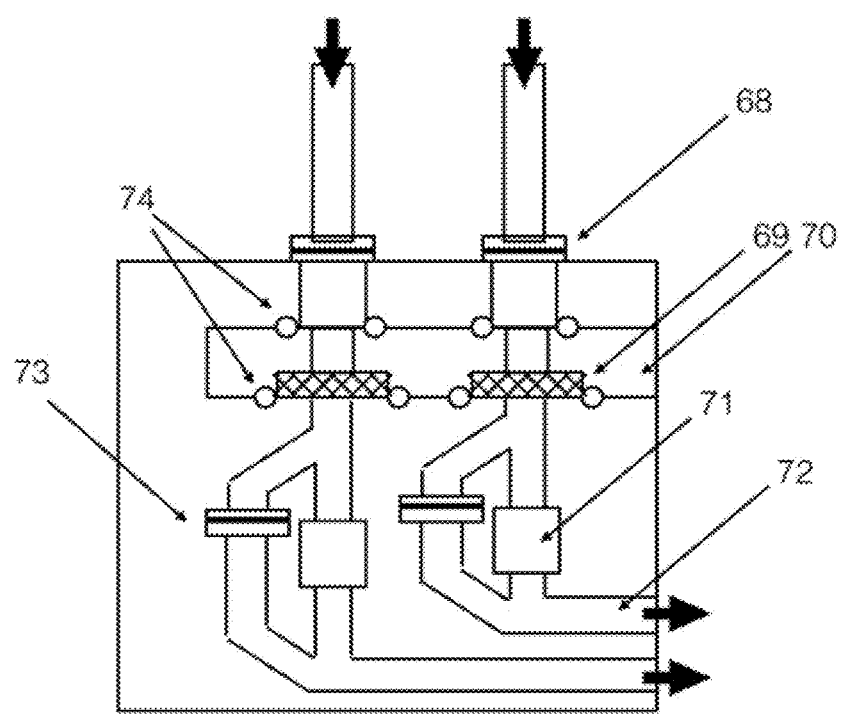
FIG. 12 is a view of one embodiment of a mechanism to allow the preservation of the "stripping" or "milking procedure", and also allows for the collection of large materials which may be problematic for the pumps in the device.

FIG. 12 is an overview of one embodiment of a mechanism to allow the preservation of a "stripping" or "milking procedure", and also allow for the collection of large materials, which can cause problems in the pump(s). The "milking" or "stripping" procedure is currently prescribed as a method to clear blockage in the drainage structure, and calls for the user to apply pressure using their fingers to the tubing above the blockage and, in a peristaltic nature, moving their fingers down the tubing past the blockage, promoting a restored flow. As several exemplary embodiments of the present utilize a peristaltic pump, which occludes flow if stopped, some mechanism is needed to accommodate the "stripping" or "milking" procedure. This mechanism consists of one or more one-way valves 68 (generally one per drainage connection) immediately after the connection to the drainage structure, which prevents backflow of fluid or particles into the tubing Immediately downstream of the one-way valve is a chamber (or chambers) 70 to receive fluid and particles, the latter of which may potentially block downstream components in the device and inhibit flow. At the exit of this chamber is a filter or screen 69, which prevents larger particles from moving further downstream. This entire chamber may be removable, in which case seals 74 are incorporated to prevent fluid leakage by occluding the gap necessary to facilitate removal of the chamber. Downstream of this chamber, the tubing bifurcates with one channel facilitating fluid transport to the pump(s) 71 and a second "bypass" channel facilitating fluid transport around the pump when the "milking" or "stripping" procedure is performed. A one-way valve 73 is placed in the second channel to prevent backflow of fluid during normal pump operations. The valve remains closed, and the bypass channel thus is shut-off to fluid flow during normal operations. The two tubing channels converge to a single channel downstream from the pump and one-way valve, facilitating fluid transport to the remainder of the device 72 or to the output reservoir.

Figure 13:
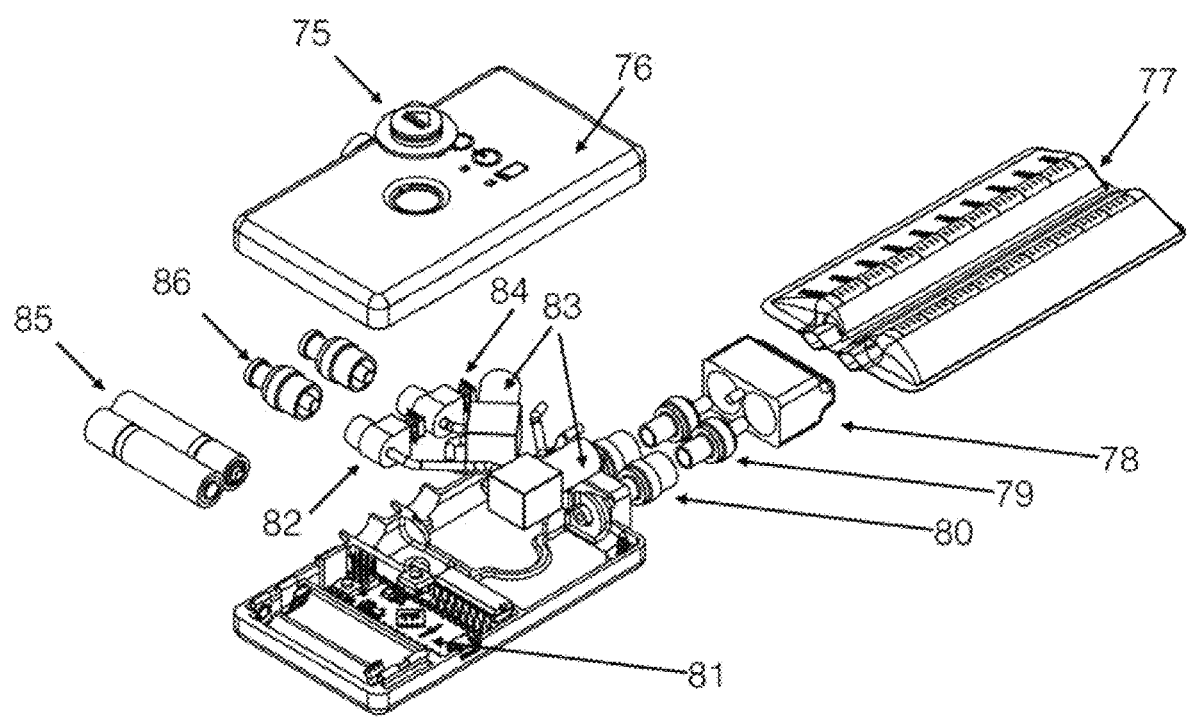
FIG. 13 is an exploded view of one embodiment of the device described in this document.

FIG. 13 is an exploded view of an exemplary embodiment of an assembled device incorporating the elements described above. Fluid inlet connectors 86 (either barbed or otherwise) allow for the connection of one or multiple drainage structures or tubes (as described above) to the pump unit of the device. In this embodiment, two drainage structures are accommodated; however, additional structures may be provided for by including additional assemblies of the relevant components. For each fluid inlet, immediately downstream of the connector is a one-way valve, as described above, to prevent the backflow of material into the drainage structure. Downstream of the one-way valve is a fluid chamber 82, which includes a pressure sensor 84 to monitor the pressure developed in the device. Tubing allows fluid from this chamber to flow into a peristaltic, or positive displacement, pump 83, which applies negative pressure on the upstream side of the pump, and positive pressure on the downstream side. This positive pressure downstream of the pump causes fluid to be transported through the remainder of the pump housing body and connection elements to a reservoir unit 77.

A set of one-way valves 79, 80 may be incorporated at the connection between the pump housing body and the reservoir to prevent fluid leakage during change of reservoirs. The reservoirs may be collapsible in nature which are much more comfortable to the patient, and may be made in a more economic, and environmentally conscious, way as the collapsible reservoir will necessitate a smaller volume of plastic to produce. The reservoir incorporates some means of removably attaching to the pump body, which allows the reservoir to be conveniently detached and replaced by the patient. In this embodiment, a connector 78 is attached to the reservoir, which mates to a counterpart receptor on the pump housing body.

As seen in FIG. 13, the reservoir unit comprises a pair of independent reservoirs as described above. The reservoir thus may contain several channels to allow the fluid from multiple drainage structures to be independently collected. These may be necessary if the healthcare professional desires to independently record the collected fluid amounts. Furthermore, the reservoir may be graduated, either by adhering a label or paint to the reservoir, or by embossing the plastic. These graduations allow the fluid collected fluid amount to be easily assessed.

The reservoir may also contain a substance intended to sterilize the collected fluid, and may also cause the fluid to congeal. This is necessary for the reservoir to be disposed of as "white bag" waste, or waste which may be disposed of in landfill without additional treatment. This substance may be contained in a pouch or container within the reservoir or may be freely distributed inside of the reservoir. This pouch or container may be ruptured by the patient in order to disburse the contents, or may simply dissolve within a convenient period of time.

The reservoir or manifold, or both, may further comprise one or more sensors or measurement devices, internally or externally, or both. These sensors provide diagnostic value in taking various measurements associated with the collected fluid. Measurements can include and are not limited to collected fluid amount, pH, certain known harmful mediators (cytokines, chemokines, reactive oxygen species), protein levels, blood content, etc. For example, amount of fluid collected can be an indicator of possible seroma development in some hernia surgeries. Additionally, pH has also been shown to act as an indicator of possible seroma formation. The present invention thus allows for the detection of infectious materials, and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds. Sensors may also be located in the pump unit.

Detection of a full reservoir may be accomplished by counting the revolutions of the peristaltic pump, or cycles of the positive displacement pump, and then calculating the total displaced fluid. This is made possible because the peristaltic, or positive displacement pump moves a nearly constant amount of fluid or gas with each revolution of its motor. The device may be powered by either consumable or rechargeable batteries 85 which are held in a battery holder.

A circuit control board 81 comprising some or all required electrical components controls the operation of the device. The control board may take as inputs, and make decisions regarding, the following: user inputs via interface buttons; battery charge level; need to change reservoir; device temperature; current magnitude of negative pressure; presence of blockage in tubing; or the characteristics of the collected fluids. These characteristics may include, but are not limited to, the following: total collected amount (either total or per drainage structure); rate of fluid collection (total or per drainage structure) on the time scales of hours, days, or weeks; presence of infectious materials; and any other chemicals or substances which may indicate infection, or the presence of some medical condition which may naturally arise in response to the surgical procedure, initial pathology, or additional complications (of either the surgical procedure or the initial pathology) in the fluid collected from percutaneous (internal) wounds.

The user interface may comprise a single push-button 75, which controls an on/off or pause function, as well as any other functions which are desirable for the operation of the device. One operation may be the selection of desired level of negative pressure. The interface may also consist of a series of lights or a screen which alerts the user to various conditions including, but not limited to, device power state (off/on/paused), selected pressure level, battery charge level, need to change battery, reservoir fill level, need to change reservoir, insufficient vacuum seal at any point in the system, or presence of infections materials, and any other chemicals or substances which may indicate infection, or the presence of some medical condition. The device may apply a negative pressure in the range of 50 mmHg to 700 mmHg below ambient pressure either continuously or intermittently, or operate solely in range from 200 mmHg and 700 mmHg below ambient pressure, either continuously or intermittently. The device may create a constant negative pressure of a desired amount and then allow the motors to momentarily stop, until a time when the onboard pressure sensors detect that the applied pressure has fallen below some desired threshold. Alternatively, the pumps may apply pressure based on a time increment rather than a pressure level.

Figure 14:
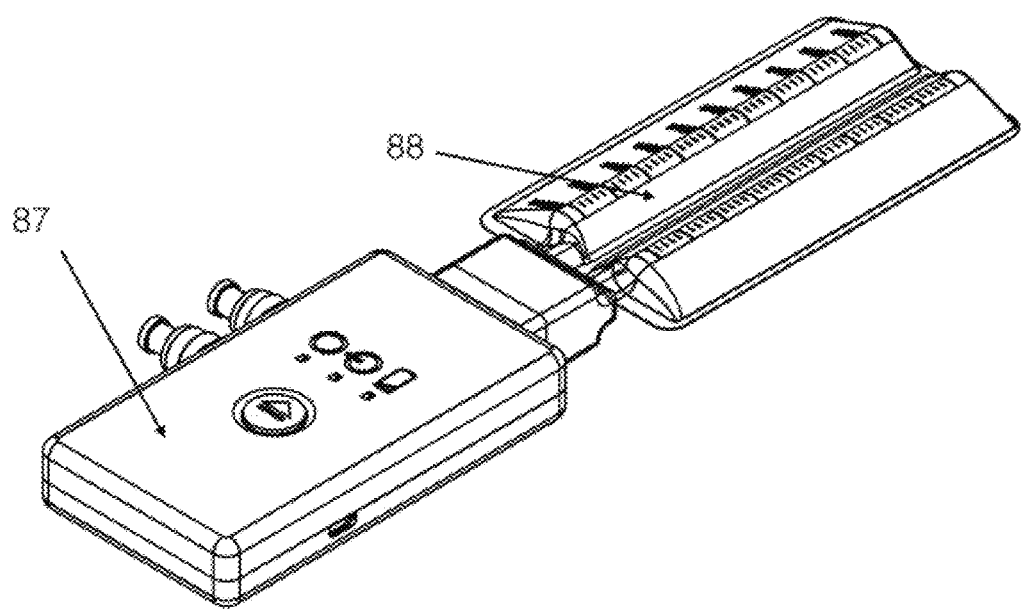
FIG. 14 is an assembled view of one embodiment of a pump unit in accordance with an exemplary embodiment of the present invention.

FIG. 14 shows a perspective view of the assembled pump unit device 87 and reservoir 88 as detailed above in the description of FIG. 13. In this embodiment, the pump unit is relatively flat and rectangular, with rounded edges and corners.

Figure 15:
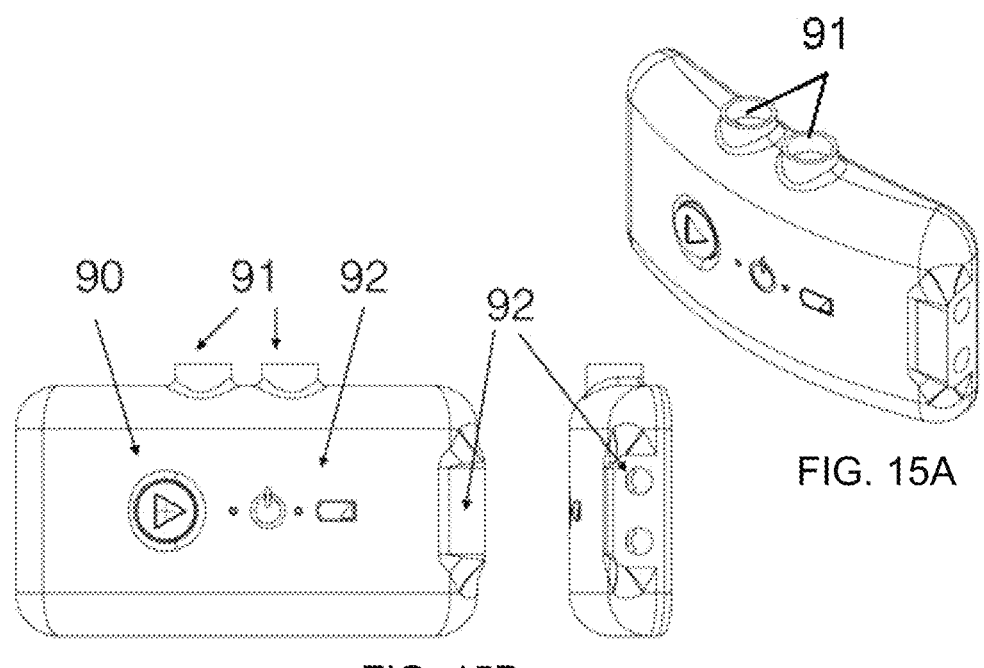
FIGS. 15A, 15B, and 15C are an assembled views of the pump housing of FIG. 14, with 15A showing a left raised perspective view, 15B a combined aerial and right side end view, and 15C a bottom side view thereof.
Figure 16:
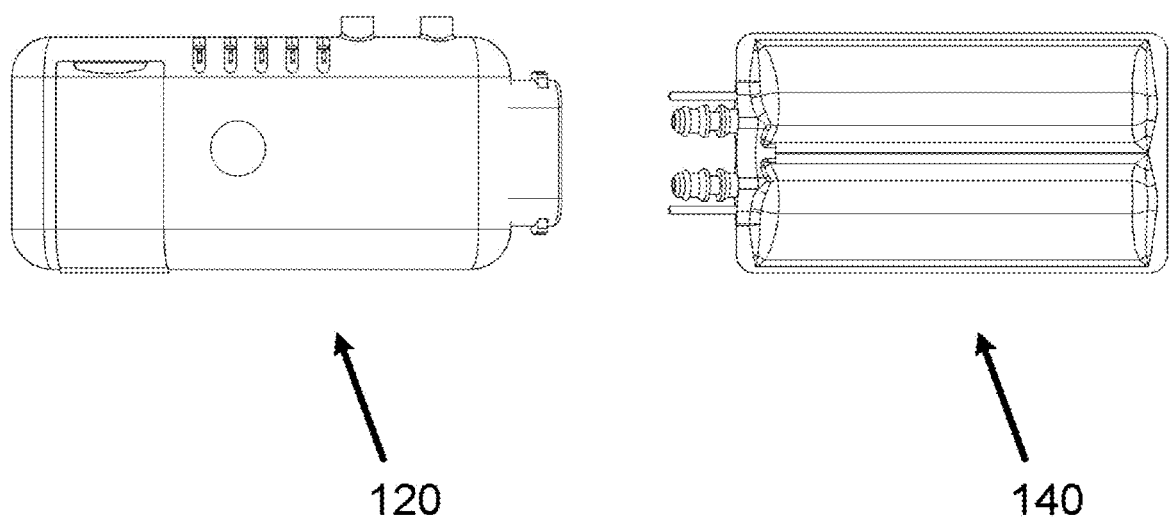
FIGS. 16-23 show views of an alternative embodiment of a pump unit and reservoir.
Figure 17:
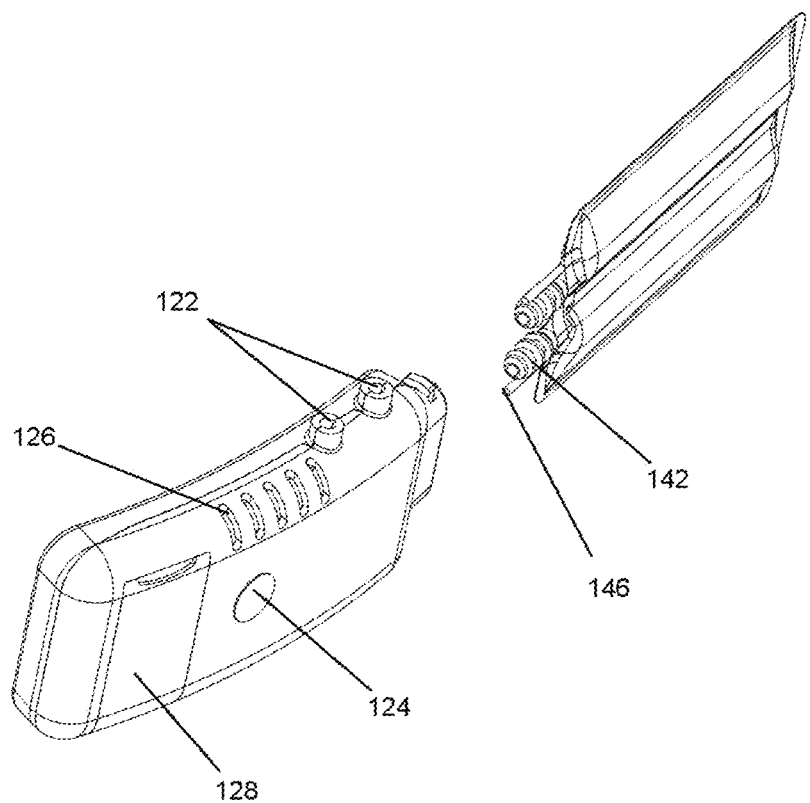
Figure 18:
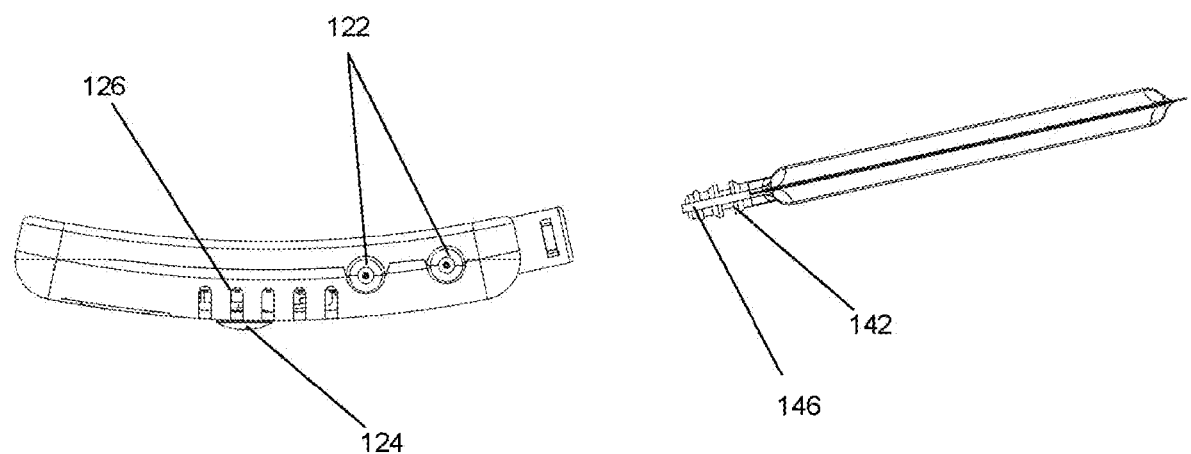
Figure 19:
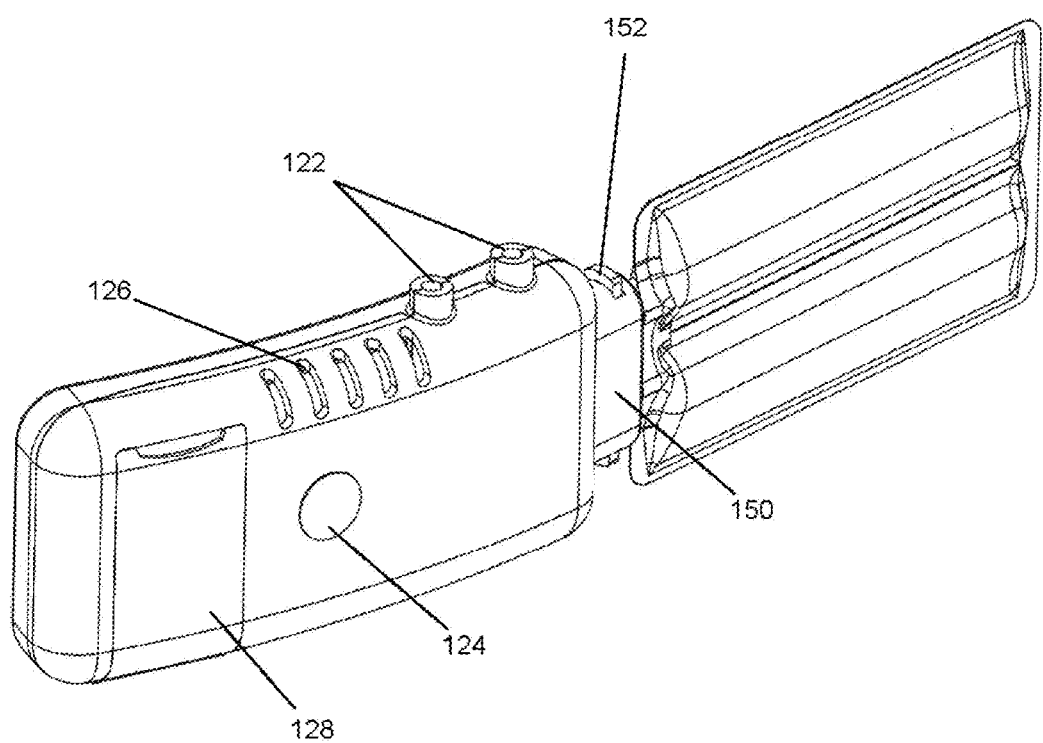
Figure 20:
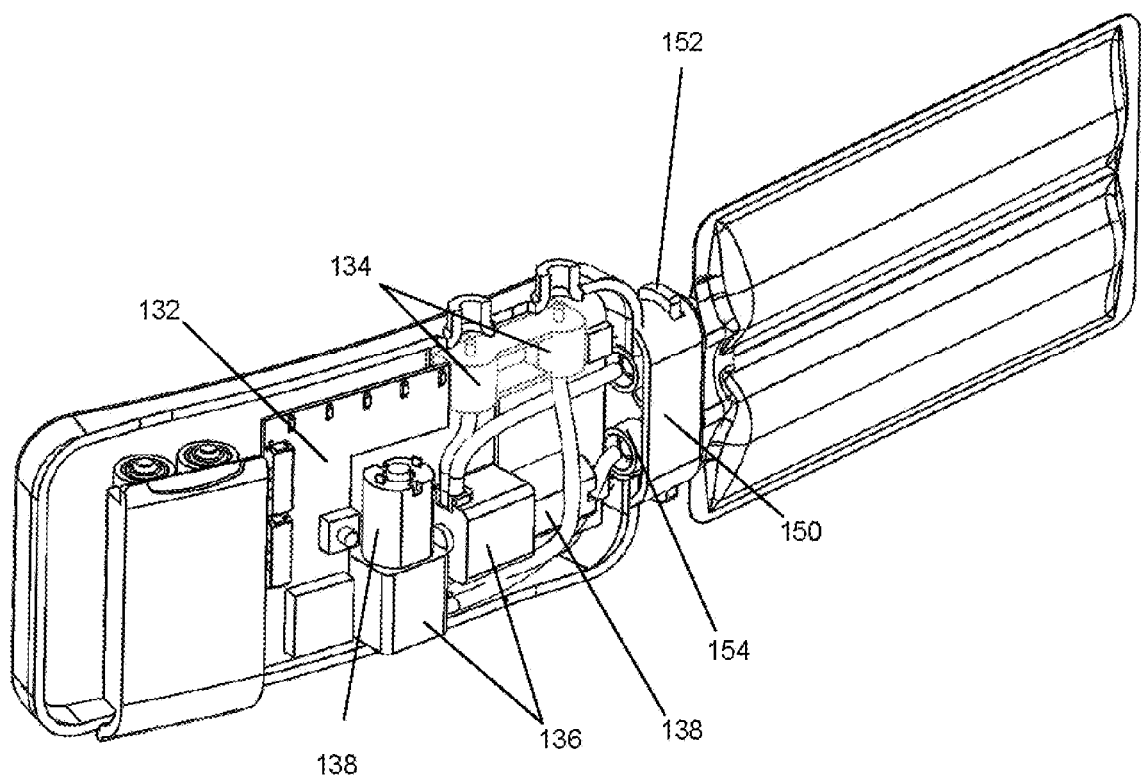
Figure 21:
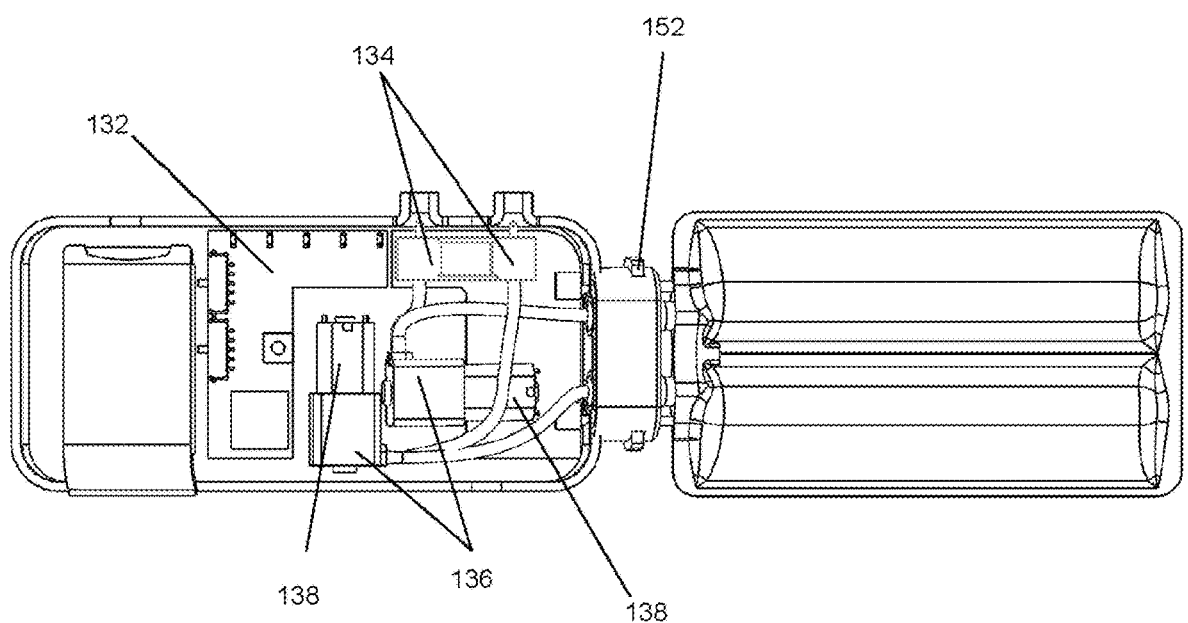
Figure 22:
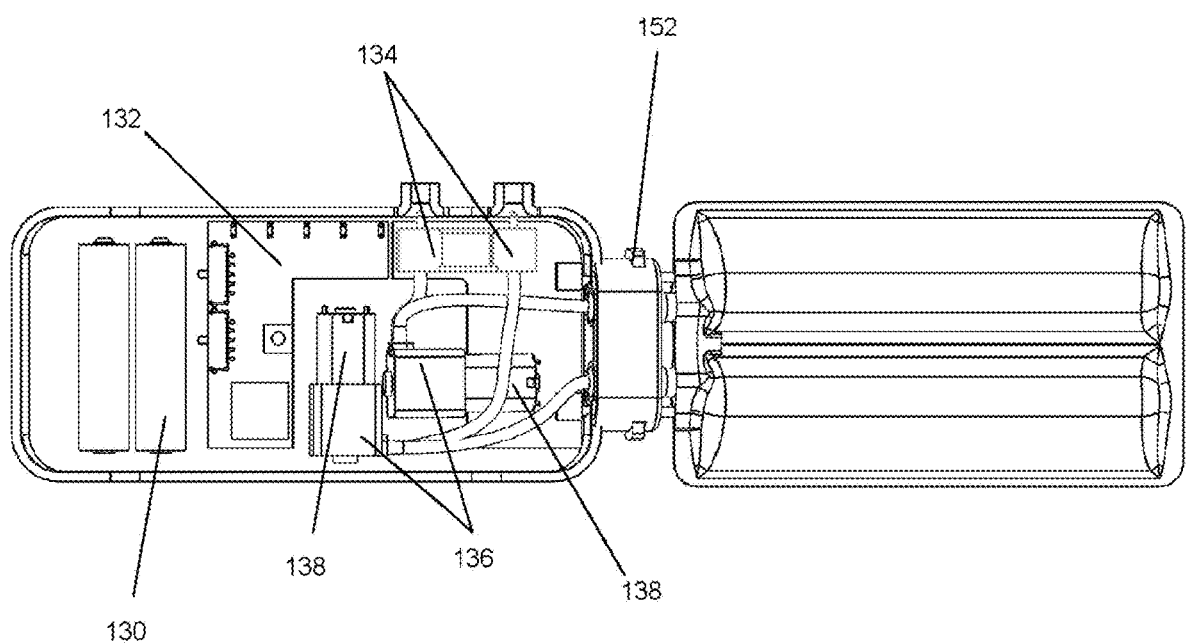
Figure 23:
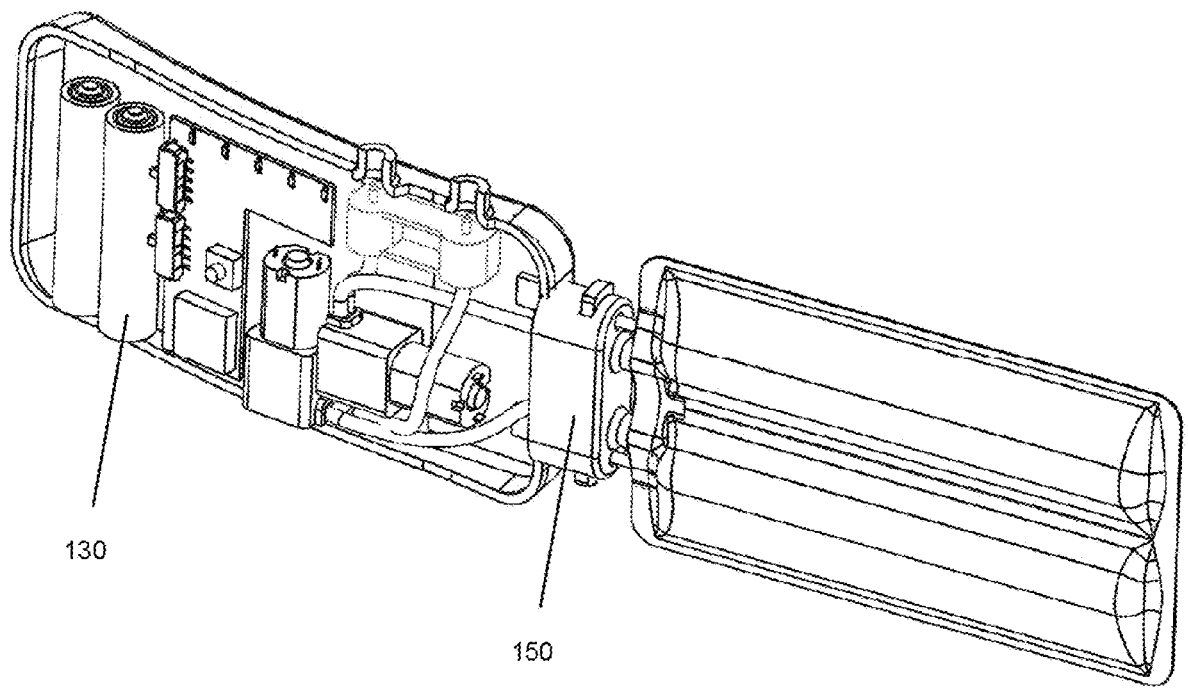
Figure 24:
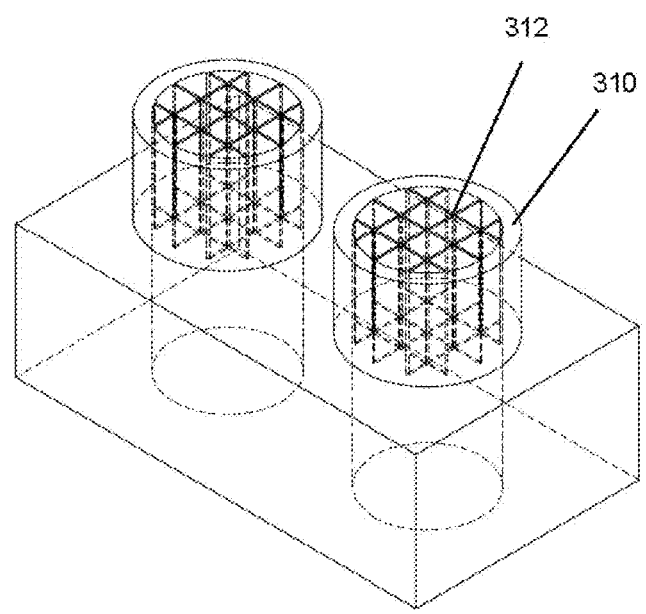
FIG. 24 shows a view of inlet ports with mesh.

FIGS. 15A-C show several views of another exemplary embodiment of the assembled pump unit device. In this embodiment, the edges and corners may be more rounded and the entire unit may be curved, as shown. The front or top of the device provides a user interface comprising a single push-button 90, and lights 96 which indicate the status of the unit (which may include but not be limited to on/off, device paused, reservoir full, or faulty tubing connection). The unit may comprise two (or more, as described above) fluid inlets 91, which provide the connection for two drainage structures, and two (or more, to correspond to the fluid inlets) fluid outlets 92, which allow the fluid to be transported to the collection reservoir. As seen in FIG. 15C, the housing 93 is curved in order to conform to the shape of the human abdomen on which the device will be worn. The device may curve not only along the horizontal axis (i.e., lengthwise), but also along the vertical axis (i.e., widthwise).

FIGS. 16-23 yet another embodiment of the pump unit 120 and reservoir 140 of the present invention, unconnected and connected. FIGS. 20-23 show the interior of the pump unit (i.e., with the front half of the pump unit housing removed. In this embodiment, the pump unit 120 is curved in a similar manner to the pump unit shown in FIGS. 15A-C. A pair of inlet ports/connectors 122 with one-way valves and inlet fluid chambers 134 are located near one end. A push-button interface 124 is located on the top or front of the pump housing, and a series of lights 126 are located on the side near the inlet ports (which is generally the top side, when the unit is worn). A battery cover 128 allows access to the batteries 130, which provide power to the circuit control board 132 and the pump motors 138. Pumps 136 move fluid to the outlet ports/connectors 154, which are contained in the reservoir holder 150. Pairs of one-way valves 142 extend from one end of the reservoir unit 140 (which contains two independent reservoirs in the embodiment shown) and are inserted into the outlet ports/connectors 154 to attach the reservoir unit to the pump unit. One or more rigid or semi-rigid guides 146 may be provided to fit into corresponding slots or holes in the reservoir holder 150. This establishes connection with a sensor or switch, which enables the control board in the pump unit to determine whether the reservoir unit is attached, as described below. The guides also may help ensure accurate connection and prevent damage to the one-way valves or other connection elements. One or more quick-release tabs or buttons 152 may be provided to allow the reservoir unit to be disengaged and easily removed when pressed.

Figure 25A:
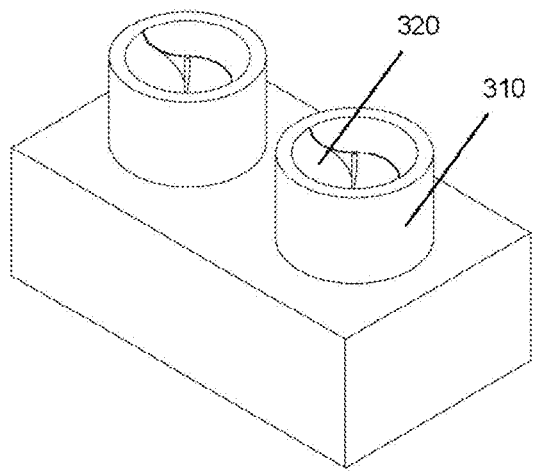
FIGS. 25A-C show views of inlet ports with a rotary blade.
Figure 25B:
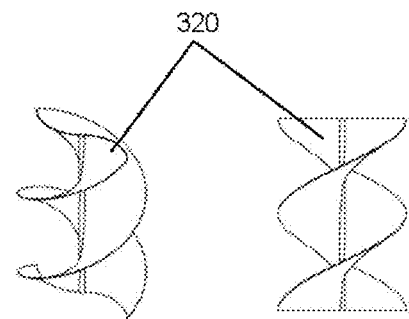
Figure 25C:
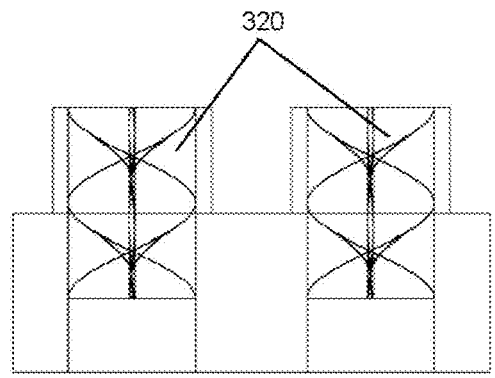
Figure 26A:
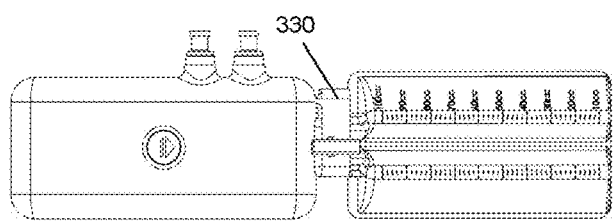
FIGS. 26A-D show views of a reservoir connection unit with integrated filters.
Figure 26D:
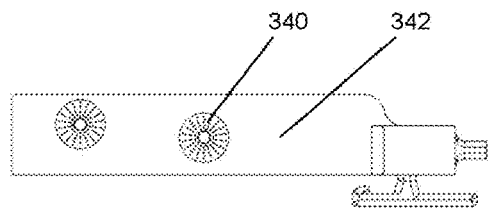
Figure 26B:
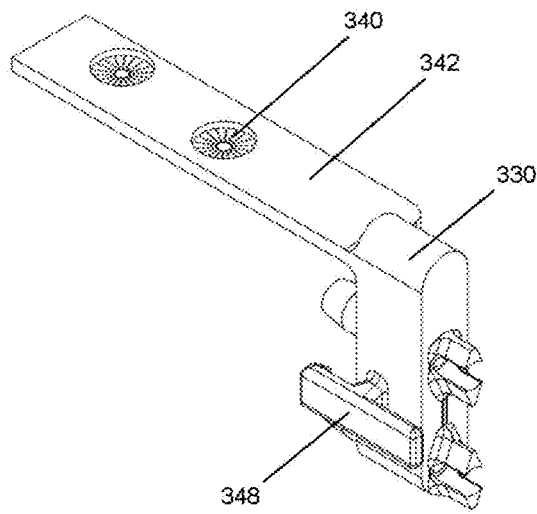
Figure 26C:
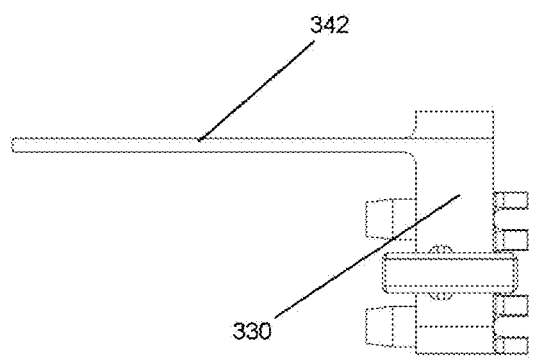

In several embodiments, as seen in FIG. 25, the fluid inlet ports 310 may further comprise a grate or mesh 312, which breaks-up or divides any particles or similar larger material in the fluid which may have been collected during operation. Alternatively, as seen in FIGS. 26A-C, the fluid inlet ports 310 may comprise a rotating blade 320 or rotary apparatus for the same purpose. The blade 320 may spin within the fixed port by either a powered motor or by the power provided by movement of the fluid. In the latter case, the blade has geometry to transform the fluid flow to rotational force, as well as separate geometry to break-up or divide particles or similar larger material as described above.

In yet another exemplary embodiment, filters 340 are provided on a reservoir connection unit 330 which is attached to one end of the reservoir unit 140. When the reservoir connection unit is used to attach the reservoir unit 140 to the pump unit 120, the filter arm 342 with filters 340 is inserted into a slot in the end of the pump unit, so the filters 340 are inserted into the fluid flow lines in the body of the pump unit 120. When the reservoir unit is removed (such as by pressing the quick release latch 348), the reservoir connection unit and filters are also removed. The reservoir connection unit and filters can be disposed of with the reservoir. In one embodiment, the filters or reservoir connection unit, or both, may be removable from the reservoir unit, and cleaned for re-use.

In yet another embodiment of the invention, the reservoir unit prevents re-connection to the pump unit after an initial connection to the pump unit (or other suction apparatus). This prevents re-attachment of a presumably full reservoir unit, and the attempted movement of fluid into a full fluid collection reservoir.

In a further embodiment of the invention, the pump control unit can detect whether a reservoir unit is connected to the outlet ports/connections, and prevents normal operation (i.e., the pumping of fluid) without a reservoir present to contain the fluid. The detection mechanism may comprise a mechanical switch or latch, the formation or breaking of an optical pathway, or similar mechanism appropriate for determining or confirming proximity.

The various embodiments of the present invention thus provide substantial improvements and advantages over the prior art. First, the present invention allows multiple drainage tubes to be connected to the same source of negative pressure. Prior art devices lack the functionality to allow the combination of multiple drainage tubes into a common source of negative pressure, thus requiring patients in surgeries necessitating multiple drains to wear multiple instances of the previously described device. Second, the present invention also places the reservoir after the negative pressure source. Prior art systems require the reservoir to be placed between the tubing leading from the internal wound site and the source of the negative pressure, which impairs functioning of the device. For example, gravity's action on the fluid to provide an air space on which the source of negative pressure may act prevents prior art devices from functioning optimally while the patient is in the prone or supine position. Furthermore, the placement of the reservoir in prior art devices increases the working distance between the source of negative pressure and the internal wound, necessitating that it act on a larger volume, reducing the efficiency of the device, and creating a source of oscillating pressure in the case of a temporary blockage which is suddenly freed. Third, prior art devices make use of a perforated internal drain which allows the collection of fluid. The present system comprises a manifold which allows the use of the unique internal drain described herein or the use of one or more of the many conventional internal drainage structures which the surgeon may prefer. Further, the present invention incorporates adaptor fittings which allow any size or sizes (in the case of multiple drain lines) to be utilized.

Additionally, prior art devices prescribe the application of a pressure regime from 125 mmHg to 200 mmHg below atmospheric. At this range, it is unlikely that the device will impart sufficient force on any impediment to flow which may become lodged in the drainage tubing such as a mass of clotted blood, fibrous material, or small portion of tissue. The present invention may operate at a pressure above 200 mmHg for certain periods of operation, such as the initial drawing together of the separated (surgically or otherwise) tissue and the clearing of a blockage. At other times, the present invention may operate at lower pressures in order to allow a more passive means of suctioning. Further, prior art devices do not incorporate a disposable reservoir, and do not allow neutralizing any odor from the collected fluid. The present invention comprises a fluid reservoir inherently designed to be disposable and is placed downstream from the source of negative pressure, negating the previously described problems with prior art devices.

Prior art devices do not allow for the accurate measurement of collection fluid, or derivative measurements. The present invention allows for the measurement of the amount of collected fluid in either the input manifold or the reservoir, and further calculates the calculation of the percentage of collected fluid to air which would allow for the prediction of poor suturing and possibly surgical site infection (SSI). To accomplish this, the present invention carries out the following steps:
1. Calculating the amount of total volume (air plus liquid) collected via counting revolutions of peristaltic rotor.
2. Calculating the collected fluid amount by positioning a series of electrode pairs acting as graduations in the reservoir or by making use of the fluid measurement units in the manifold.
3. Calculating the ratio of total collected volume to total collected fluid.

In order to provide a context for the various computer-implemented aspects of the invention, the following discussion provides a brief, general description of a suitable computing environment in which the various aspects of the present invention may be implemented. A computing system environment is one example of a suitable computing environment but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purposes or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, microprocessor-based systems, multiprocessor systems, TV set-top boxes and devices, programmable consumer electronics, cell phones, personal digital assistants (PDAs), tablets, smart phones, touch screen devices, smart TV, internet enabled appliances, internet enabled security systems, internet enabled gaming systems, internet enabled watches; internet enabled cars (or transportation), network PCs, minicomputers, mainframe computers, embedded systems, virtual systems, distributed computing environments, streaming environments, volatile environments, and the like.

Embodiments of the invention may be implemented in the form of computer-executable instructions, such as program code or program modules, being executed by a computer, virtual computer, or computing device. Program code or modules may include programs, objects, components, data elements and structures, routines, subroutines, functions and the like. These are used to perform or implement particular tasks or functions. Embodiments of the invention also may be implemented in distributed computing environments. In such environments, tasks are performed by remote processing devices linked via a communications network or other data transmission medium, and data and program code or modules may be located in both local and remote computer storage media including memory storage devices such as, but not limited to, hard drives, solid state drives (SSD), flash drives, USB drives, optical drives, and internet-based storage (e.g., "cloud" storage).

In one embodiment, a computer system comprises multiple client devices in communication with one or more server devices through or over a network, although in some cases no server device is used. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. The client devices each comprise a computer-readable medium in the form of volatile and/or nonvolatile memory such as read only memory (ROM) and random access memory (RAM) in communication with a processor. The processor executes computer-executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may further comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmission device, a floppy disk, hard disk drive, CD-ROM, DVD, magnetic disk, memory chip, ROM, RAM, EEPROM, flash memory or other memory technology, an ASIC, a configured processor, CDROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infrared, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C#, Visual Basic, Java, and the like.

Components of a general-purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic routines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically connected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be connected through an output peripheral interface.

Client devices may operate on any operating system capable of supporting an application of the type disclosed herein. Client devices also may support a browser or browser-enabled application. Examples of client devices include, but are not limited to, personal computers, laptop computers, personal digital assistants, computer notebooks, hand-held devices, cellular phones, mobile phones, smart phones, pagers, digital tablets, Internet appliances, and other processor-based devices. Users may communicate with each other, and with other systems, networks, and devices, over the network through the respective client devices.

As it concerns FIGS. 27A-31, there are provided different configurations and manners of practicing such fluid removal in terms of measurements and separations of constituents therein.

Figure 27A:
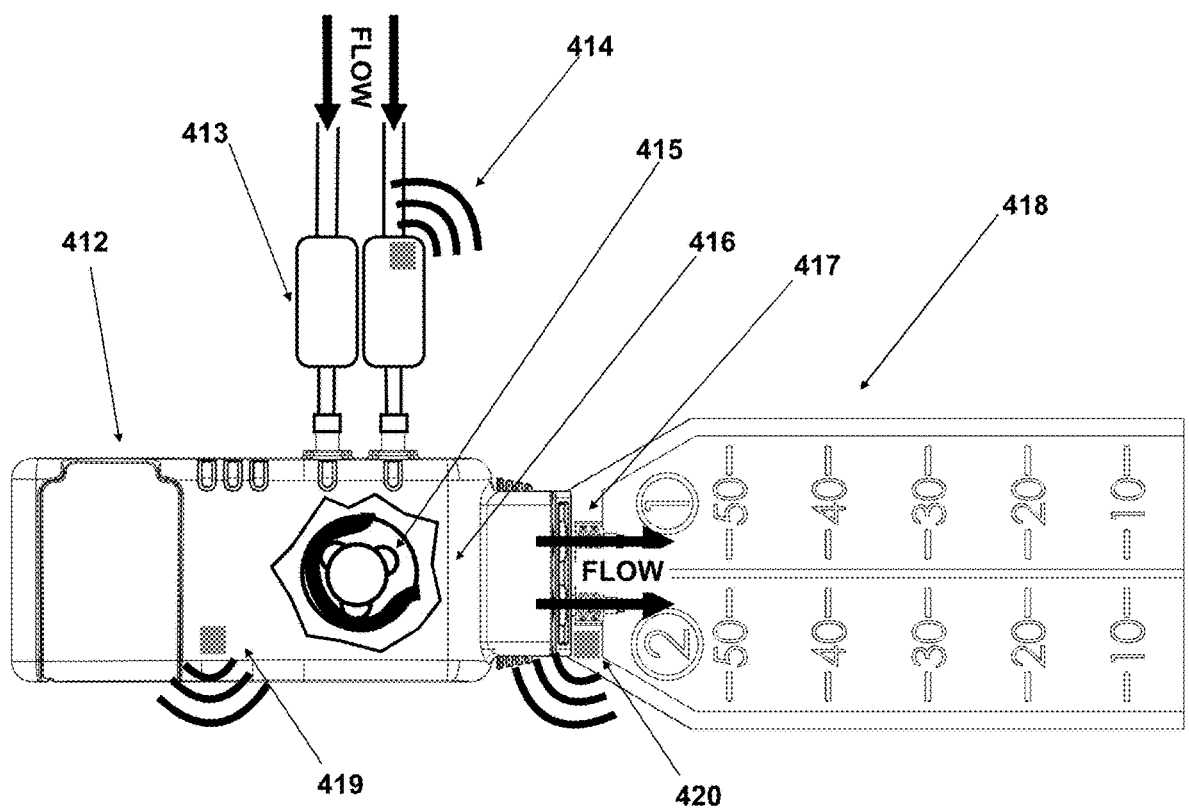
FIG. 27A is a view of one embodiment of the system used to facilitate collection of the sample, and the means to store the collected sample.
Figure 27B:
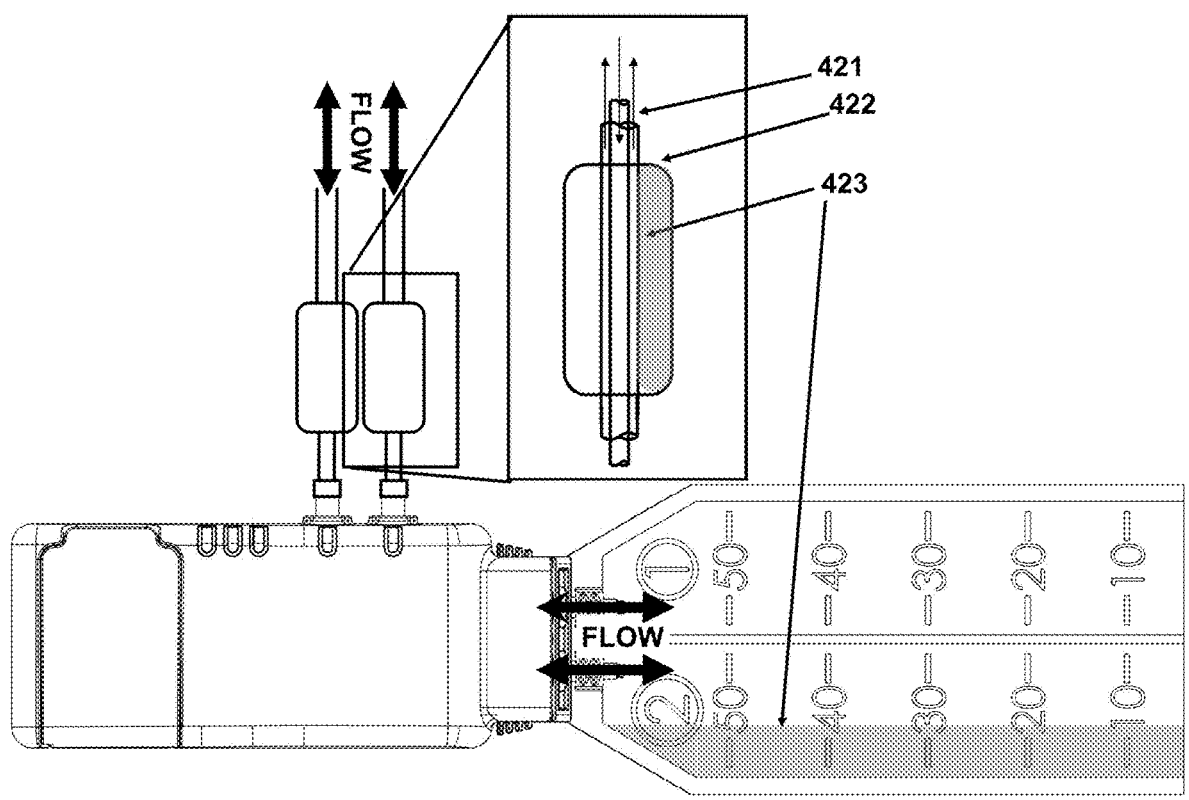
FIG. 27B is a view of one embodiment of the system used to facilitate collection of the sample and delivery of medically useful material to the patient, and the means to store the collected sample and medically useful material.
Figure 28A:
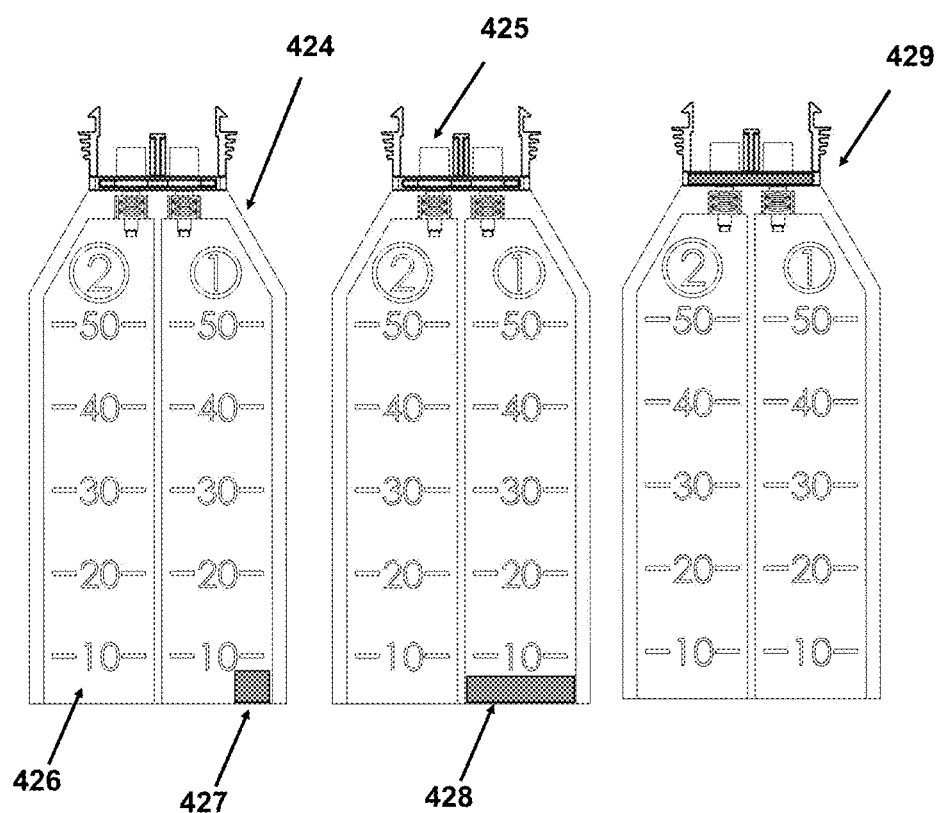
FIG. 28A is a view of several embodiments of the sample-collection apparatus in the downstream configuration with several embodiments of mechanisms to store data about the sample on the unit itself.
Figure 28B:
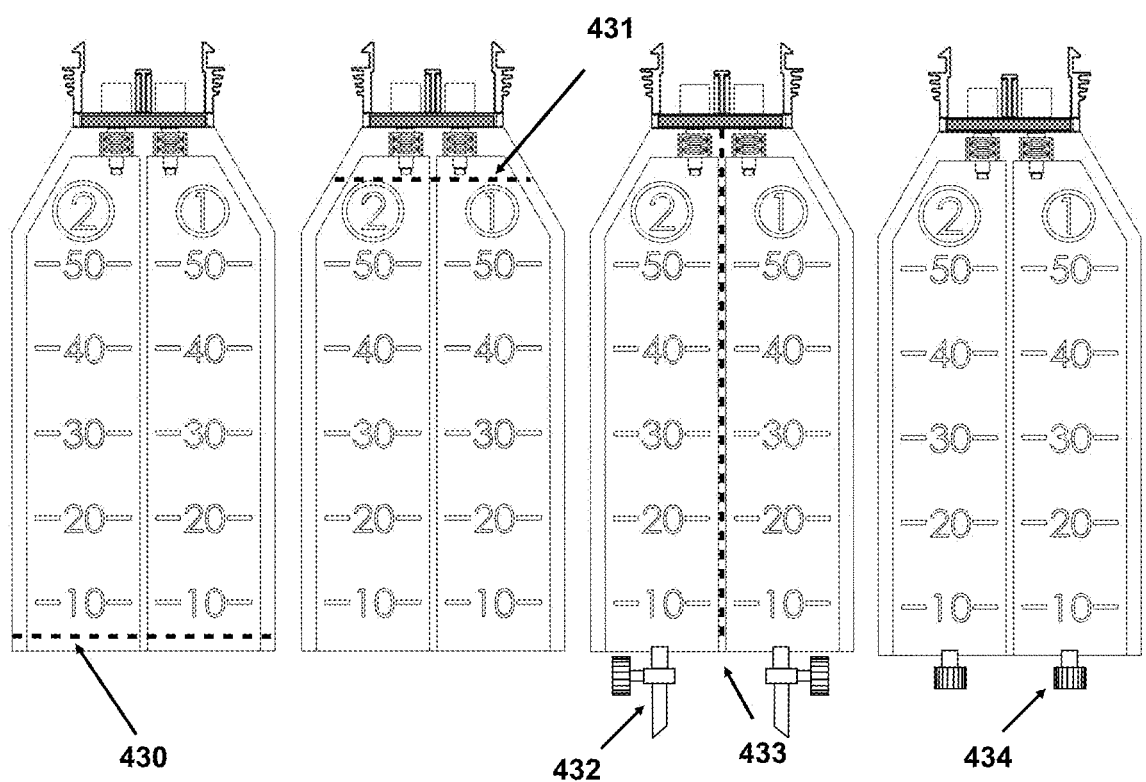
FIG. 28B is a view of several embodiments of the sample-collection apparatus in the downstream configuration shown with several embodiments of mechanisms to remove collected sample from the unit.
Figure 28C:
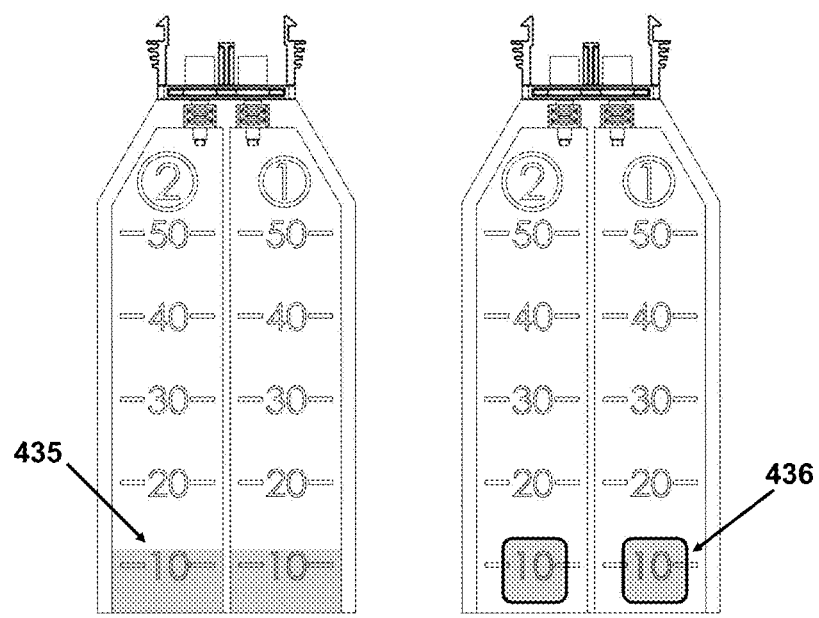
FIG. 28C is a view of two embodiments of the sample-collection apparatus in the downstream configuration shown with two embodiments of a sample-treatment substance contained in the apparatus.
Figure 28D:
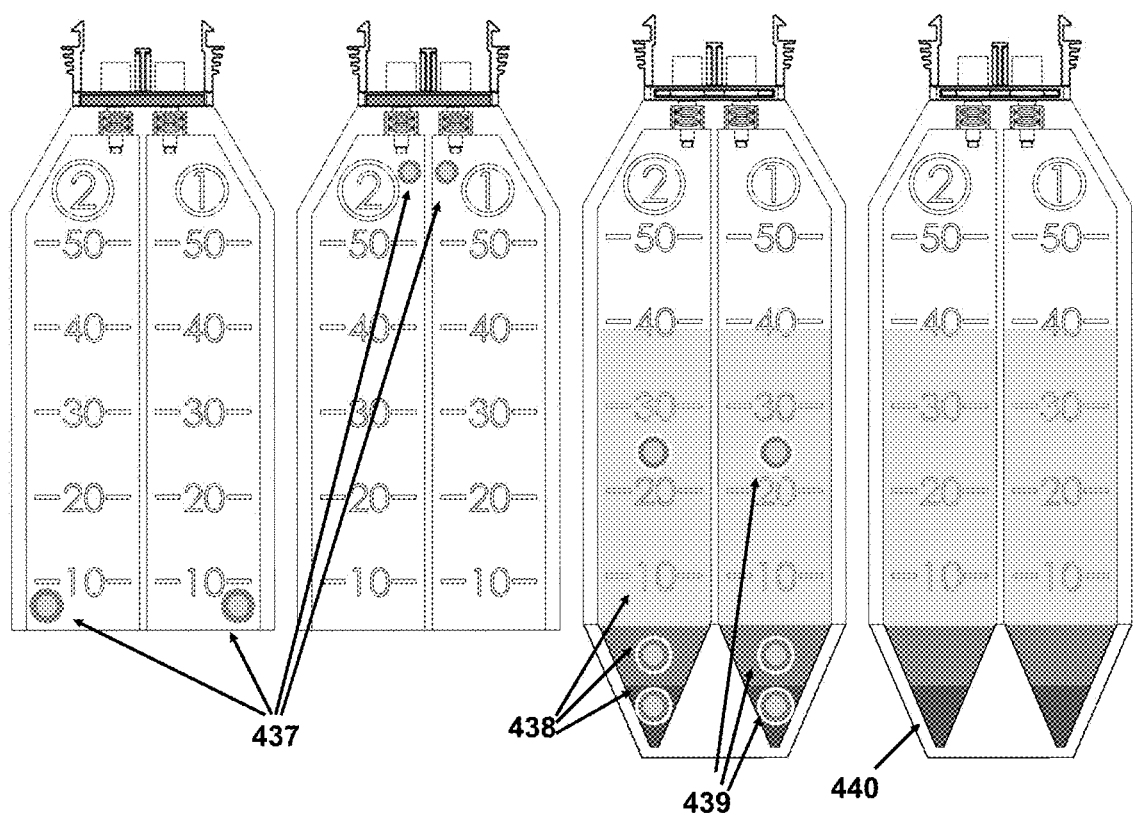
FIG. 28D is a view of several embodiments of the sample-collection apparatus in the downstream configuration shown with two embodiments of a mechanism to remove sample from the apparatus, and one embodiment of a mechanism to process the sample without removing sample from the apparatus.
Figure 28E:
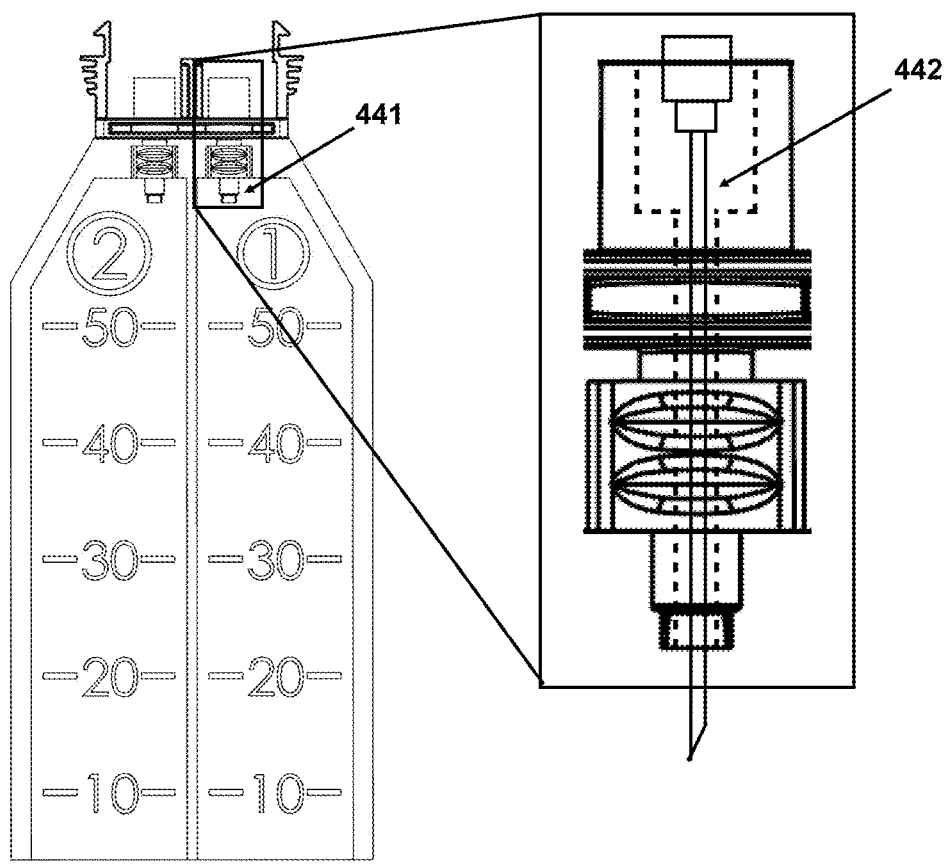
FIG. 28E is a view of one embodiment of the sample-collection apparatus in the downstream configuration shown with one embodiment of a mechanism to remove the sample from the apparatus.

FIG. 27A-27B show an exemplary embodiment of the device intended to create a negative pressure on the upstream (towards patient) side of a peristaltic mechanism 416, and a positive pressure downstream (away from patient) of the peristaltic mechanism which is intended to drive the collected sample into the sample-collecting apparatus. The device may possess multiple inlets. The sample-collecting apparatus may be connected to the device by a connection 416 and made to be detachable from the device and sent for additional testing as described in the detailed description of FIG. 1, or the entire apparatus and device may be transported for additional testing. In addition to a downstream sample-collection apparatus, an upstream sample-collection apparatus 413 may be connected upstream of the peristaltic mechanism. This upstream sample-collection apparatus is subject the same shipment protocol as described in the detailed description of FIG. 1. The device, upstream sample-collection apparatus, and downstream sample-collection may all possess features 414, 419, 420, which allow them to communicate with one another. In one embodiment, the upstream sample-collection apparatus and downstream sample-collection apparatus (separately or together) communicate with the device through some wired or wireless means, and the device communicates with the patient, caregiver, or health-care professional via wired or wireless means including making use of wireless cellular networks, satellite networks, Bluetooth or mesh network communication with a cellular device, modem, or other internet or communication-enabled device. The information communicated between the upstream and downstream sample-collection apparatus may include one or more of the following relevant characteristics of the collected sample: date of collection, elapsed time of collection, sample amount, sample chemical or biological characteristic, sample temperature at any or all times during collection, patient or sample identifying information, or shipping information. The device may then relay to the patient, caregiver, healthcare provider, or other interested party or process and encode back in the sample-collecting apparatus any or all of this information. The upstream sample-collection apparatus is further depicted in FIG. 29A-29B. The downstream sample-collection apparatus is further depicted in FIG. 28A-28E.

In one embodiment of the device, either the upstream or downstream sample-collection apparatus, or the device, itself, may contain a reservoir of material 423 intended to be delivered to the patient for the purposes of pain-relief, treatment of disease (including any form of cancer) or infection, or any other medically-useful purpose. This material may be delivered at one or more time-points based on several factors which are either pre-programmed, determined by the device or sample-collection unit based on patient or sample parameters determined by onboard analysis, or delivered to the device via some communication protocol or feature (e.g. the healthcare provider determines that the dosage of material should be increased, and is able to send instructions to the device to deliver material accordingly; the device may relay the patient or sample parameters to the healthcare provider for analysis in order for this determination to be made). The inlet to the device, which may include the upstream sample-collection apparatus may possess multiple cannulae 421, 422 which facilitate motion of fluid both out of, and into the patient. In one embodiment, sample is collected from the patient, analyzed by the device, and based on that analysis, material as herein described is transferred to the patient via the same or different cannula.

FIG. 28A-28E show an embodiment of the sample-collection unit or apparatus 424, into which fluid or biological sample is transferred after a collection process facilitated by a device as described in FIG. 27A-27B, or by the sample-collection apparatus itself. Furthermore, the sample-collection apparatus may serve as the terminal vessel in which all further analysis of its contents (i.e. the sample) is carried out, thus ensuring a secure, repeatable, non-contaminated sample during the chain-of-custody from collection to analysis results. The sample-collection apparatus and its associated packaging may be constructed to control, either actively or passively, characteristics of the sample and any associated packaging which include, but are not limited to the following: temperature, humidity, UV light transmittance and absorbance, shock and vibration, fluid ingress or egress, pH, gas ingress, egress, ambient concentration or absorbance, or any other biologically, clinically, or physically relevant characteristic. In one embodiment, the sample-collection apparatus is comprised of a flexible material with a specialized connector or inlet 425 which may facilitate easy installation and removal from the device as described in FIG. 27A-27B. The waste collection unit may be divided into one or more independent chambers, each of which are individually graduated with visible markings 426 to allow easy determination of the collected fluid. Furthermore, the sample-collection apparatus may possess some means of storing data pertaining to the collected fluid such as an Radio Frequency Identification (RFID) device 427 or barcode or quick response (QR) code 428, 429. The information contained in these devices is not limited to, but may contain any of the following: date of collection, elapsed time of collection, sample amount, sample chemical or biological characteristic, sample temperature at any or all times during collection, patient or sample identifying information, or shipping information.

In one embodiment, the sample-collection unit possesses features to facilitate removal of the collected sample. The sample-collection unit may possess perforations 430, 431 at either the top or bottom of the unit, which allow the unit to be easily opened. These perforations may be created in such a way as to not puncture the entirety of the collection unit, but rather form weakened points in the material, which facilitate origins for tearing or cutting the sample-collection unit. Furthermore the sample-collection unit may possess a stopcock 432, capped 434 or non-capped twist-open or squeeze-open outlet to allow easy removal of stored fluid. Additionally, the sample-collection unit may be easily divided into one or more separate collection and analysis chambers by means of a perforated seam 433, or other mechanism which facilitates separation.

In one embodiment, the sample-collection unit possesses a chemical or biologically derived substance intended to preserve, store, or otherwise modify the sample or sample environment after sample collection. This substance 435 may be placed loosely in the sample-collection unit, or may be further contained in a pouch, bag, or capsule 436 intended to introduce the substance to the sample by either degradation, puncturing, bursting, or other method of the pouch, bag, or capsule. The substance may contain, without any limitation intended, one or more of the following: dilution of alcohol, pH buffer, protease inhibitor, anticoagulant (for blood, protein, or other substance), crosslinker, stain for imaging purposes, cell or DNA fixative, gene, protein, bacteria, or other marker for labeling via immunohistochemistry or other means.

In one embodiment, the sample-collection unit may possess a self-sealing syringe adapter or port 437 at various positions in the unit which facilitate easy removal of collected sample by syringe. Furthermore, the sample-collection unit may be constructed in such a way as to create a conical, or otherwise tapered section 440, in order to facilitate centrifugation of the sample in the sample-collection unit itself, thus avoiding transfer of the sample out of the unit to another vessel (such as a capped centrifuge tube). The centrifugation of the sample-collection unit may inherently create stratification of the sample constituents 438, which may be directly removed from the sample collection unit by syringe adapters or ports or other features which allows sample collection 439 placed at varying locations on the sample-collection unit. Furthermore, the tapered section may be created by a separable tube or vessel, which facilitates easy means of transfer from the sample-collection unit to the vessel; the separable vessel may allow easier handling and analysis of the sample, while maintaining the simplicity and security enabled by obviating the need to transfer the sample out of the sample-collection unit.

In a further embodiment of the sample-collection apparatus, the inlet to the apparatus may possess a feature 441 which allows one-way transfer of fluid during collection such as a one-way valve. It may further possess a channel 442 which is appropriately designed to allow the passage of a syringe needle through the inlet and one-way valve to facilitate sample removal from the unit. The removal via syringe or similar implement may be either manually actuated by the patient, a technician or trained person, or by automated means.

Figure 29A:
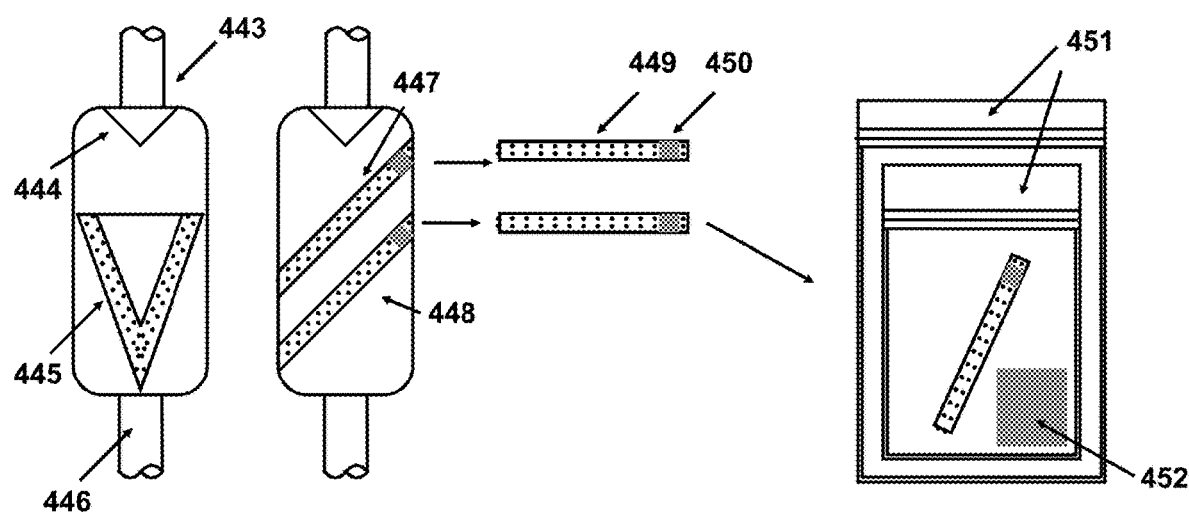
FIG. 29A is a view of two embodiments of the sample-collection apparatus in the upstream configuration shown with two embodiments of a filter to collect the sample and a mechanism for transporting the sample.
Figure 29B:
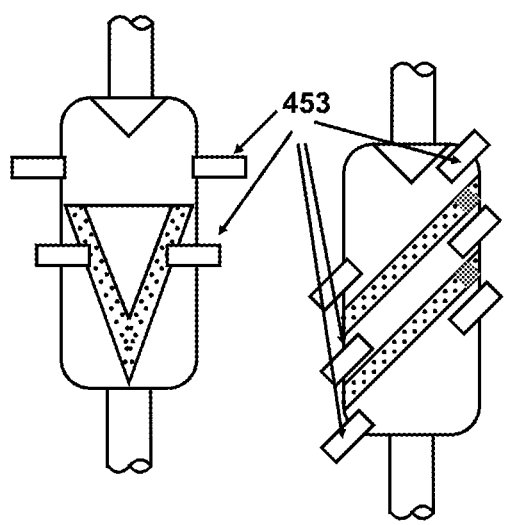
FIG. 29B is a view of two embodiments of the sample-collection apparatus in the upstream configuration shown with two embodiments of sensors incorporated in the apparatus.

FIG. 29A-29B shows various embodiments of the sample collection unit in the upstream configuration, however, all of the described features may also be implemented in the sample-collection unit in the downstream configuration. In one embodiment, the upstream sample-collection unit possesses an inlet 443, which may be connected to the patient by some means including commonly-used drainage tubing, or wound pad, and an outlet 446, which may be connected to the device as described in the detailed description of FIG. 27A-27B one-way valve 444 is placed immediately after the inlet which is designed to allow the passage of collected sample or fluid, but disallow the backflow of material (including air). The sample-collection unit may possess a filter, or several filters in either the conical configuration 445, or in a near-perpendicular-to-flow configuration 447, 448, which are selected based on filtration size, and are intended to capture various debris in the sample, for either removal, or collection for further analysis. The entire sample-collection unit, or one or more filters 449 may be individually or collectively shipped for further analysis. The filters or sample collection unit may possess features 50 which allow for the storage of data which may include but is not limited to date of collection, elapsed time of collection, sample amount, sample chemical or biological characteristic, sample temperature at any or all times during collection, patient or sample identifying information, or shipping information. The filters, or collection unit may be shipped in a single or doubled-bagged container 451, which itself may possess features 452 including barcodes, QR codes, or RFID tags which allow for the storage of data which may include but is not limited to date of collection, elapsed time of collection, sample amount, sample chemical or biological characteristic, sample temperature at any or all times during collection, patient or sample identifying information, or shipping information. The sample-collection unit, filters, or shipping bay may also be capable of communicating with the device (as described in the detailed description of FIG. 2A-2B), patient, caregiver, healthcare provider, or interested party.

In one embodiment of the sample-collection unit, sensors 453 may be used to detect parameters including, but not limited to those elucidated by fluid cytology, and turbidity, the presence and characteristics of rare cells such as circulating tumor cells, proteins such as the carcinoembryonic antigen (CAE) and MUC-1, chemokines, growth factors and cytokines, cellular debris including cytoplasmic fluid, cytosol and proteins, gene profile, pH, cell count, presence of blood, presence of bacteria or other pathogens or infectious material or evidence of such, cell surface receptors or other markers for relevant disease states or conditions. Furthermore, sensors may be used to determine with the filter or sample-collection apparatus has reached capacity for the material it is intended to collect. The data collected by these sensors may be stored in implements in the sample-collection apparatus, filter, or transferred to the device described in the detailed description of FIG. 27A-27B.

Figure 30:
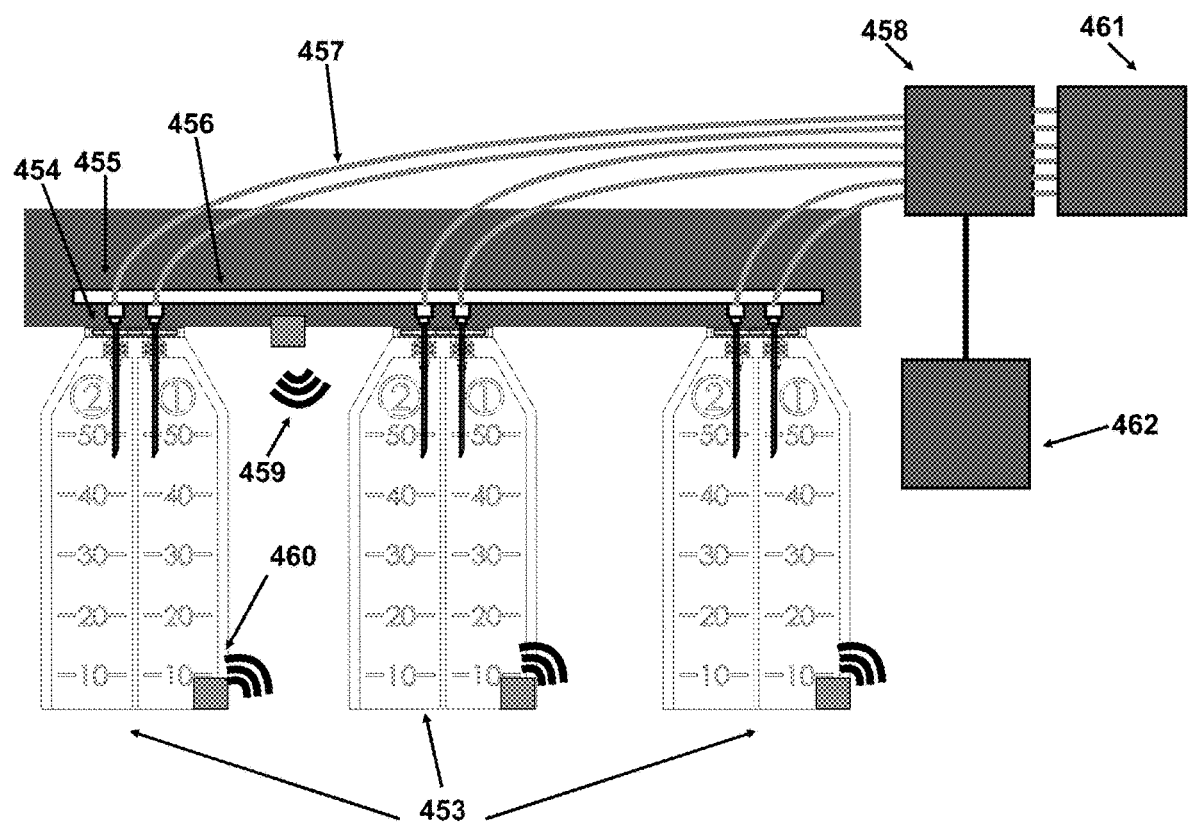
FIG. 30 is a schematic view of one embodiment of a mechanism for automatically removing, processing, analyzing, or processing and analyzing sample while in the sample-collection apparatus, and storing sample and sample data from the sample-collection apparatus in a large-scale operation such as a centralized or decentralized laboratory.

FIG. 30 shows one embodiment of a system for the analysis of the collected sample. In this embodiment, the sample collection units are connected to an automated system for the retrieval, processing and analysis, data storage, and residual sample storage, however one or all of these steps may be partially automated or fully manual. To allow for high-throughput of samples, several sample-collection units may be collected to the system concurrently via the same mechanism 454 used to connect the sample collection units to the device as described in the detailed description of FIG. 27A-27B. Stationary or automated mechanisms 455 may transfer the sample from the collection unit to one or more vessels or machines to be further processed. Prior to the removal of sample, the automated mechanism may centrifuge one or more of the samples concurrently or separately using the sample-collection apparatus as the sample-containment vehicle for centrifugation. In the case of an automated sample removal mechanism, a gantry or robotic shuttle mechanism 456 may facilitate the movement of the sample transfer mechanism from one sample-collection unit to another, or from sample-collection unit to some other vessel or machine to facilitate further processing or analysis. A processing or analysis mechanism 458 may be used to further process or analyze the sample for characteristics including, but not limited to those elucidated by fluid cytology, and turbidity, the presence and characteristics of rare cells such as circulating tumor cells, proteins such as the carcinoembryonic antigen (CAE) and MUC-1, chemokines, growth factors and cytokines, cellular debris including cytoplasmic fluid, cytosol and proteins, gene profile, pH, cell count, presence of blood, presence of bacteria or other pathogens or infectious material or evidence of such, cell surface receptors or other markers for relevant disease states or conditions. Individual fluid paths 457 may be employed to preserve the uniqueness of the samples. Sensors or readers 459 installed or incorporated in the mechanism may be used to read the RFID, barcode, QR code or other data-storage device 460 incorporated in the sample-collection mechanism. These may be one-way or two-way communication protocols. Data read or transferred may include, but are not limited to date of collection, elapsed time of collection, sample amount, sample chemical or biological characteristic, sample temperature at any or all times during collection, patient or sample identifying information, or shipping information. Once all processing is complete, the collected sample, in either processed or unprocessed form may be stored indefinitely by some means 461 for future processing, analysis, or other purposes. All data may likewise be stored indefinitely by some means 462 for future processing, analysis, or relay of pertinent information to the patient, caregiver, healthcare provider, or interested party. Machine learning, or large data-set processing algorithms may be used in the processing or analysis of the data.

Figure 31:
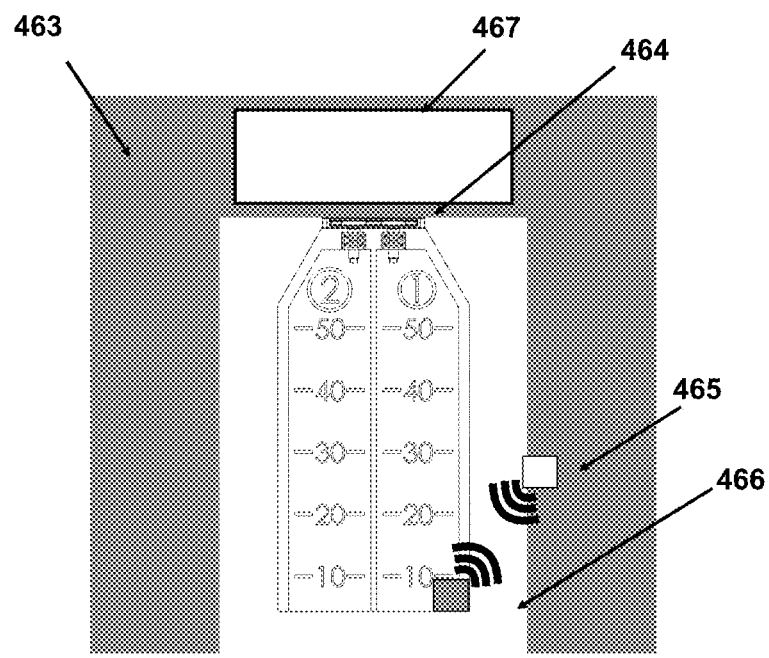
FIG. 31 is a schematic view of one embodiment of a mechanism for automatically removing, processing, analyzing, or processing and analyzing sample while in the sample-collection apparatus, and storing sample and sample data from the sample-collection apparatus in a small-scale operation such as home or hospital setting.

FIG. 31 shows on embodiment of a dock, or manual, decentralized version of the machinery described in the detailed description of FIG. 30. This embodiment may be placed in the home, clinic, hospital, pharmacy, or other inherently decentralized location for the processing, analysis, and storage of the sample and associated data, or for relay or immediate display of pertinent information to the patient, caregiver, healthcare provider, or interested party. The dock 463 may possess a means 464 for connecting to the sample-collection device using the same method described in the detailed description of FIG. 30. Sensors or readers 465 installed or incorporated in the mechanism may be used to read the RFID, barcode, QR code or other data-storage device 466 incorporated in the sample-collection mechanism. These may be one-way or two-way communication protocols. Data read or transferred may include, but are not limited to date of collection, elapsed time of collection, sample amount, sample chemical or biological characteristic, sample temperature at any or all times during collection, patient or sample identifying information, or shipping information. The dock may be used to further process or analyze the sample for characteristics. These characteristics include, but are not limited to those elucidated by fluid cytology, and turbidity, the presence and characteristics of rare cells such as circulating tumor cells, proteins such as the carcinoembryonic antigen (CAE) and MUC-1, chemokines, growth factors and cytokines, cellular debris including cytoplasmic fluid, cytosol and proteins, gene profile, pH, cell count, presence of blood, presence of bacteria or other pathogens or infectious material or evidence of such, cell surface receptors or other markers for relevant disease states or conditions. The dock may possess a cartridge or removable set of internal components to preserve the uniqueness of different samples from the same or different patients. The dock may possess a screen 467 to display results or clinically relevant information about the collected sample, or may transfer this information to the patient, caregiver, healthcare professional, or interested party.

Figure 32:
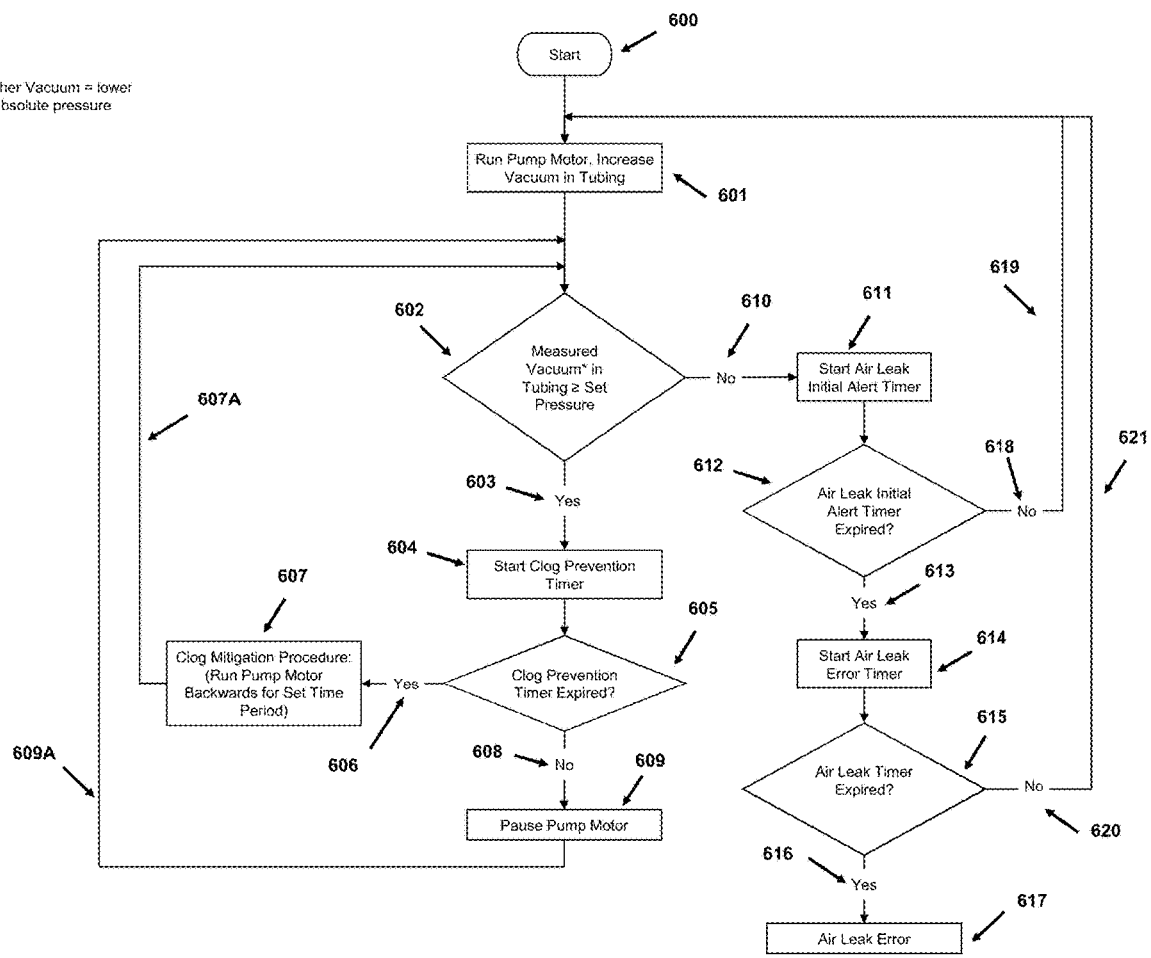
FIG. 32 is a flow chart outlining the utilization of a peristaltic pump for facilitated operations due to clogging and/or completed fluid removal considerations.

FIG. 32 depicts a flow chart as it pertains to the beneficial utilization of a peristaltic pump within the disclosed method and system. Such a depiction basically shows how certain issues during pump activity within a subject patient are easily understood, thereby permitting facilitated trouble shooting as well as ultimate quick resolution to any such problems (and efficient, cost-effective manners thereof, as well). In this situation, the system is started 600 with the pump activated and the fluid transfer line placed within a wound, whether internal or at the surface of the subject patient. The motor is then increased in terms of pressure applied 601 in order to reach the optimal level for such fluid removal. In normal operation, the system will run until the correct vacuum pressure is applied, and will periodically perform a clog detection, and mitigation routine. In such operation, the vacuum pressure is then measured to determine if such pressure has reached or increased above that of the set pressure 602. If such a pressure exceeds the set pressure 603, then a timer is set in order to reverse pressure application to dislodge a potential clog 604. The duration set is then monitored 605 such that when the full time has expired 608, then a mitigation procedure is followed 607 whereby the peristaltic pump is stopped and run in the opposite direction to determine if a clog is actually present as well as to force such a clog outwards back into the wound where it can be then subjected to higher vacuum pressures as it is brought back into the fluid transfer line (tubing) or otherwise treated through another removal procedure. If the timer has not expired 608, then the peristaltic pump motor is paused 609 as the set pressure is achieved as desired. In any event, such a clog, if present, may be detected in this manner in relation to the facilitated capability of starting, stopping, and running such a peristaltic pump in the opposite direction quickly and effectively. This allows for a clog determination easily in relation to higher vacuum pressures (lower absolute pressure applications) in reaction to such difficulties when in operation. Certainly, if the measured vacuum does not show a higher level than the set pressure from the peristaltic pump itself 610, then the user may determine if there is an air leak (or possible exhaustion of fluid to be removed) within the system. Such involves the setting of an air leak timer 611 to limit the time that the pump will try to establish the set vacuum pressure. Thus, an initial air leak timer is set and may expire 613 leading to the setting of a further air leak error timer 614 to further assess the potential for such a leak (or lack of fluid within the wound). If such a timer expires without a change 616, then an error is deduced 617, allowing for a simple rectification of the issue. If either air leak timer 611 or 614 does not expire, the pump is allowed to continue to attempt to reach the set vacuum pressure 601 and will reassess the situation as needed. In any case, again, such a peristaltic pump allows for quick reversal of pressures and thus effective and quick understanding and resolution of such potential problems within a fluid transfer line.

Figure 33:
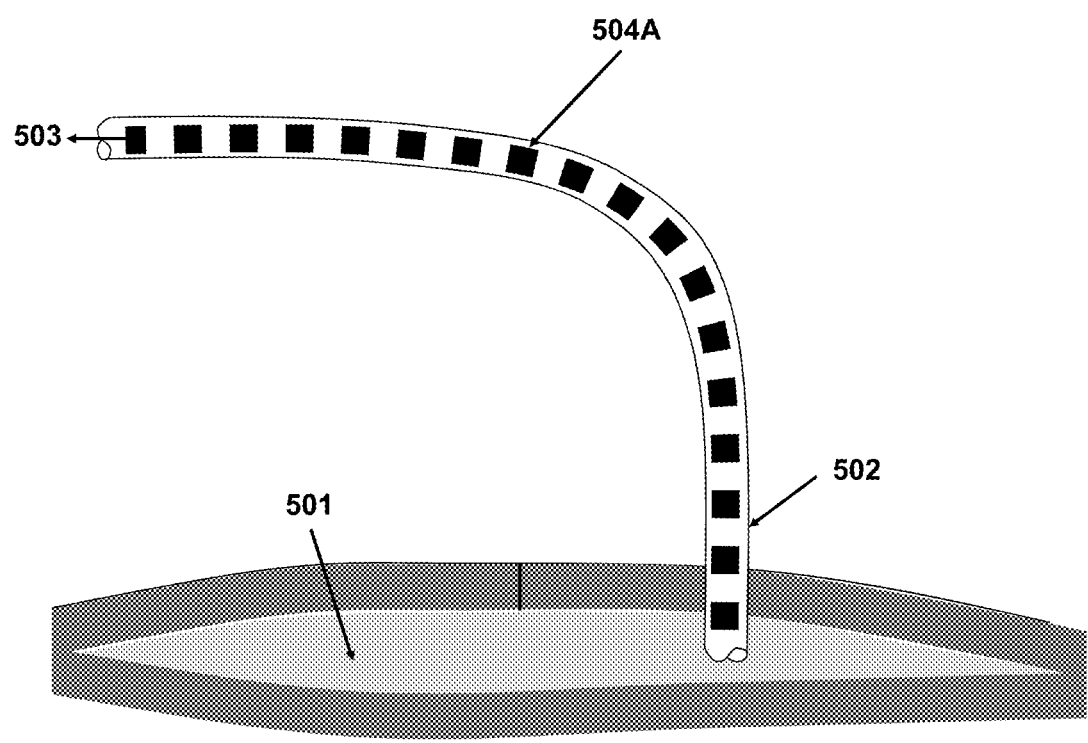
FIG. 33 is a cross-sectional side view of the application of a vacuum line with multiple fluid motion sensors therein within a deep wound/surgical site.
Figure 34:
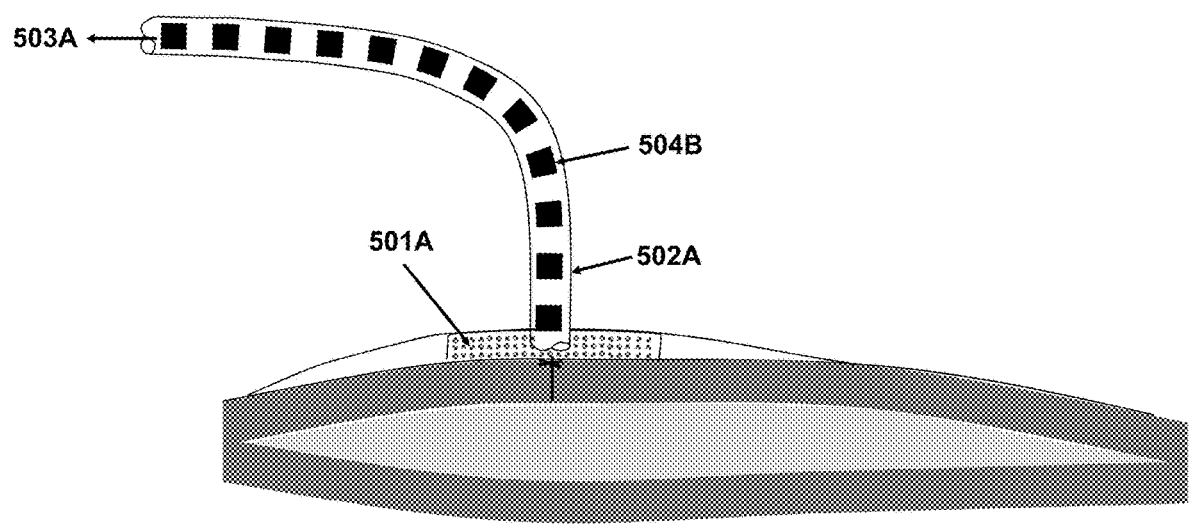
FIG. 34 is a cross-sectional side view of the application of a vacuum line with multiple fluid motion sensors therein within a surface wound/surgical site.
Figure 35:
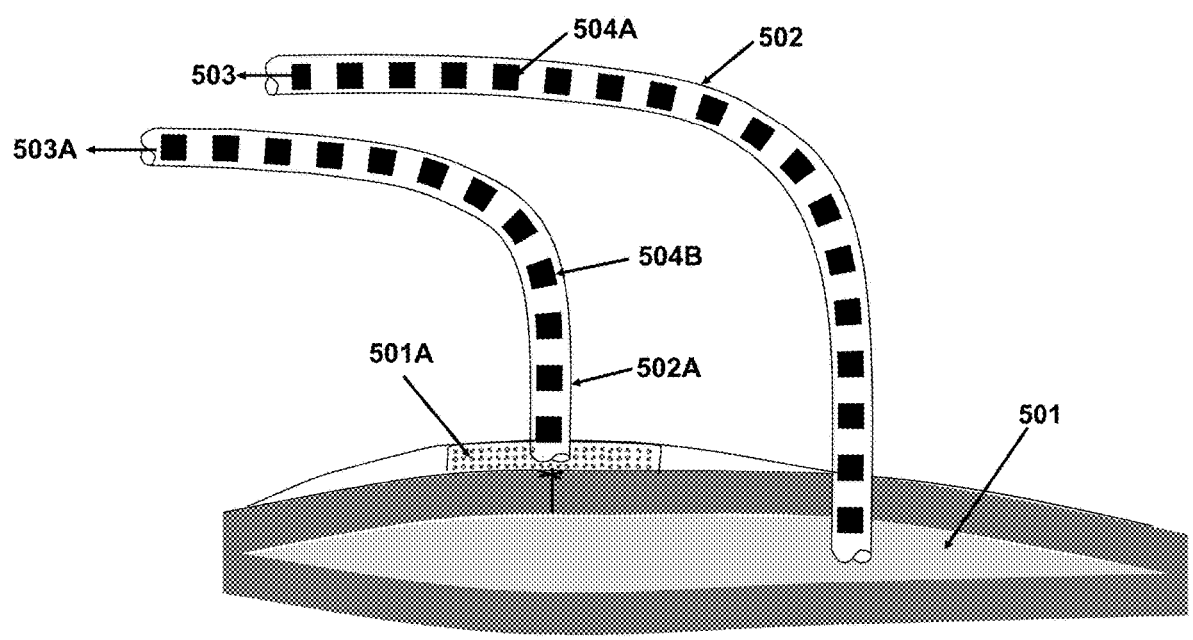
FIG. 35 is a cross-sectional side view of the application of two vacuum lines with multiple fluid motion sensors therein simultaneously within a deep wound/surgical site and a surface wound/surgical site.

FIG. 33 provides a view of a fluid transfer line 502 sensors therein 504A leading from an internal wound outwardly to an end 503 (for incorporation eventually within a pump. FIG. 34 has a similar set up with a transfer line 502A having sensors 504B, leading from a surface wound 501A to an end 503A for introduction/incorporation within a pump device. Such sensors allow for fluid transfer movement monitoring, whether in terms of speed, flow direction, viscosity, or other measured physical values. Such sensors are embedded within the transfer line tubing, here, in both situations throughout each line 502, 502A, and can send signals (such as through RFID, and the like, capabilities) to the pump device or other location on demand FIG. 35 thus shows both transfer lines 502, 502A simultaneously utilized within two separate wounds (internal 501 and surface 501A) of a subject patient, with such multiple sensors 502, 504B, within such lines 502, 502A, leading to ends 503, 503A.

Figure 36:
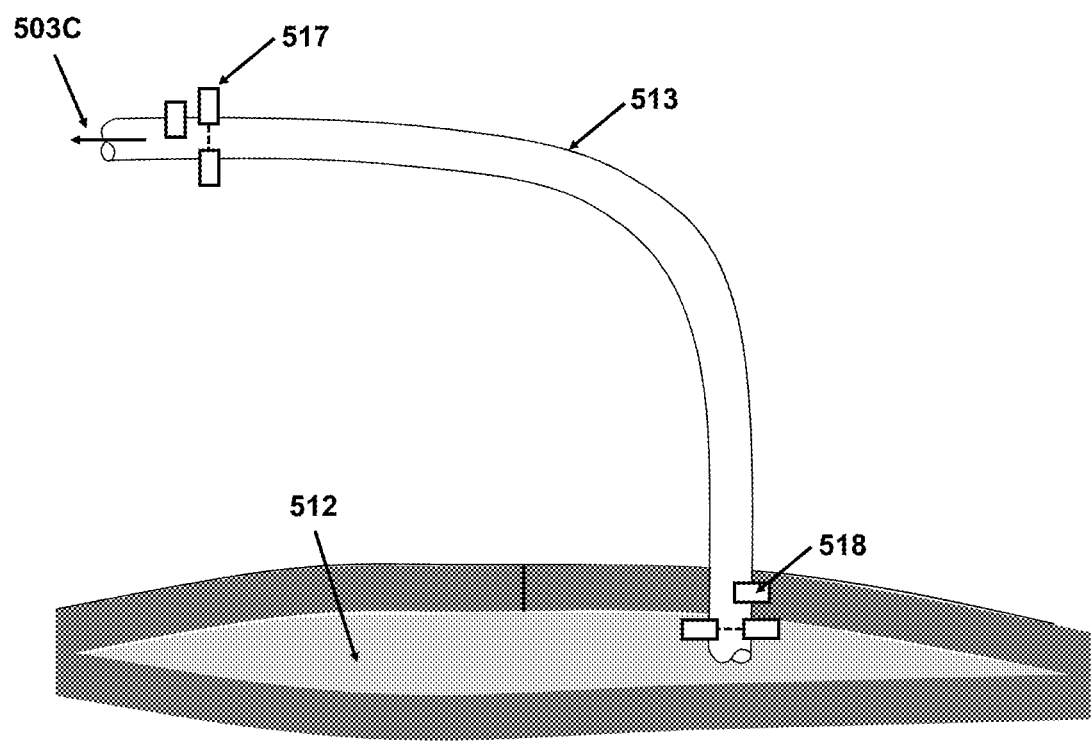
FIG. 36 is a cross-sectional side view of the application of a vacuum line with two separately situated fluid motion sensor arrays therein within a deep wound/surgical site.
Figure 37:
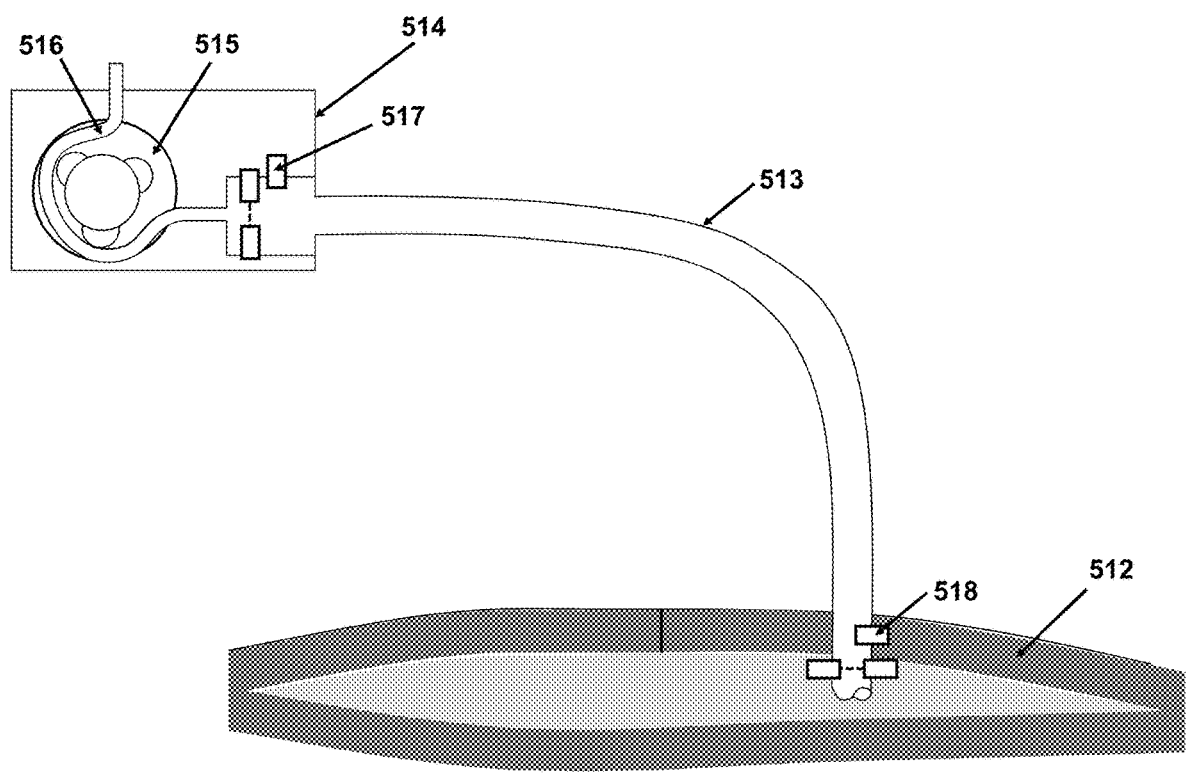
FIG. 37 is a cross-sectional side view of the application of a vacuum line with a fluid motion sensor array at the pump and a second array adjacent the fluid intake site within a line placed within a deep wound/surgical site.

FIGS. 36 and 37 show a representation of an internal wound 512 having a fluid transfer line 513 with separate types of sensors 517, 518 present on either end of such a line 513. Thus, one set 517 is adjacent an end 503C that leads to a pump 514 (FIG. 37) and the other set 518 adjacent the internal wound 512. The pump in FIG. 37 is presented as a peristaltic type with a revolving disc 515 and the vacuum tubing 516 therein. Such sensors 517, 518 thus assess certain physical characteristics of the fluid as it moves from the wound 512 to the pump 516, as noted above, without the need for more throughout the entirety of the fluid line (as in FIGS. 33-35, above).

Figure 38:
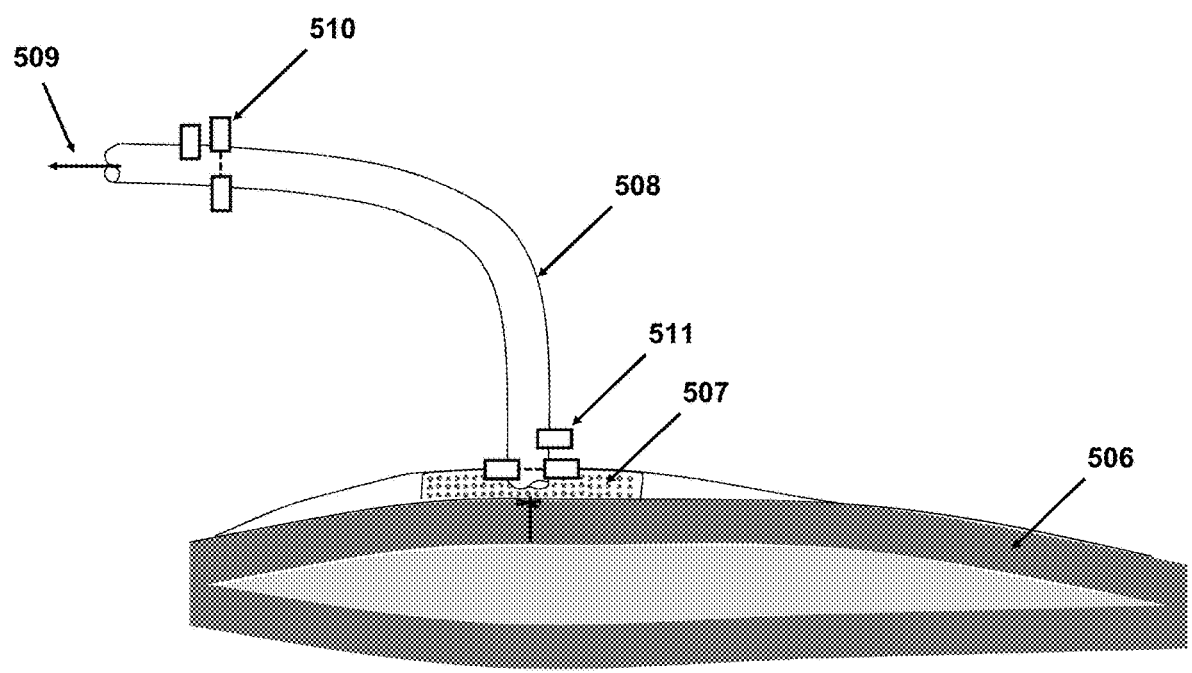
FIG. 38 is a cross-sectional side view of the application of a vacuum line with two separately situated fluid motion sensor arrays therein within a surface wound/surgical site.
Figure 40:
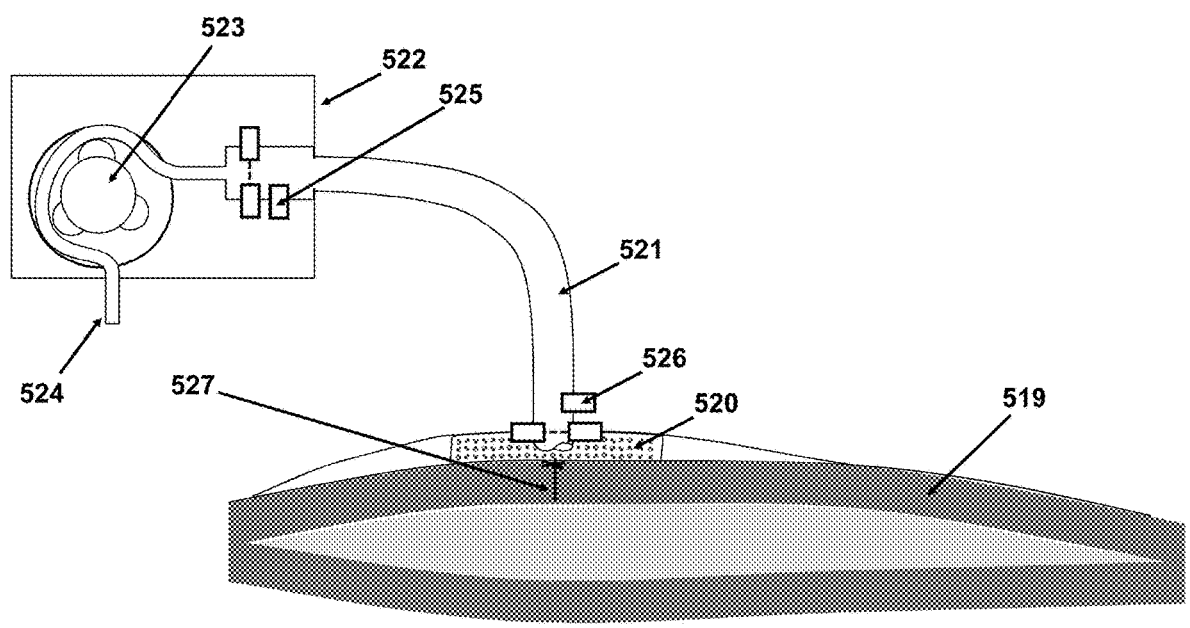
FIG. 40 is a cross-sectional side view of the application of a vacuum line with a fluid motion sensor array at the pump and a second array adjacent the fluid intake site within a line placed within a surface wound/surgical site.

FIG. 38 thus shows a representation of a surface wound 507 having a fluid transfer line 508 leading to an end 509 leading to a pump (such as 522 of FIG. 40). Sensor groups 510, 511 are present as in FIGS. 36, and 37 at the ends adjacent the pump 509 and adjacent the surface wound 507 on a patient's body 506. FIG. 40 shows a surface wound 520 with an incision 527 therebelow on the subject patient's body 519. As with FIG. 38, a transfer line 521 includes two groups of sensors 525, 526 with one 525 at the pump end 522 (the pump having a disc 523 and tubing 524) and a wound end 526.

Figure 39:
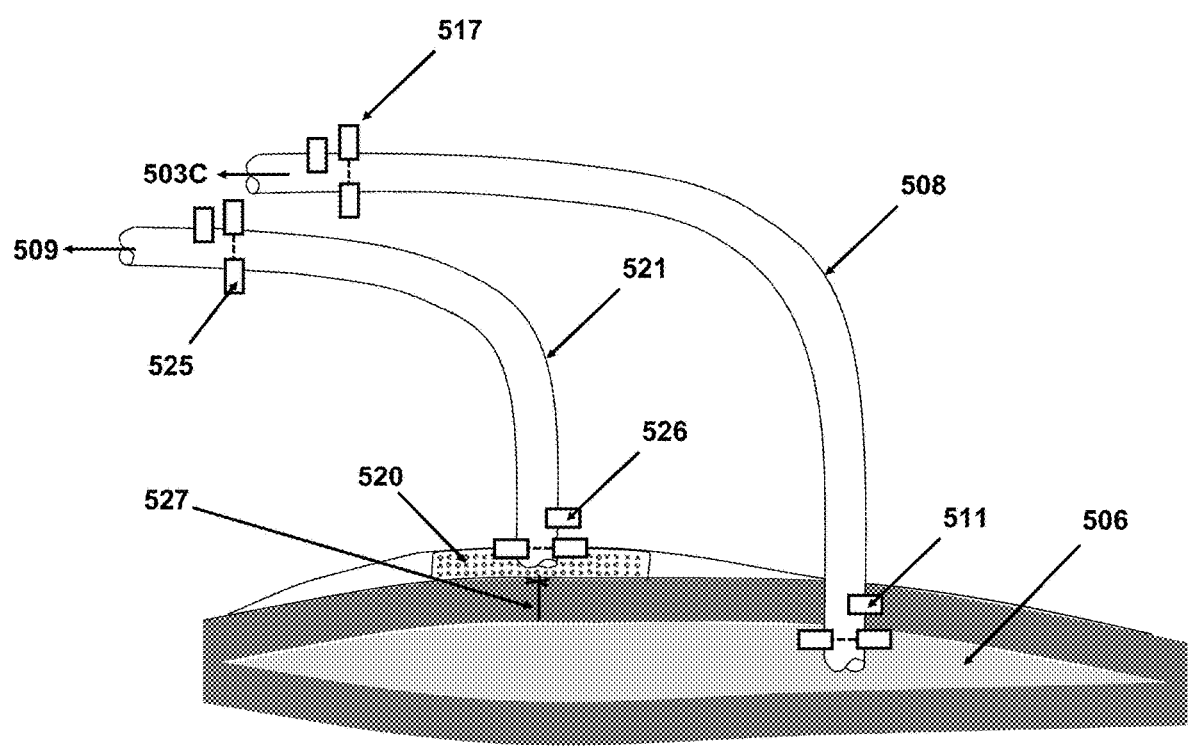
FIG. 39 is a cross-sectional side view of the application of two vacuum lines with two separate fluid motion sensor arrays present therein simultaneously within a deep wound/surgical site and a surface wound/surgical site.
Figure 41:
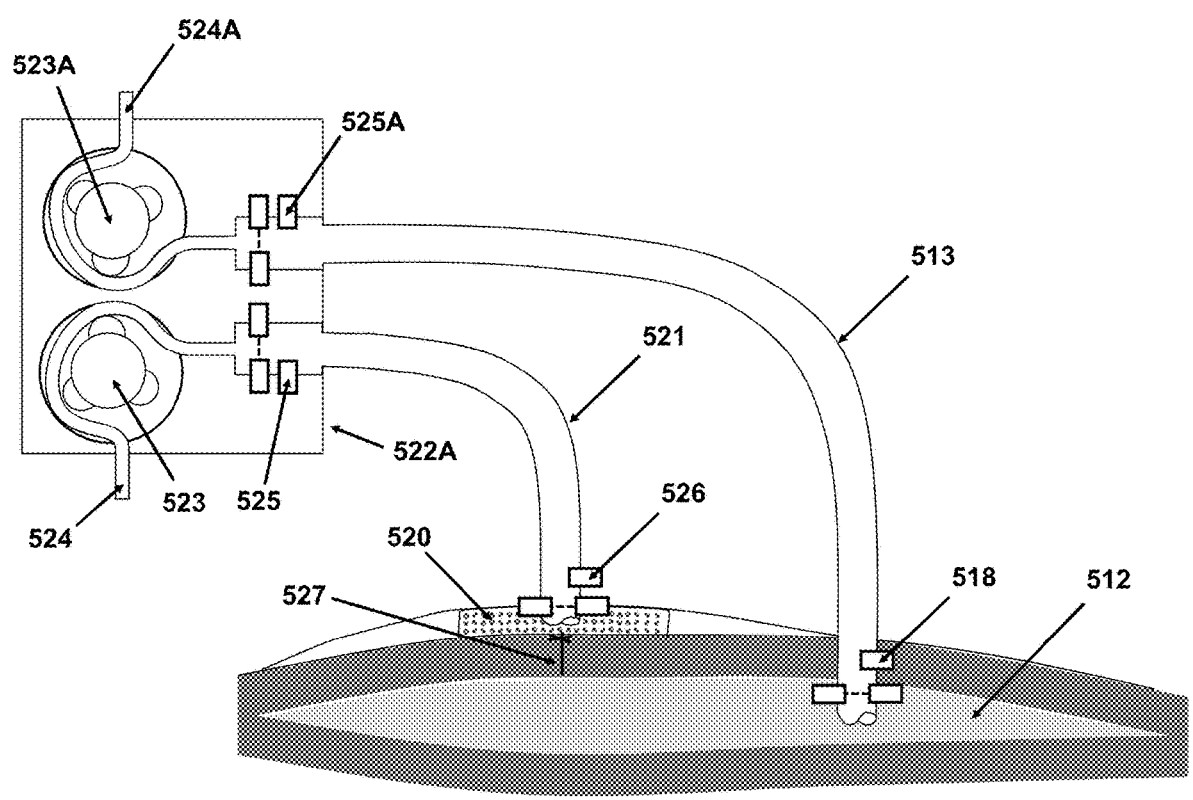
FIG. 41 is a cross-sectional side view of the application of two separate vacuum lines attached to two separate peristaltic pumps with a fluid motion sensor array at each pump and a second array adjacent the fluid intake site within a line placed within a wound/surgical sit, with one being a deep site and the other a surface site.

FIG. 39 provides a simultaneous utilization of two transfer lines 508, 521, with one 508 leading to an internal wound 506 and the other 521 to a surface wound 520 with a lower incision 527. Both lines 508, 521, have the same groups of sensors 511, 526 adjacent the wounds 506, 520, as well as groups of sensors 517, 525 adjacent the pump ends 503C, 509. FIG. 41 shows a similar representation as FIG. 39 with two separate peristaltic pumps 523, 523A, 524, 524A utilized for fluid removal. The internal wound 512 has a line 513 applied thereto with a wound-adjacent sensor group 518 and a pump-adjacent sensor group 525A, and the surface wound 520, 527 has a line 521 with a wound-adjacent sensor group 526 and a pump-adjacent group 525. Such allows for monitoring purposes as well as simultaneous fluid removal for the same patient from two separate types of wounds (whether caused by accident, surgery, or other type of situation).

Figure 42:
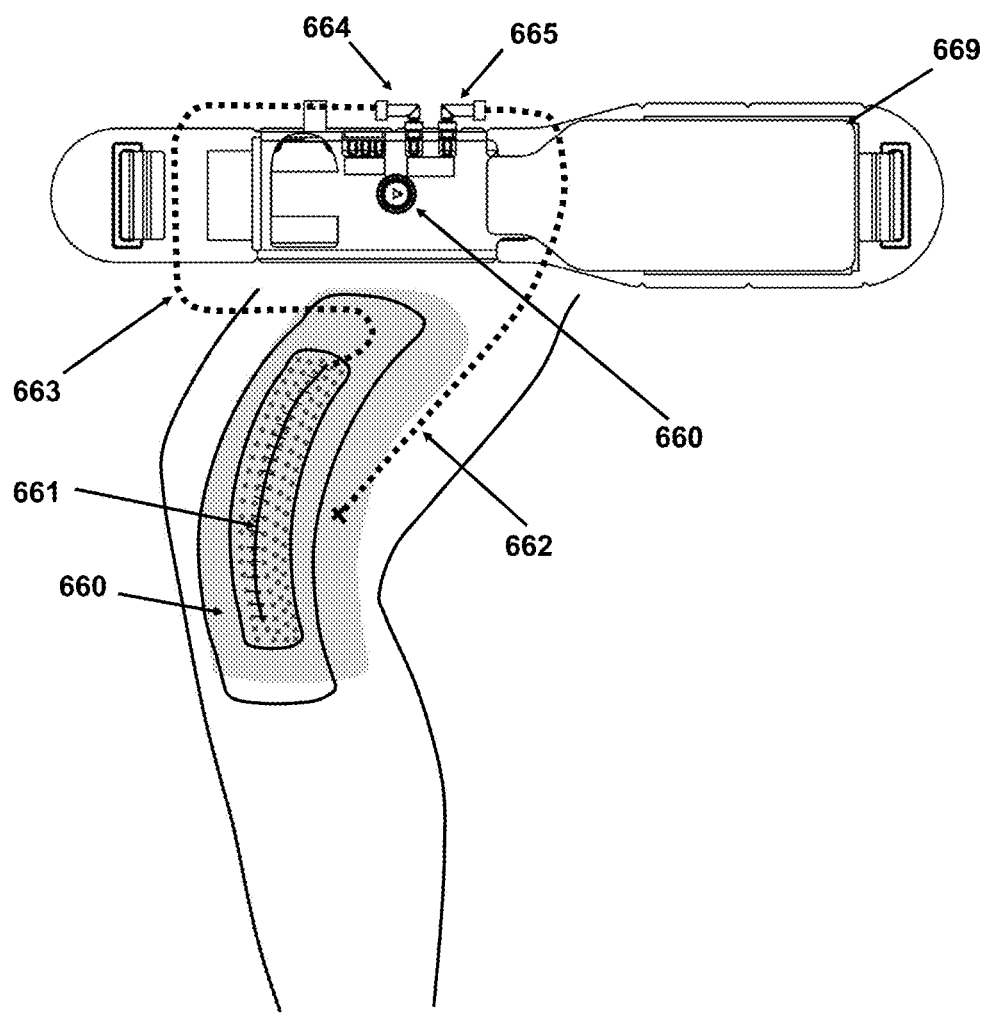
FIG. 42 is a view of a complete belt/peristaltic pump device with fluid removal lines leading to a patient's surface knee wound and deep wound simultaneously.
Figure 43:
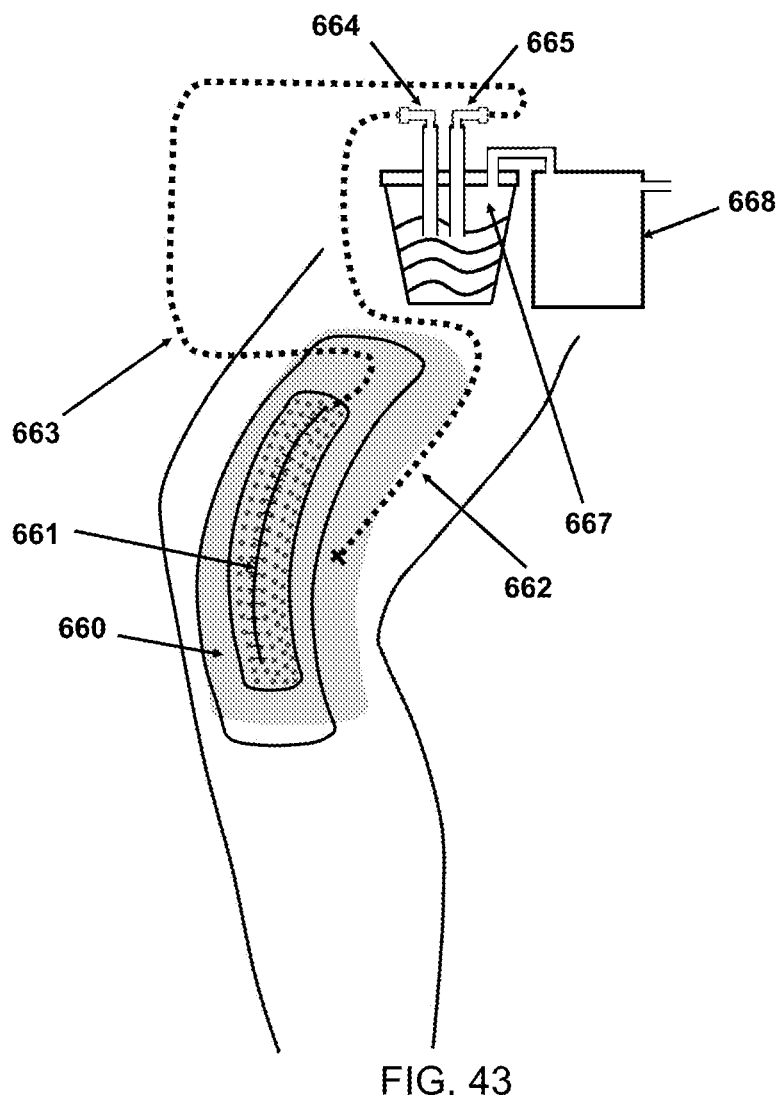
FIG. 43 is a view of a complete belt/air pump device with fluid removal lines leading to a patient's surface knee wound and deep wound simultaneously.
Figure 44:
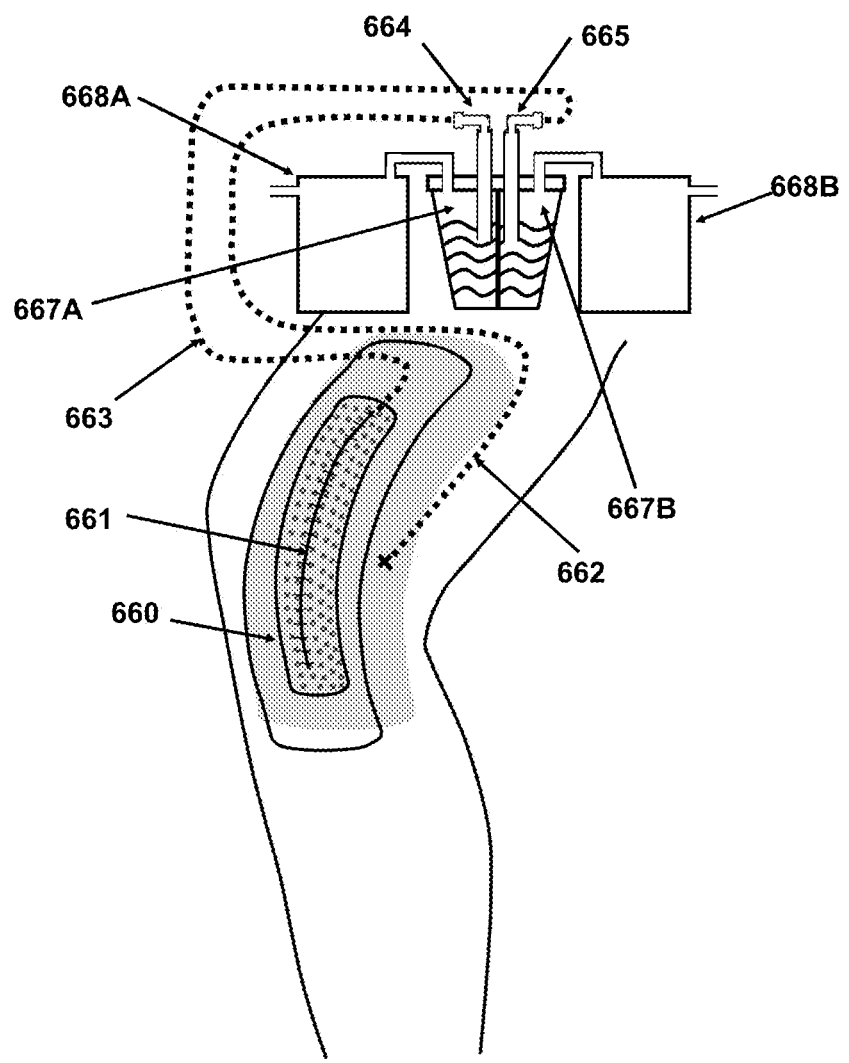
FIG. 44 is a view of a complete belt/double air pump device with fluid removal lines leading to a patient's surface knee wound and deep wound simultaneously.

FIGS. 42-44 show the utilization of a single type of pump with simultaneous drainage of two different wounds on a patient's leg/knee area. FIG. 42 shows a peristaltic pump device 660 with a collection component 669 and two separate ports 664, 665 leading to two separate fluid removal/transfer lines 662, 663 for such a purpose. One line 662 leads to a surface wound 661 and the other line 663 leads to an internal wound 660. FIG. 43 is basically the same as if FIG. 42, but the pump device 667 is a hydraulic vacuum with a collection tank 668. FIG. 44 shows two separated hydraulic pumps 667A, 667B, with two separate collection tanks 668A, 668B that accords the same simultaneous capabilities for fluid removal from a subject patient. Of course, as noted above, such simultaneous wound fluid removal is not limited to one surface wound and one internal wound, as more than two wounds may be treated with such pump devices and transfer lines (as many as feasible as shown and described below) and such wounds may be of any type (any number of surface wounds and any number of internal wounds).

Figure 45:
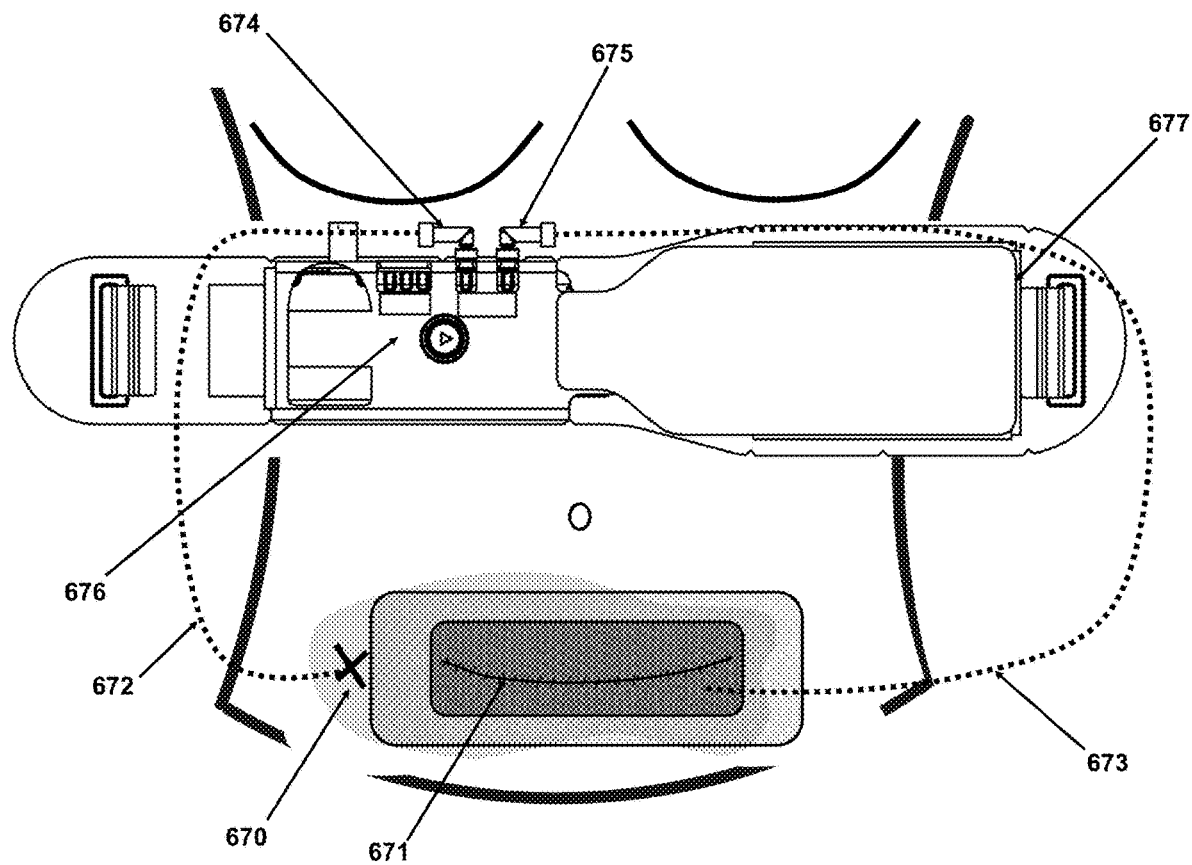
FIG. 45 is a view of a complete belt/peristaltic pump device with fluid removal lines leading to a patient's surface abdominal wound and deep wound simultaneously.
Figure 46:
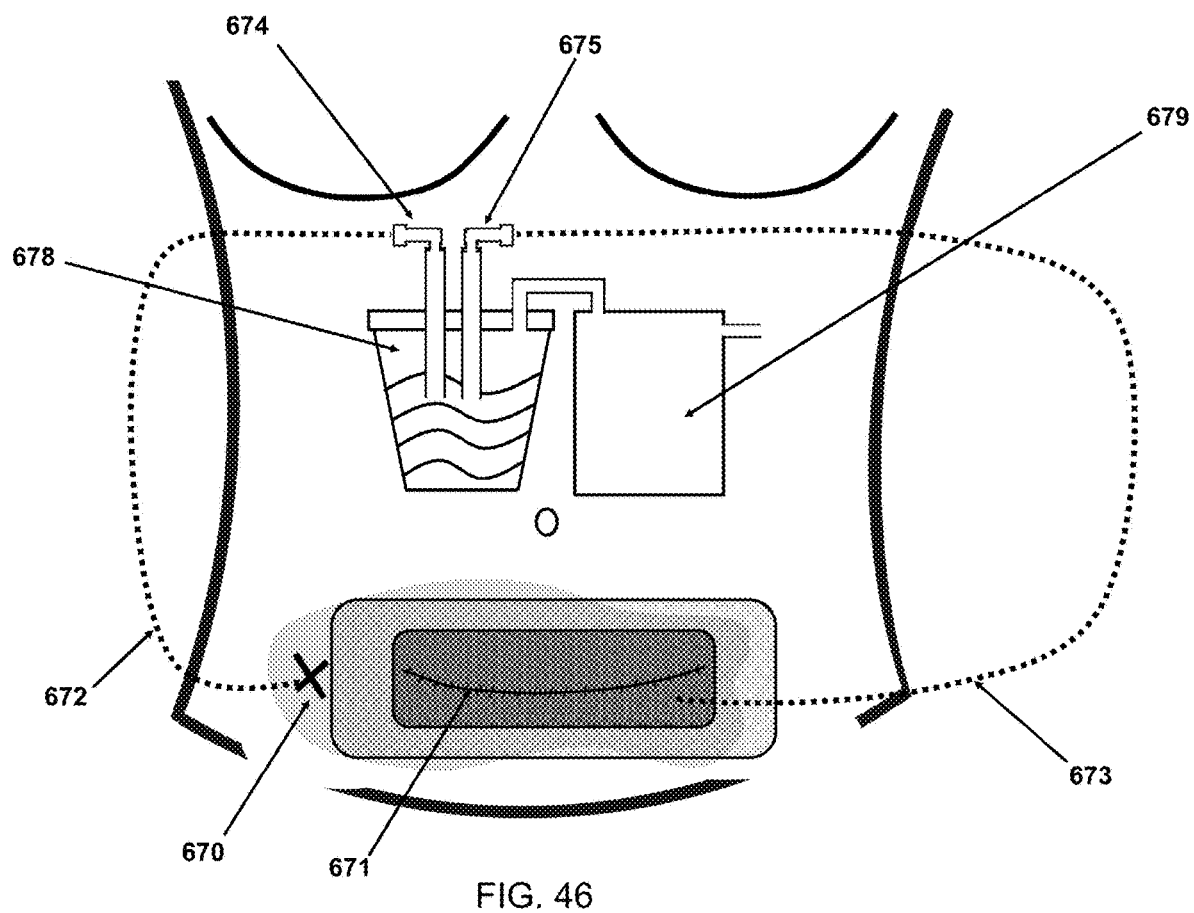
FIG. 46 is a view of a complete belt/air pump device with fluid removal lines leading to a patient's surface abdominal wound and deep wound simultaneously.
Figure 47:
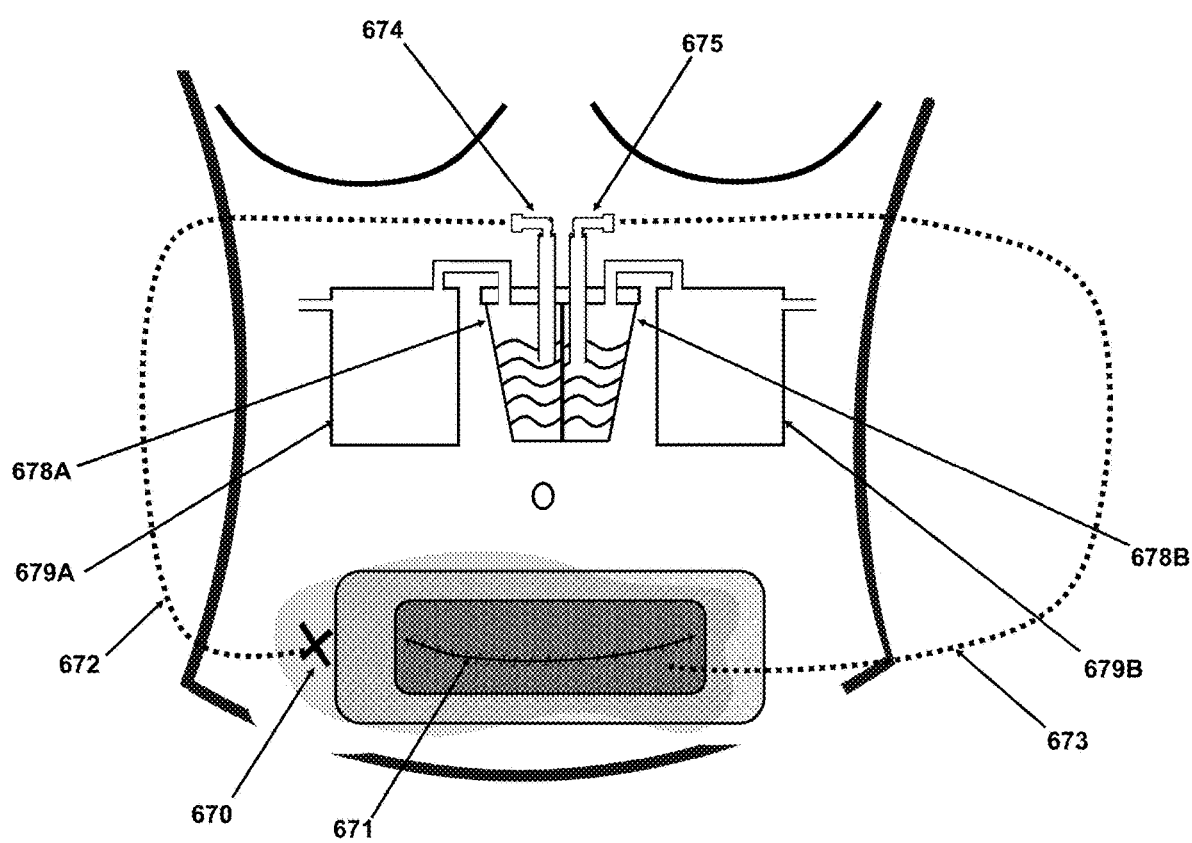
FIG. 47 is a view of a complete belt/double air pump device with fluid removal lines leading to a patient's surface abdominal wound and deep wound simultaneously.

FIGS. 45-47 depict the simultaneous fluid removal operation of a single pump device for drainage of a surface and internal wound on a single patient's abdomen. FIG. 45 shows a peristaltic pump device 676 with a collection component 677 and two separate ports 674, 675 leading to two separate fluid removal/transfer lines 672, 673 for such a purpose. One line 673 leads to a surface wound 671 and the other line 672 leads to an internal wound 670. FIG. 46 is basically the same as if FIG. 42, but the pump device 678 is a hydraulic vacuum with a collection tank 679. FIG. 44 shows two separated hydraulic pumps 678A, 678B, with two separate collection tanks 679A, 679B that accords the same simultaneous capabilities for fluid removal from a subject patient.

Figure 48:
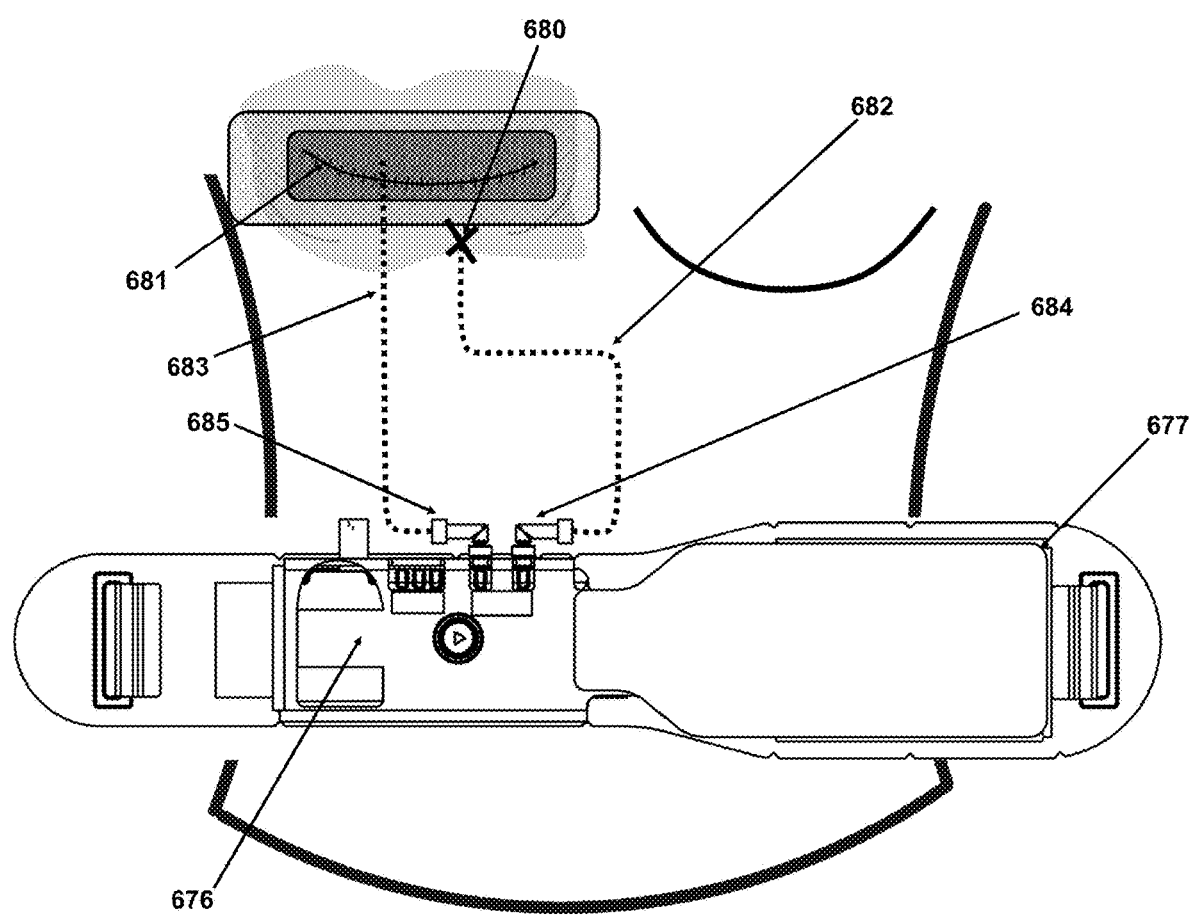
FIG. 48 is a view of a complete belt/peristaltic pump device with fluid removal lines leading to a patient's surface mastectomy wound and deep wound simultaneously.
Figure 49:
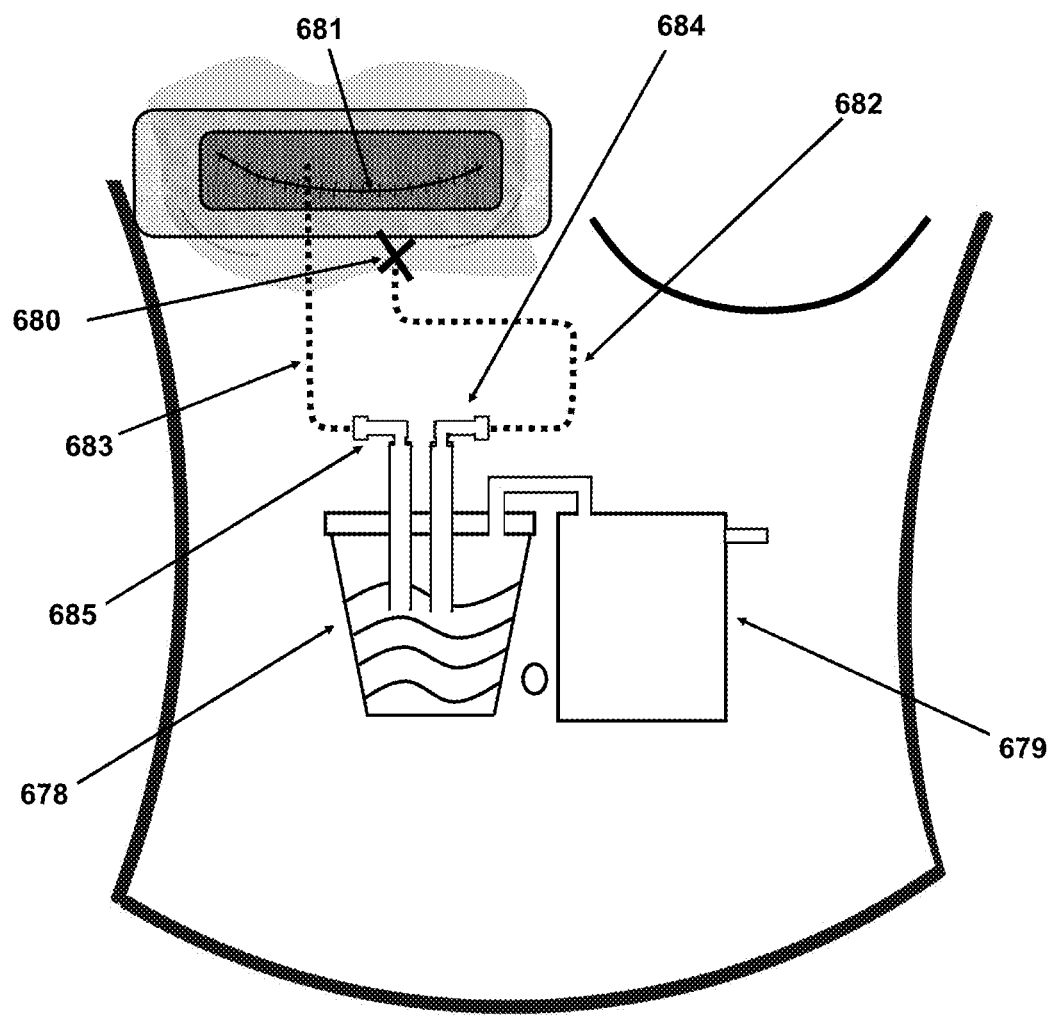
FIG. 49 is a view of a complete belt/air pump device with fluid removal lines leading to a patient's surface mastectomy wound and deep wound simultaneously.
Figure 50:
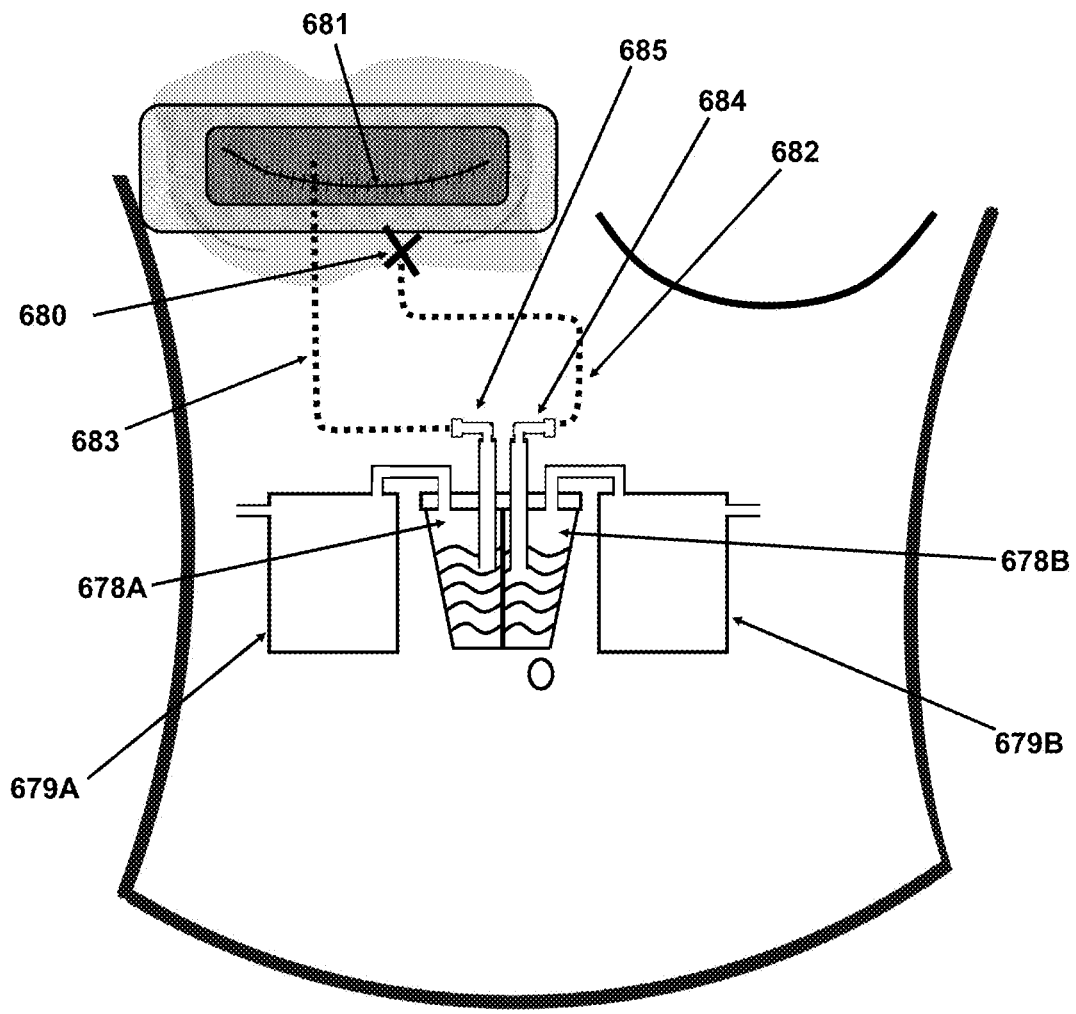
FIG. 50 is a view of a complete belt/double air pump device with fluid removal lines leading to a patient's surface mastectomy wound and deep wound simultaneously.

FIGS. 48-50 show the utilization of a single type of pump with simultaneous drainage of two different wounds on a mastectomy patient. FIG. 48 shows a peristaltic pump device 676 with a collection component 677 and two separate ports 684, 685 leading to two separate fluid removal/transfer lines 682, 683 for such a purpose. One line 683 leads to a surface wound 681 and the other line 682 leads to an internal wound 680. FIG. 49 is basically the same as FIG. 48, but the pump device 678 is a hydraulic vacuum with a collection tank 679. FIG. 50 shows two separated hydraulic pumps 678A, 678B, with two separate collection tanks 679A, 679B that accords the same simultaneous capabilities for fluid removal from the subject mastectomy patient.

Figure 51:
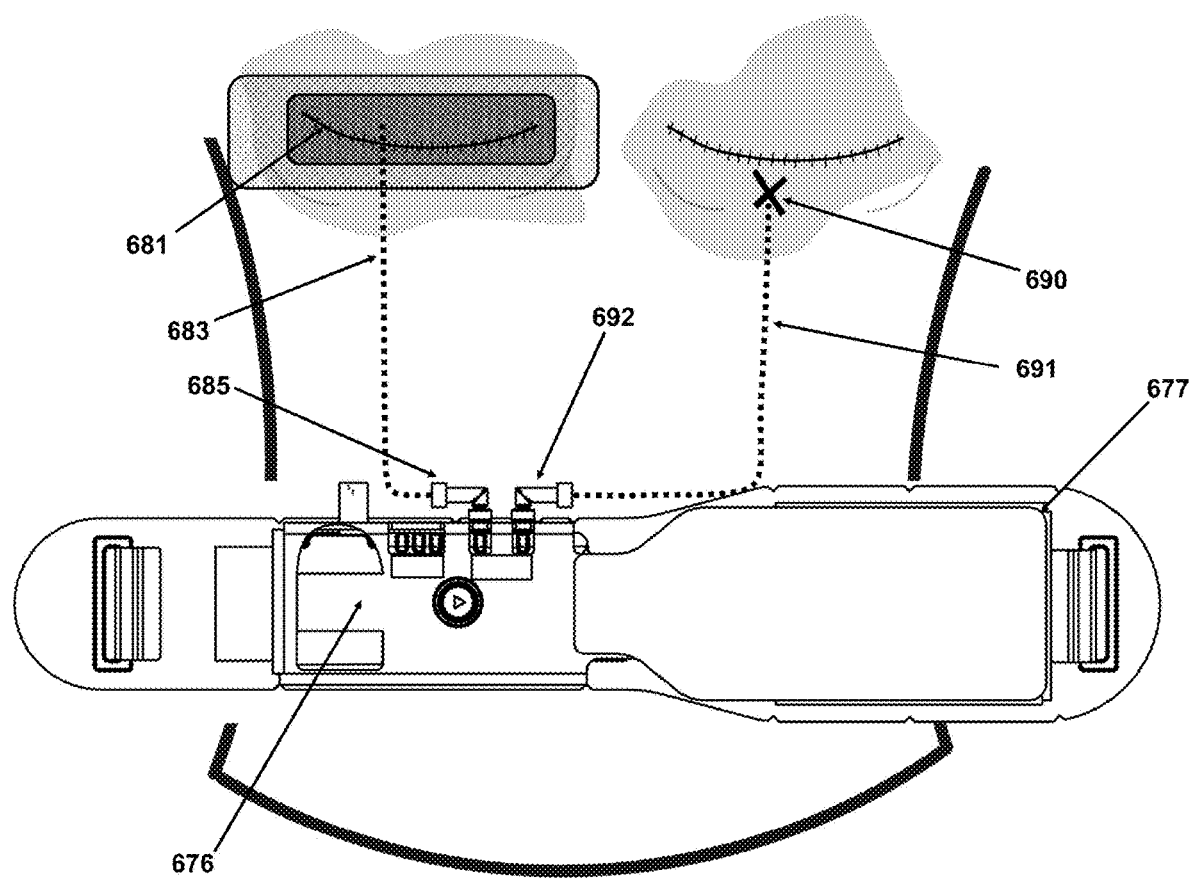
FIG. 51 is a view of a complete belt/peristaltic pump device with fluid removal lines leading to a patient's surface mastectomy wound and an opposing breast deep wound simultaneously.
Figure 52:
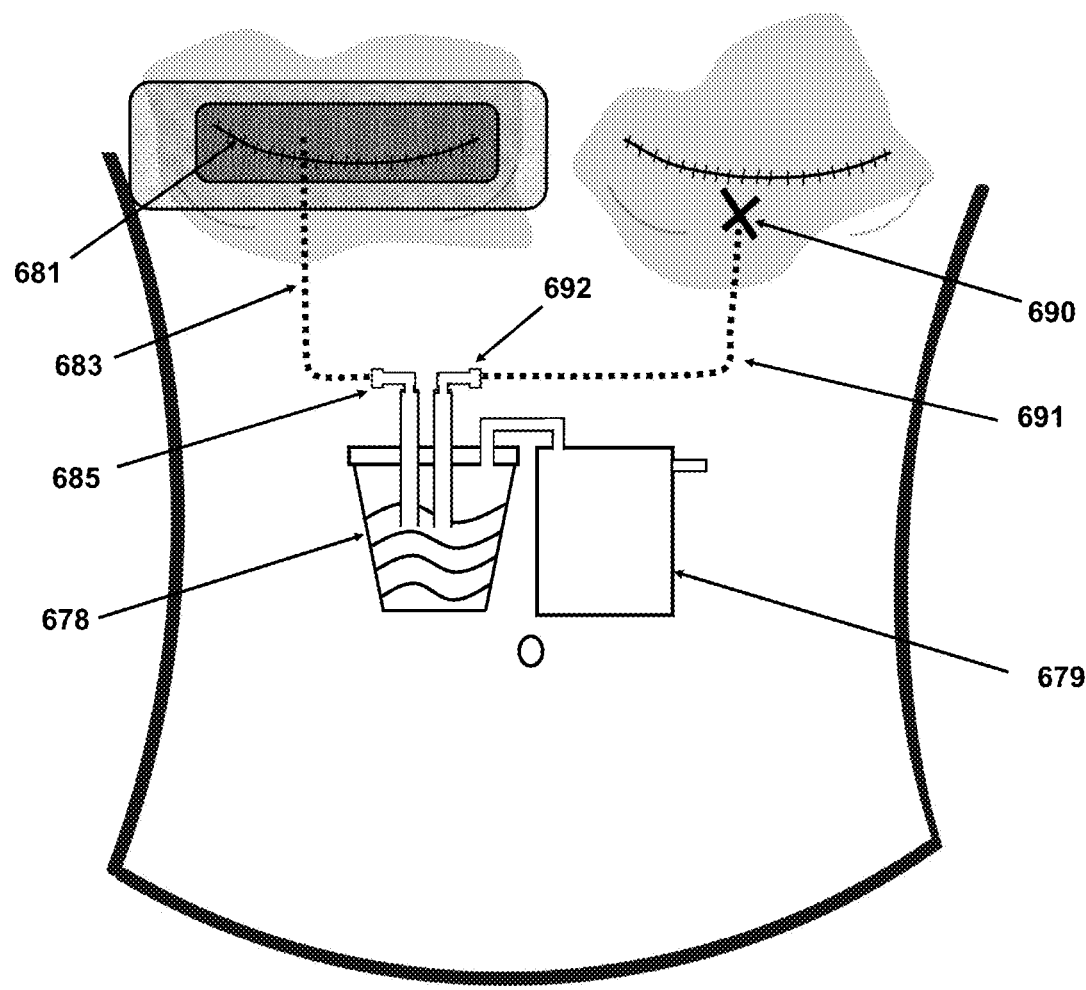
FIG. 52 is a view of a complete belt/air pump device with fluid removal lines leading to a patient's surface mastectomy wound and an opposing breast deep wound simultaneously.
Figure 53:
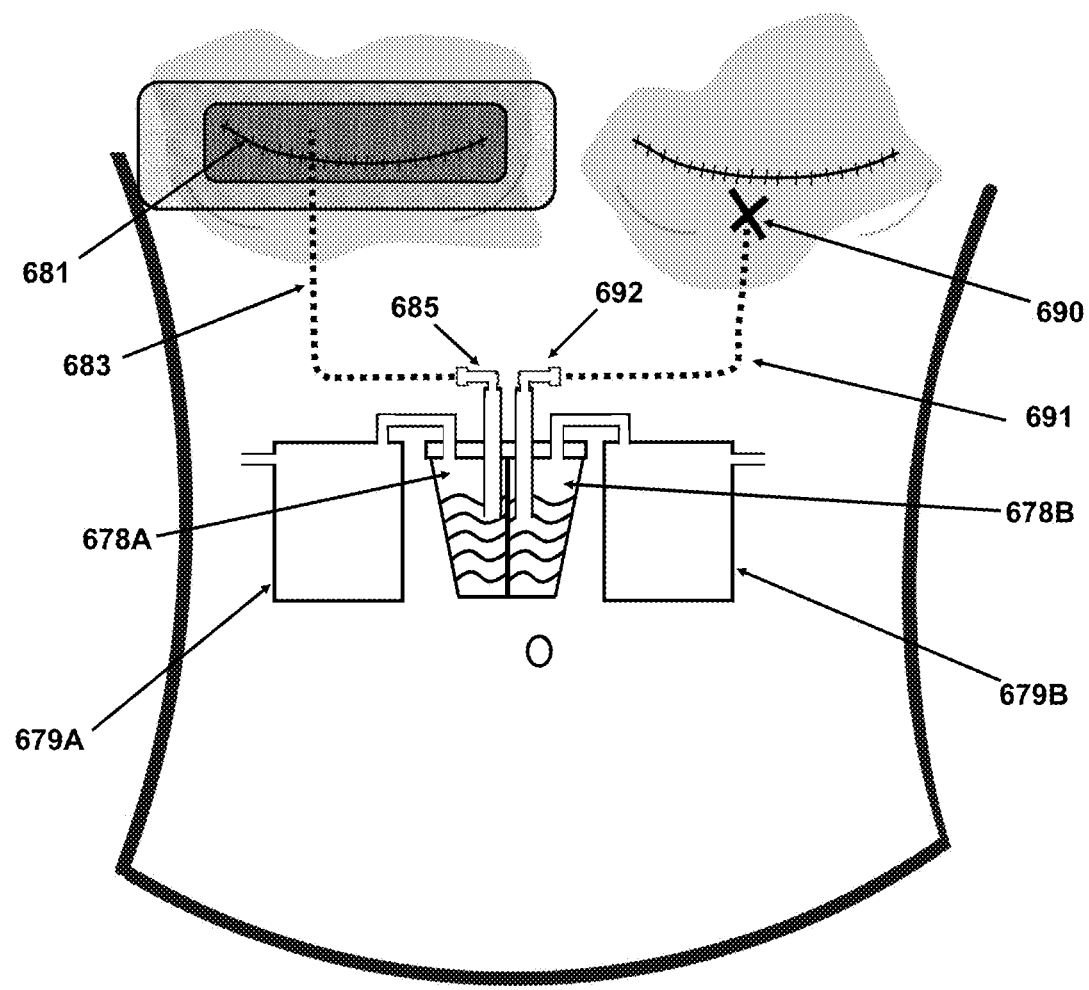
FIG. 53 is a view of a complete belt/double air pump device with fluid removal lines leading to a patient's surface mastectomy wound and an opposing breast deep wound simultaneously.

FIGS. 51-53 show the utilization of a single type of pump with simultaneous drainage of two different wounds on a mastectomy patient, in this situation with one wound a surface type on one side of the patient's torso and the other an internal wound on the opposite side thereof. FIG. 51 shows a peristaltic pump device 676 with a collection component 677 and two separate ports 684, 692 leading to two separate fluid removal/transfer lines 682, 691 for such a purpose. One line 683 leads to the aforementioned surface wound 681 (on the facing right side) and the other line 691 leads to the aforementioned internal wound 690 (on the opposing facing left side). FIG. 52 is basically the same as FIG. 51, but the pump device 678 is a hydraulic vacuum with a collection tank 679. FIG. 53 shows two separated hydraulic pumps 678A, 678B, with two separate collection tanks 679A, 679B that accords the same simultaneous capabilities for fluid removal from opposing wound sites of the subject mastectomy patient. As alluded to above, such wounds may be two surface wounds or two internal wounds (as well as any combinations with other types of wounds in different areas/regions of the same patient), if necessary.

Figure 54:
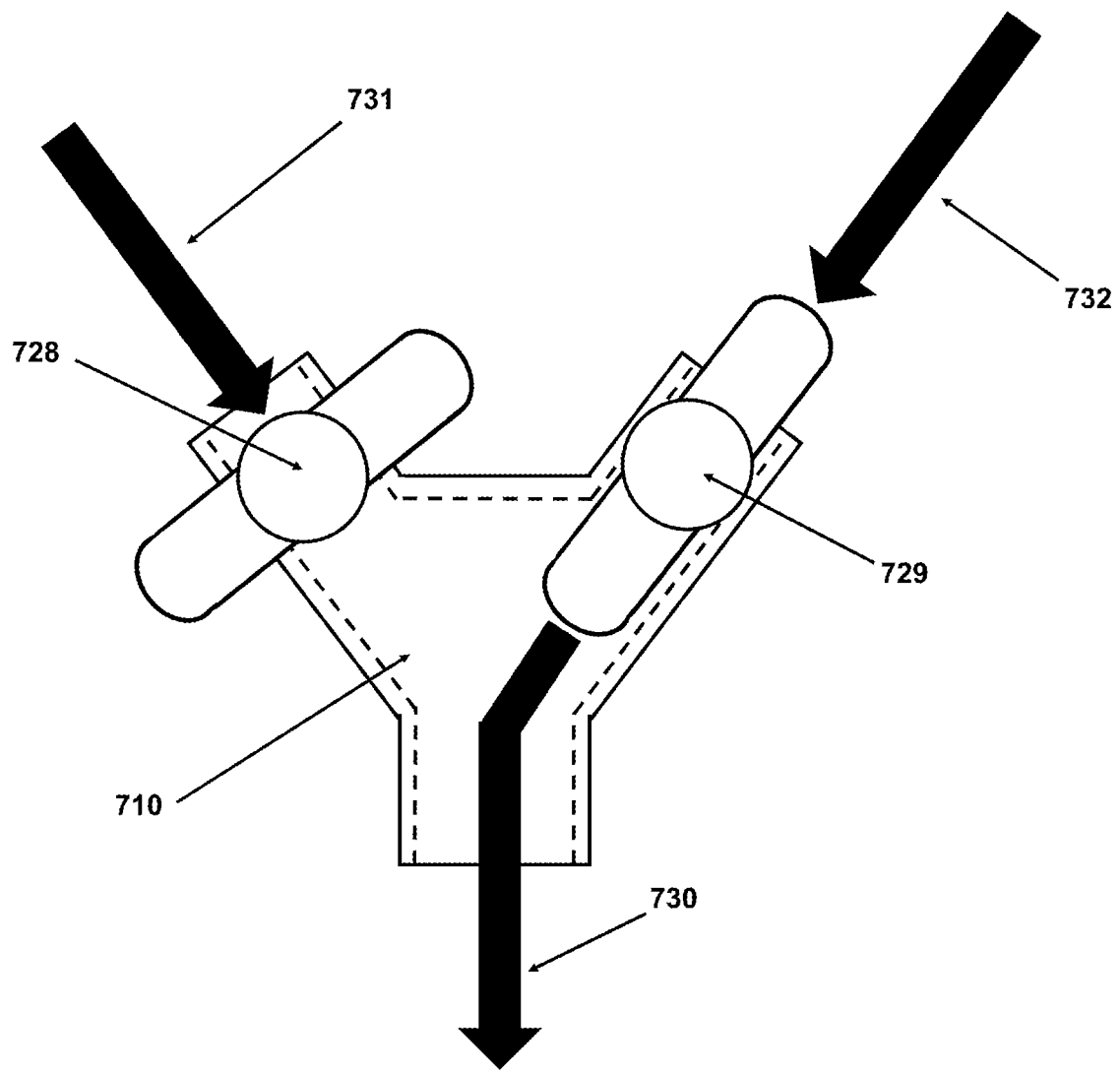
FIG. 54 is a side view of a stop cock adapter module for attachment between two fluid removal lines into a single transfer line.

FIG. 54 shows a means, as an example, of allowing for more than one transfer line leading from a wound site to a pump device. Here, a diverter is shown with the ability to direct a flow from a first line 731 and a second line 732 into a single manifold 710 for a combined line 730 that may lead to a pump. The user may divert flow from either or leave both open as desired for continuous flow from both lines 731, 732 through the utilization of a valve/stopcock 728, 729 on demand Again, this allows for more transfer lines to be utilized than just two per pump device. More than one such diverter may be employed, as well, to increase the transfer line number even more, as desired.

Figure 55:
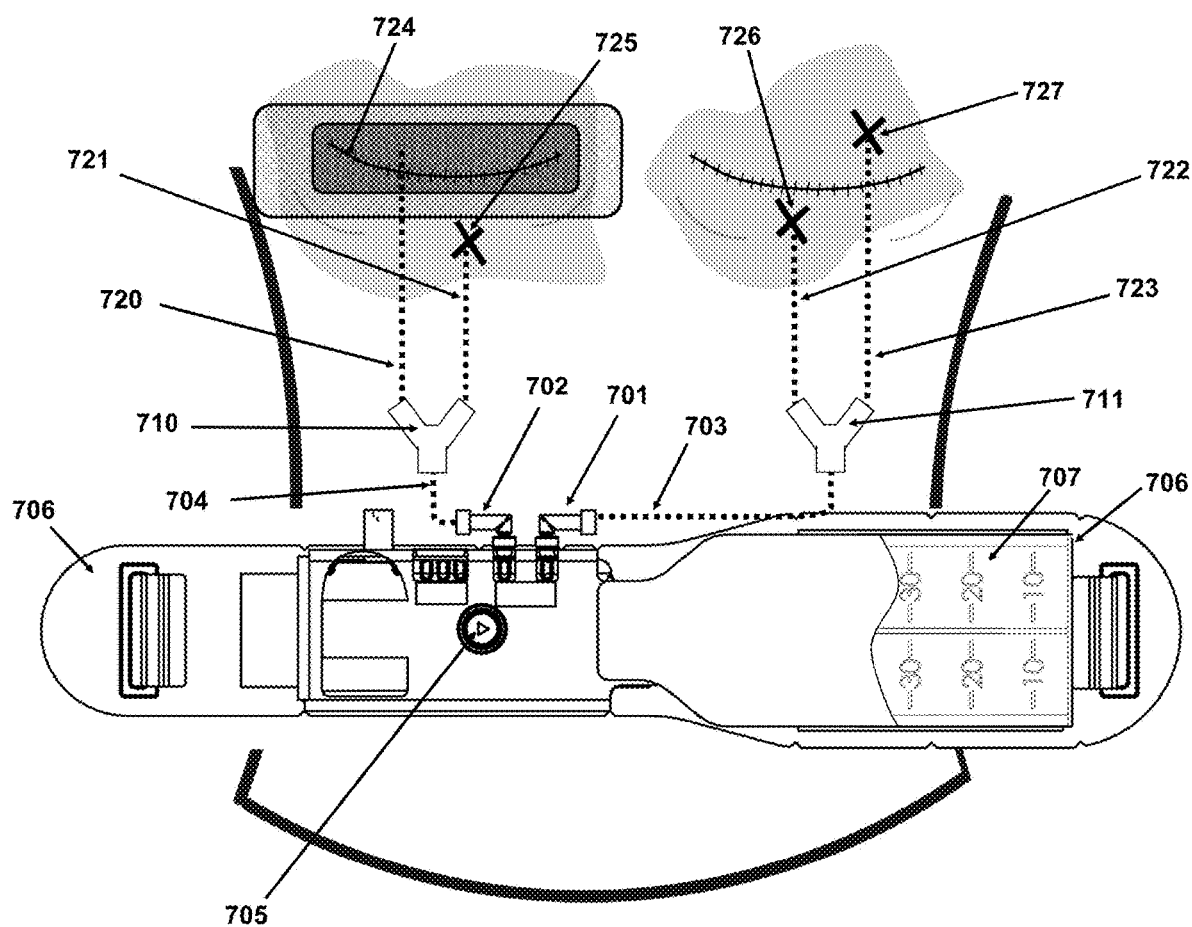
FIG. 55 is a view of a complete belt/peristaltic pump device with two separate adapters as in FIG. 54 allowing for multiple fluid removal lines leading to a patient's surface mastectomy and wound and deep wound simultaneously within one breast and two deep wounds within the other breast.
Figure 57:
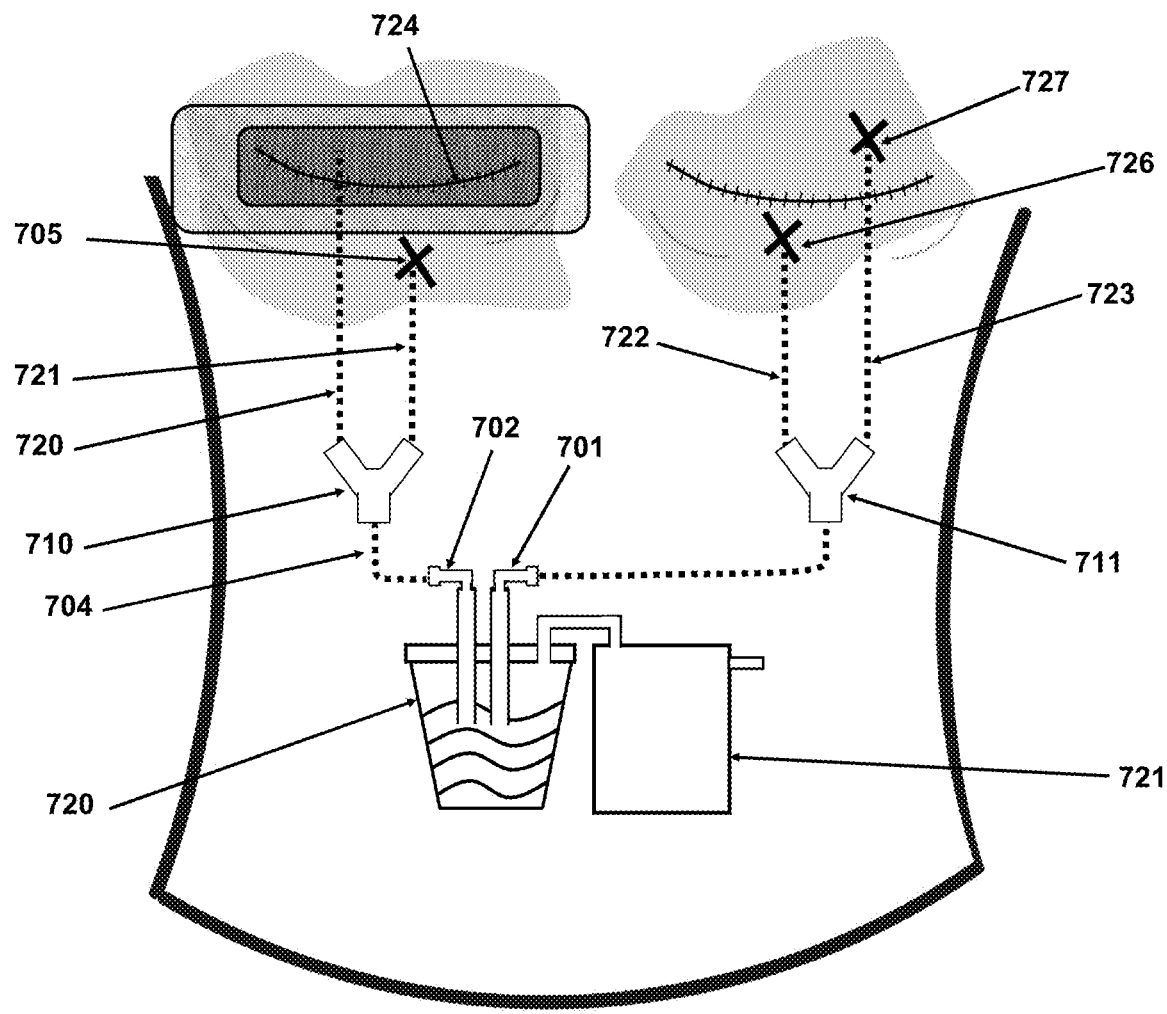
FIG. 57 is a view of a complete belt/air pump device with two separate adapters as in FIG. 54 allowing for multiple fluid removal lines leading to a patient's surface mastectomy and wound and deep wound simultaneously within one breast and two deep wounds within the other breast.
Figure 58:
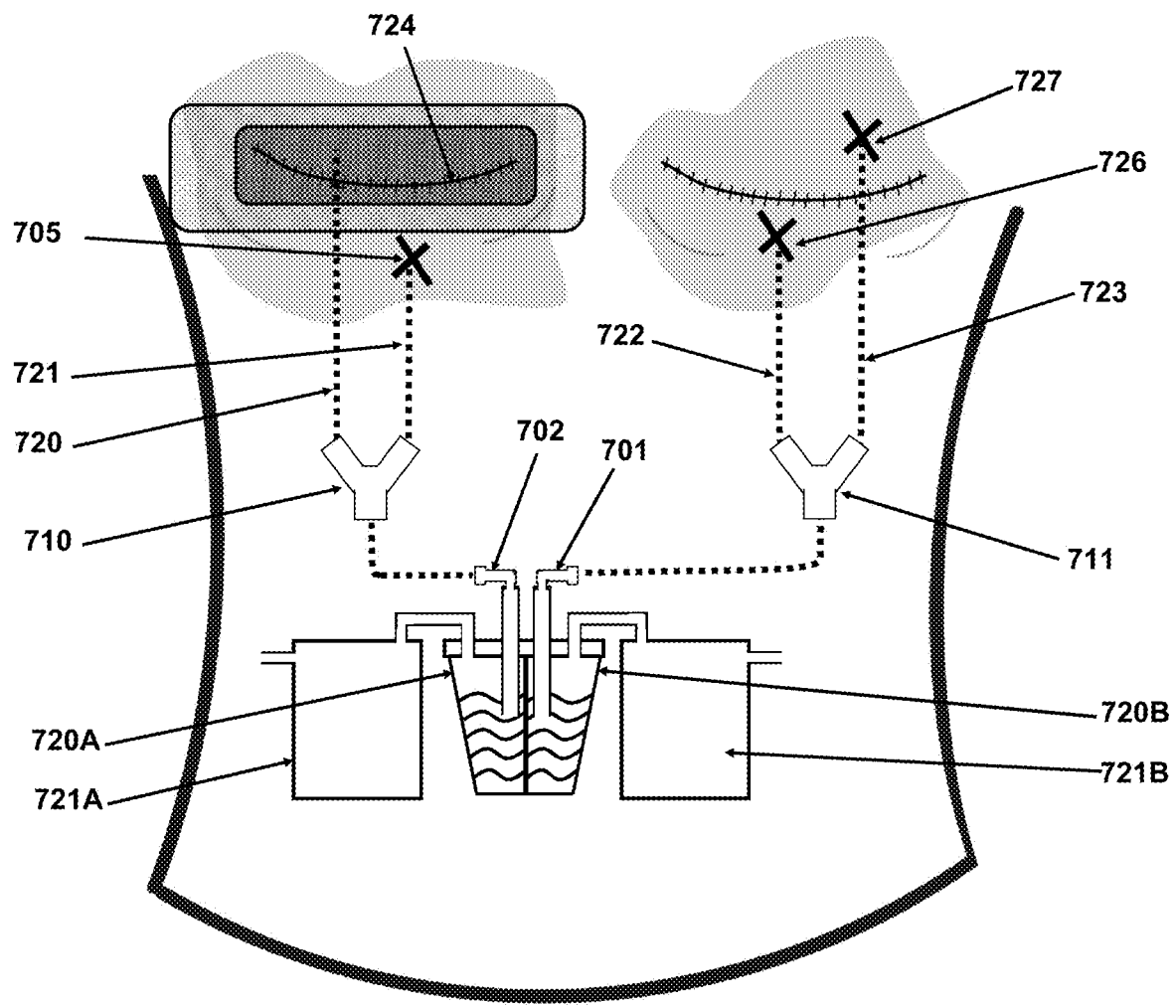
FIG. 58 is a view of a complete belt/double air pump device with two separate adapters as in FIG. 54 allowing for multiple fluid removal lines leading to a patient's surface mastectomy and wound and deep wound simultaneously within one breast and two deep wounds within the other breast.

FIGS. 55, 57 and 58 show the utilization of a single type of pump with simultaneous drainage of four different wounds on a mastectomy patient. FIG. 55 shows a peristaltic pump device 705 with a collection component 706 having gradations 707 for fluid measurement purposes and two separate ports 701, 702 leading to two separate fluid removal/transfer lines 703, 704. One line 703 leads to a diverter 711 that leads to two further transfer lines 722, 723 that lead to two separate internal wounds 726, 727 on the facing right side of the subject patient's torso. The other line 704 leads to a second diverter 710 that leads to two other lines 720, 721 that lead to another internal wound 725 and a surface wound 724, both on the left facing side of the patient's torso. FIG. 57 is basically the same as FIG. 55, but the pump device 720 is a hydraulic vacuum with a collection tank 721. FIG. 58 shows two separated hydraulic pumps 720A, 720B, with two separate collection tanks 721A, 721B that accords the same simultaneous capabilities for fluid removal from the four different wounds of the subject mastectomy patient.

Figure 56:
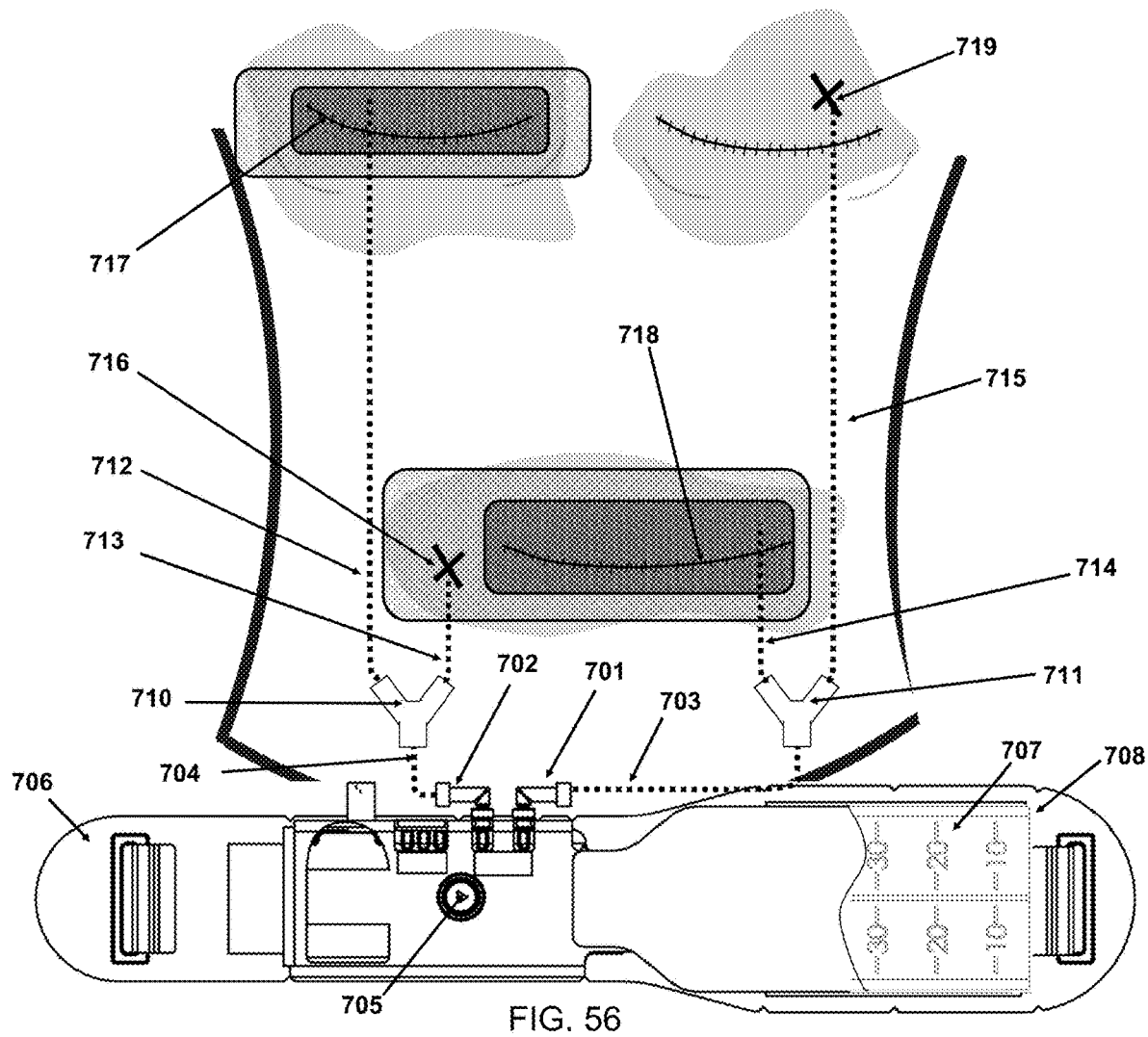
FIG. 56 is a view of a complete belt/peristaltic pump device with two separate adapters as in FIG. 54 allowing for multiple fluid removal lines leading to a patient's surface mastectomy wound, a deep wound on the other breast, and an abdominal surface and deep wound simultaneously.
Figure 59:
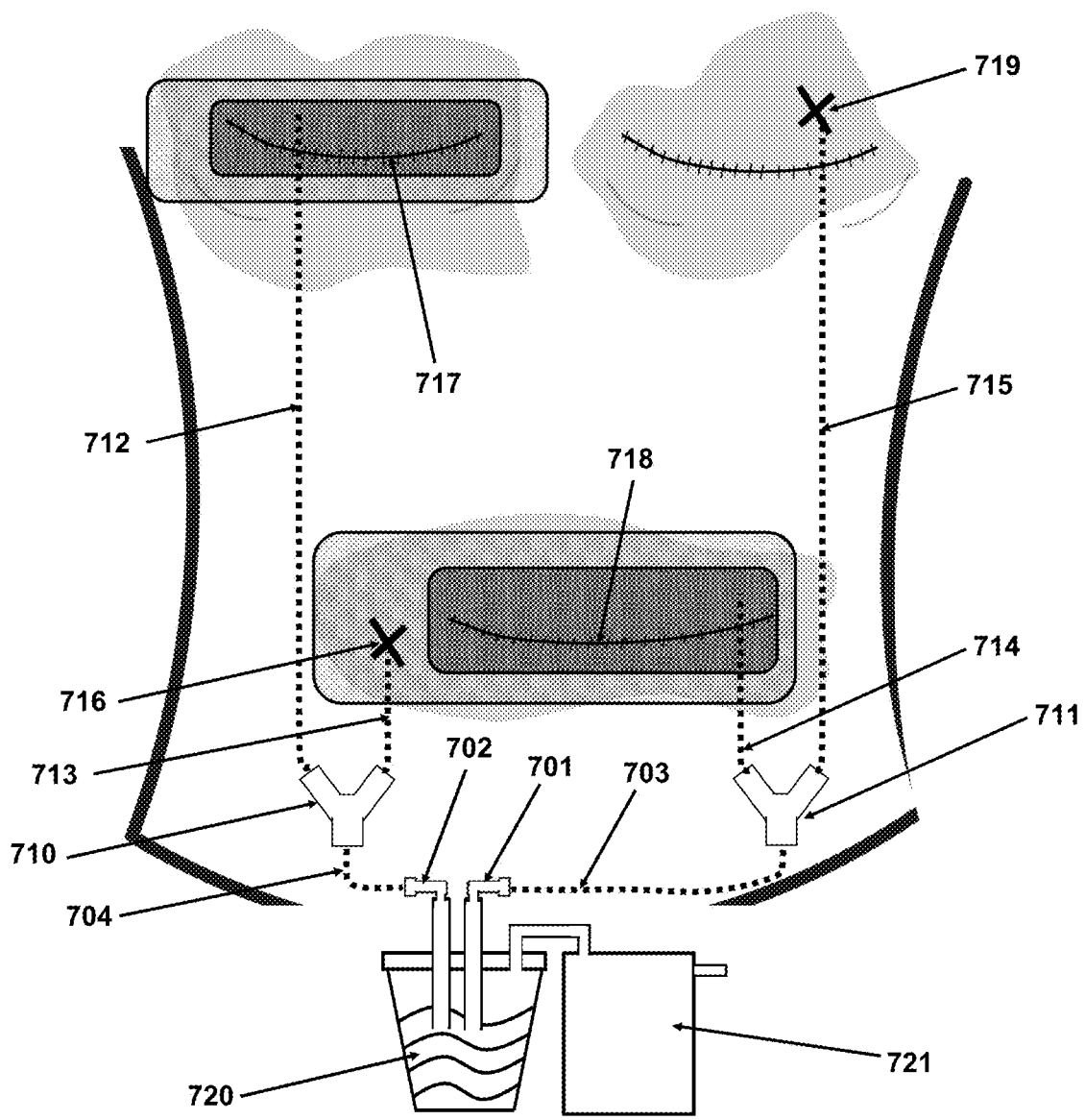
FIG. 59 is a view of a complete belt/air pump device with two separate adapters as in FIG. 54 allowing for multiple fluid removal lines leading to a patient's surface mastectomy wound, a deep wound on the other breast, and an abdominal surface and deep wound simultaneously.
Figure 60:
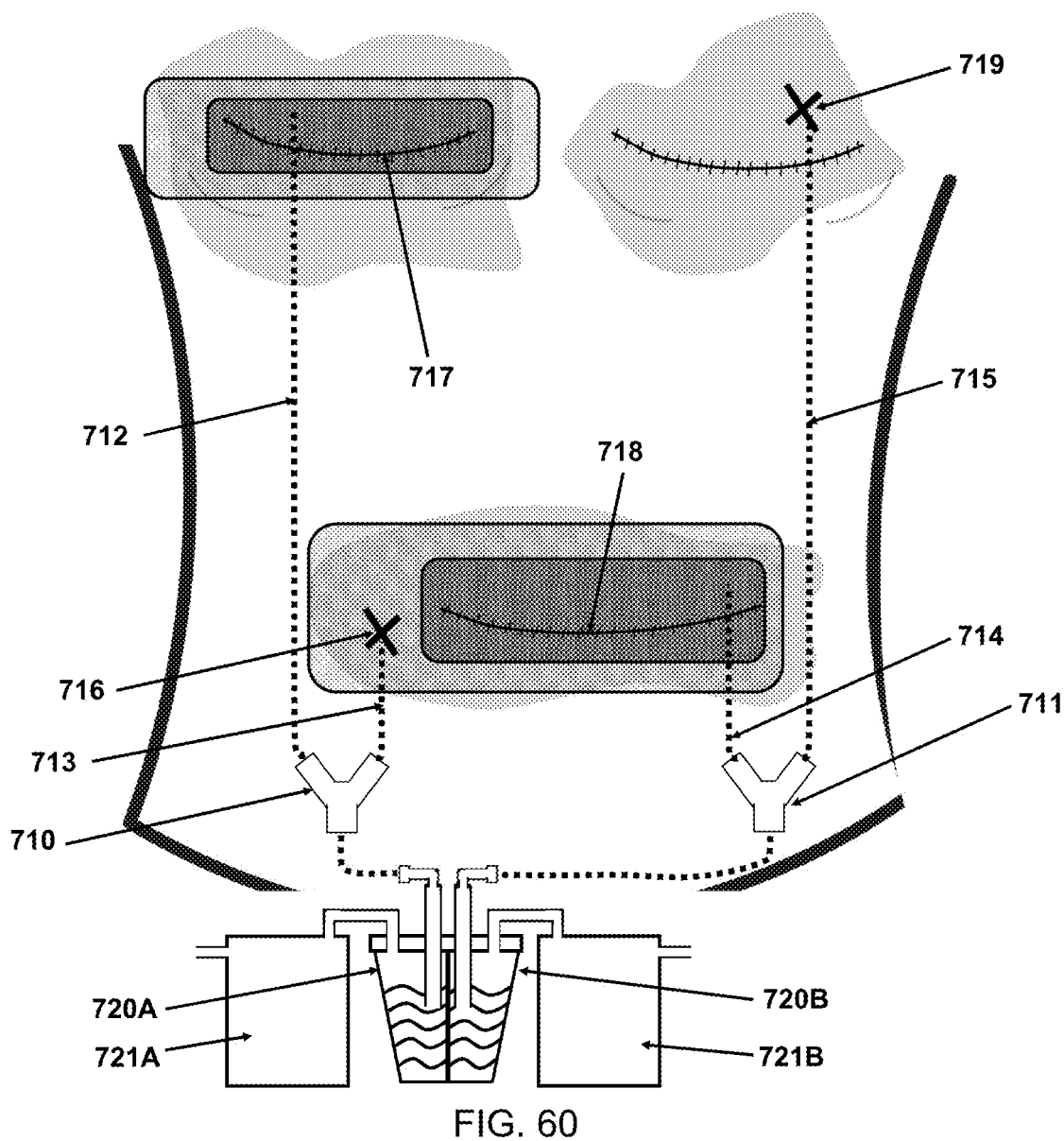
FIG. 60 is a view of a complete belt/double air pump device with two separate adapters as in FIG. 54 allowing for multiple fluid removal lines leading to a patient's surface mastectomy wound, a deep wound on the other breast, and an abdominal surface and deep wound simultaneously.

FIGS. 56, 59 and 60 show the utilization of a single type of pump with simultaneous drainage of four different wounds on a mastectomy/abdominal surgery patient. FIG. 56 shows a peristaltic pump device 705 with a collection component 706 having gradations 707 for fluid measurement purposes and two separate ports 701, 702 leading to two separate fluid removal/transfer lines 703, 704. One line 703 leads to a diverter 711 that leads to one further transfer line 714 that leads to an abdominal surface wound 718, and a further second line 715 leads to a mastectomy wound 719 (both on the right side of the patient's torso). The other line 704 leads to a second diverter 710 that leads to one further transfer line 712 that leads to a mastectomy surface wound 717 and the other further transfer line 713 leads to an abdominal internal wound 712 (both on the left facing side of the patient's torso). FIG. 59 is basically the same as FIG. 56, but the pump device 720 is a hydraulic vacuum with a collection tank 721. FIG. 60 shows two separated hydraulic pumps 720A, 720B, with two separate collection tanks 721A, 721B that accords the same simultaneous capabilities for fluid removal from the four different wounds of the subject mastectomy/abdominal surgery patient.

Figure 61:
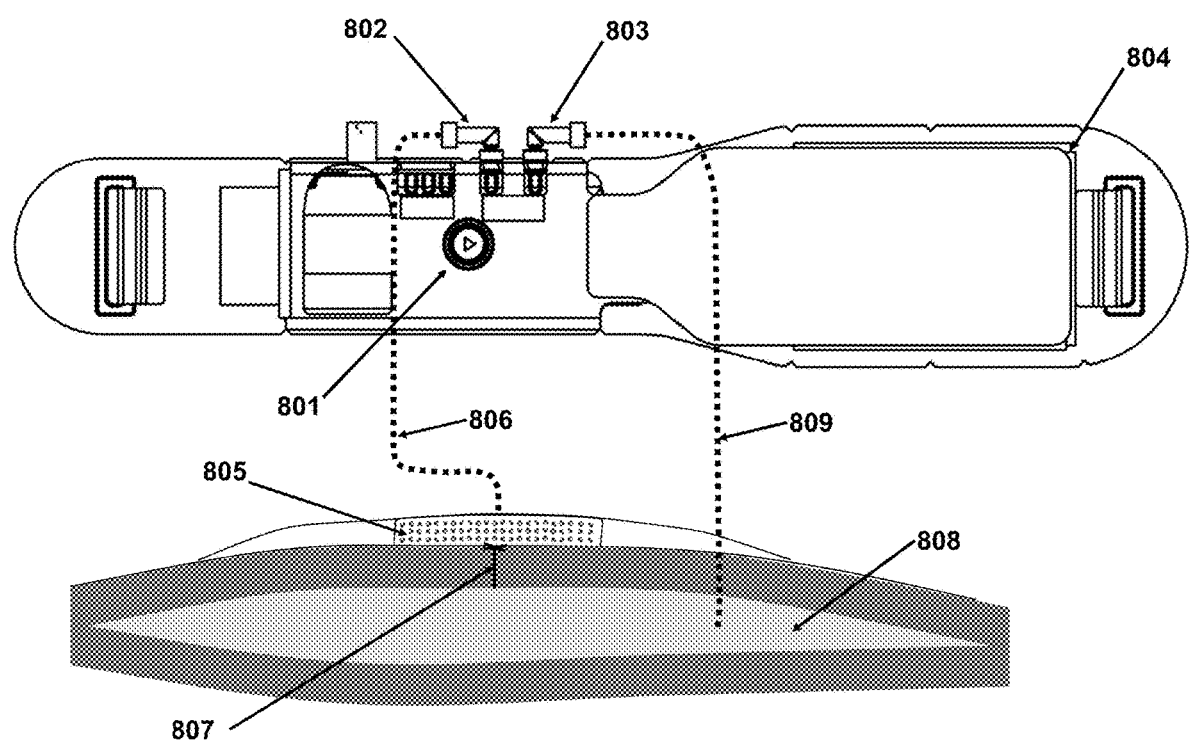
FIG. 61 is a side cross-sectional view of a complete belt/peristaltic pump device with fluid removal lines leading to a patient's surface wound and adjacent deep wound simultaneously.
Figure 62:
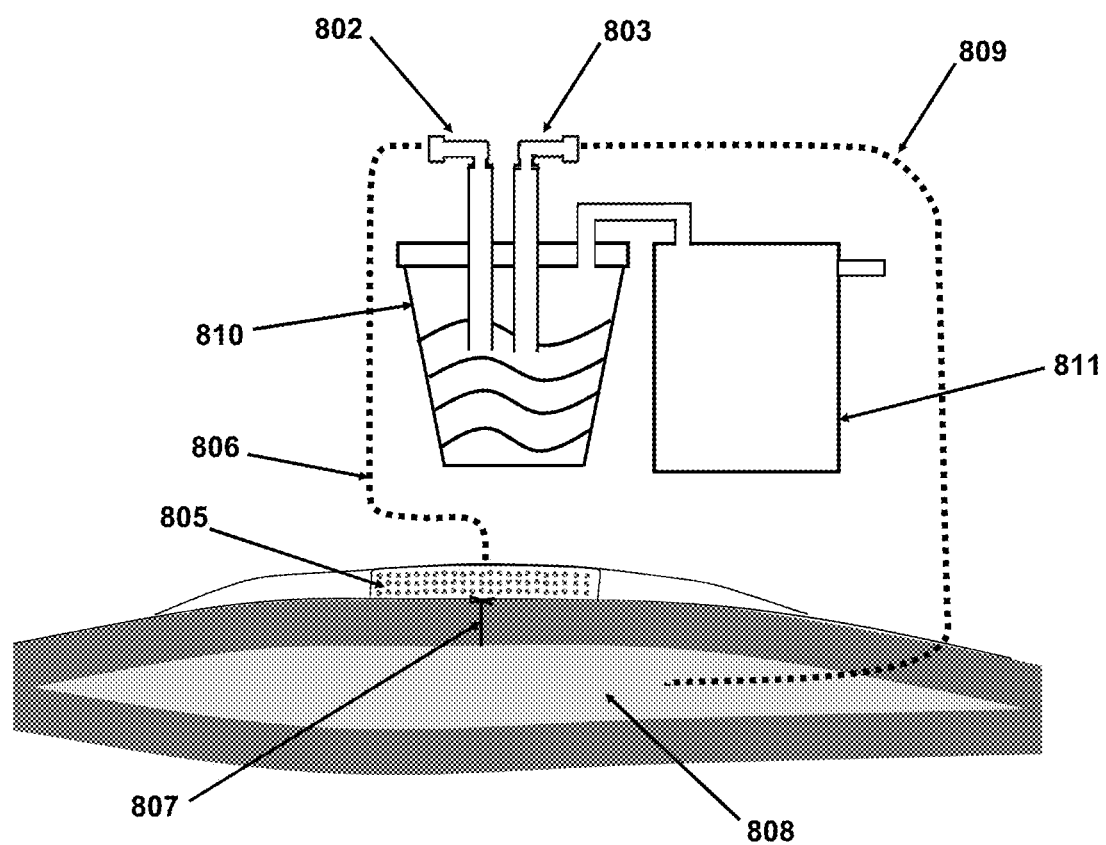
FIG. 62 is a side cross-sectional view of a complete belt/air pump device with fluid removal lines leading to a patient's surface wound and adjacent deep wound simultaneously.
Figure 63:
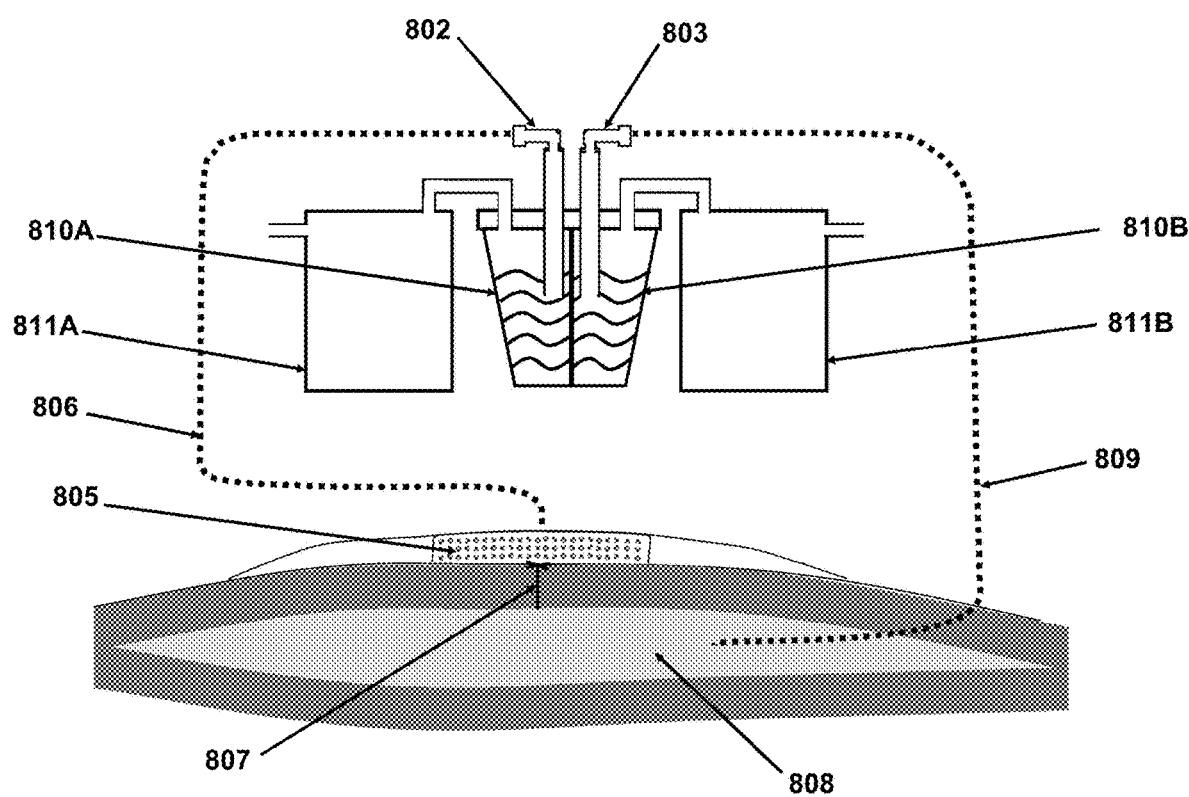
FIG. 63 is a side cross-sectional view of a complete belt/double air pump device with fluid removal lines leading to a patient's surface mastectomy wound and adjacent deep wound simultaneously.

FIGS. 61-63 show a side cross-sectional view of the utilization of a single type of pump with simultaneous drainage of two different wounds on a subject patient, in this situation with one wound a surface type and a second wound internal thereto adjacent to such a surface wound. FIG. 61 shows a peristaltic pump device 801 with a collection component 804 and two separate ports 802, 803 leading to two separate fluid removal/transfer lines 806, 809 for such a purpose. One line 806 leads to the aforementioned surface wound 805 having an incision below 807 and the other line 809 leads to the aforementioned internal wound 808. FIG. 62 is basically the same as FIG. 61, but the pump device 810 is a hydraulic vacuum with a collection tank 811. FIG. 63 shows two separated hydraulic pumps 810A, 810B, with two separate collection tanks 811A, 811B that accords the same simultaneous capabilities for fluid removal from the two adjacent wound sites of the subject patient.

Figure 64:
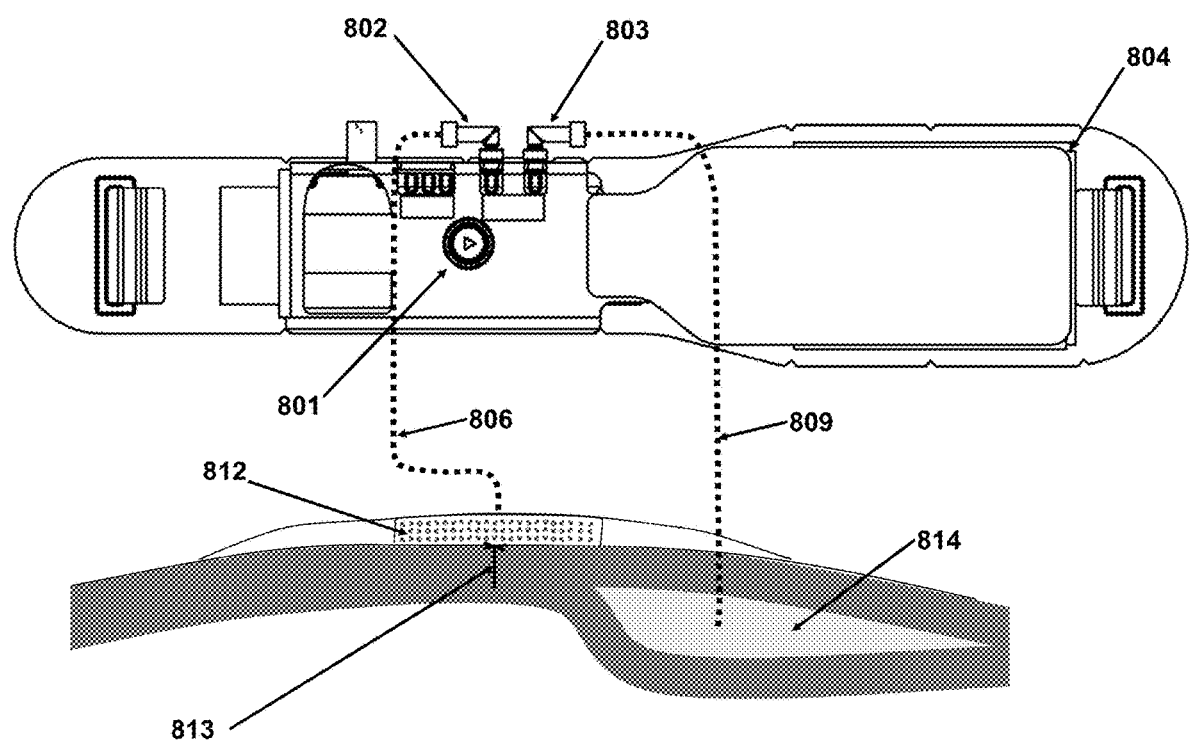
FIG. 64 is a side cross-sectional view of a complete belt/peristaltic pump device with fluid removal lines leading to a patient's surface wound and separate nearby deep wound simultaneously.
Figure 65:
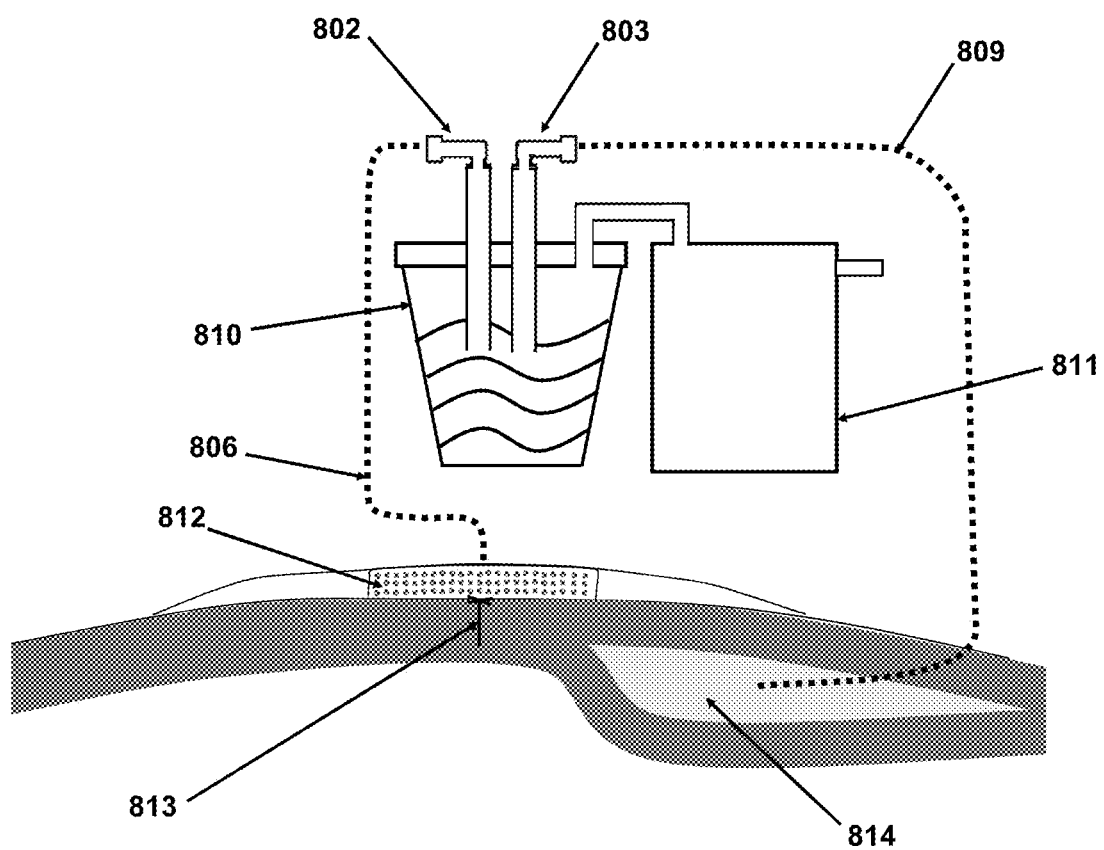
FIG. 65 is a side cross-sectional view of a complete belt/air pump device with fluid removal lines leading to a patient's surface wound and separate nearby deep wound simultaneously.
Figure 66:
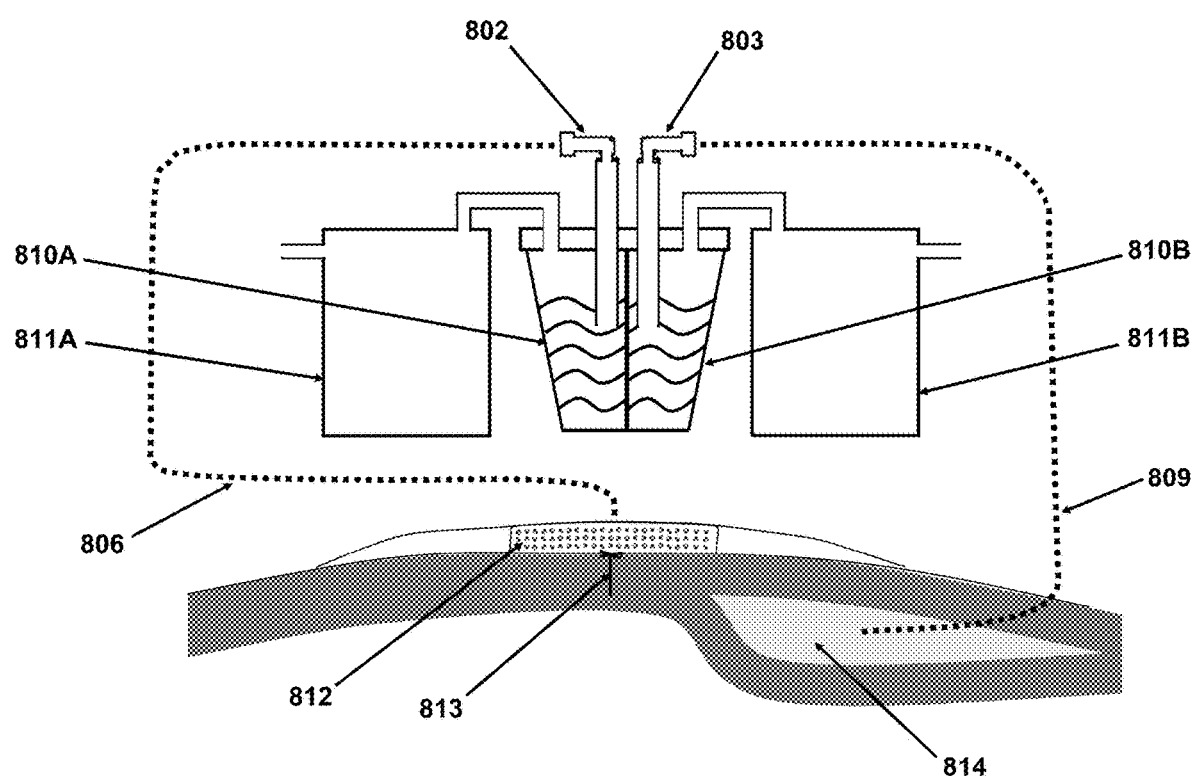
FIG. 66 is a side cross-sectional view of a complete belt/double air pump device with fluid removal lines leading to a patient's surface mastectomy wound and separate nearby deep wound simultaneously.

FIGS. 64-66 show a side cross-sectional view of the utilization of a single type of pump with simultaneous drainage of two different wounds on a subject patient, in this situation with one wound a surface type and a second wound internal thereto in a near, but distinct region of the subject patient. FIG. 64 shows a peristaltic pump device 801 with a collection component 804 and two separate ports 802, 803 leading to two separate fluid removal/transfer lines 806, 809 for such a purpose. One line 806 leads to the aforementioned surface wound 812 having an incision below 813 and the other line 809 leads to the aforementioned internal wound 814. FIG. 65 is basically the same as FIG. 64, but the pump device 810 is a hydraulic vacuum with a collection tank 811. FIG. 66 shows two separated hydraulic pumps 810A, 810B, with two separate collection tanks 811A, 811B that accords the same simultaneous capabilities for fluid removal from the two distinct wounds and sites thereof of the subject patient.

Figure 67:
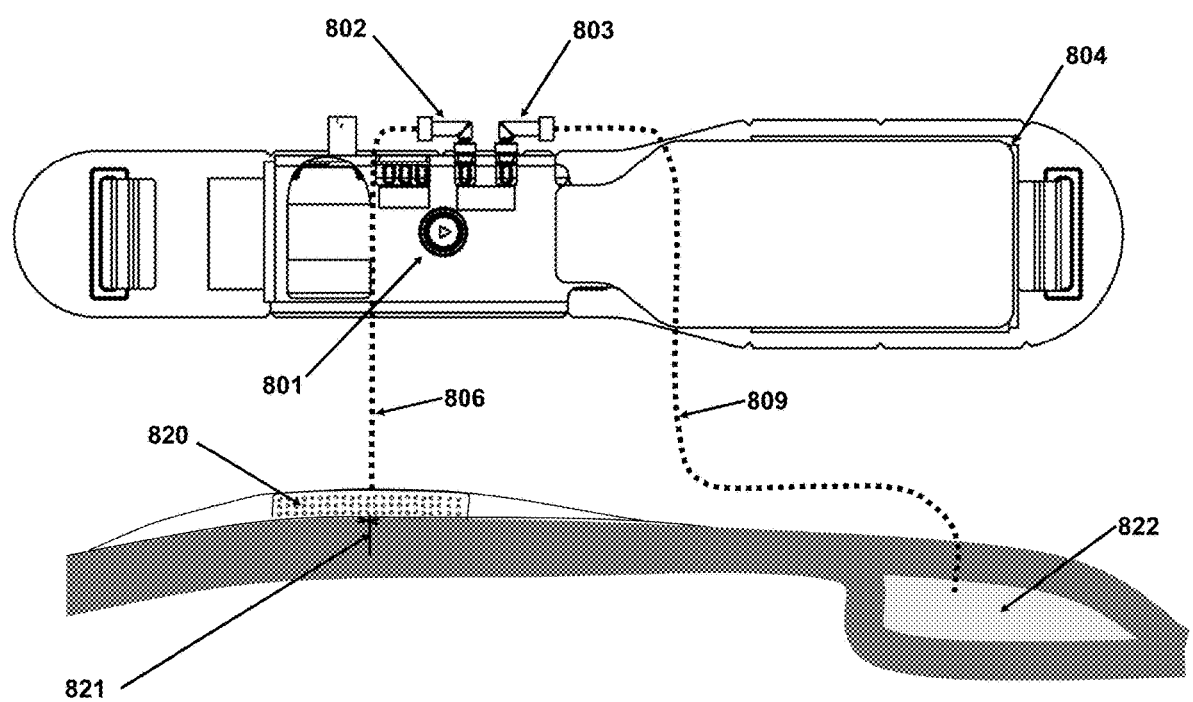
FIG. 67 is a side cross-sectional view of a complete belt/peristaltic pump device with fluid removal lines leading to a patient's surface wound and distant deep wound simultaneously.
Figure 68:
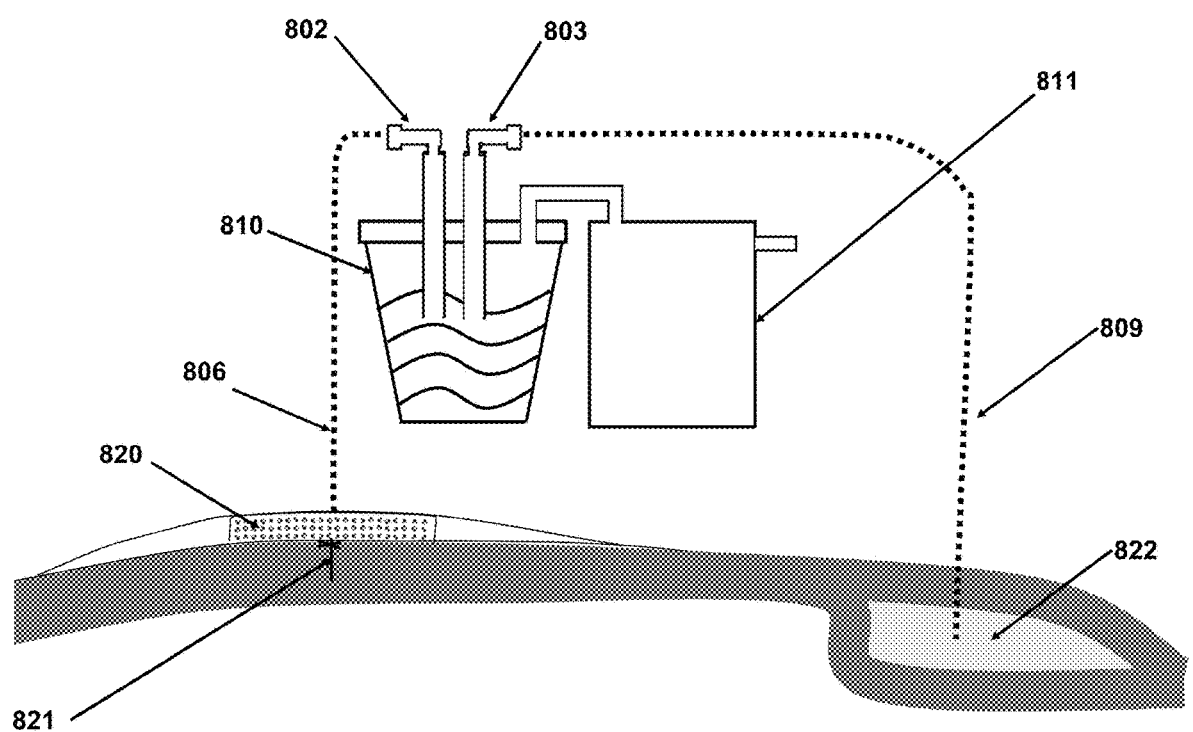
FIG. 68 is a side cross-sectional view of a complete belt/air pump device with fluid removal lines leading to a patient's surface wound and distant deep wound simultaneously.
Figure 69:
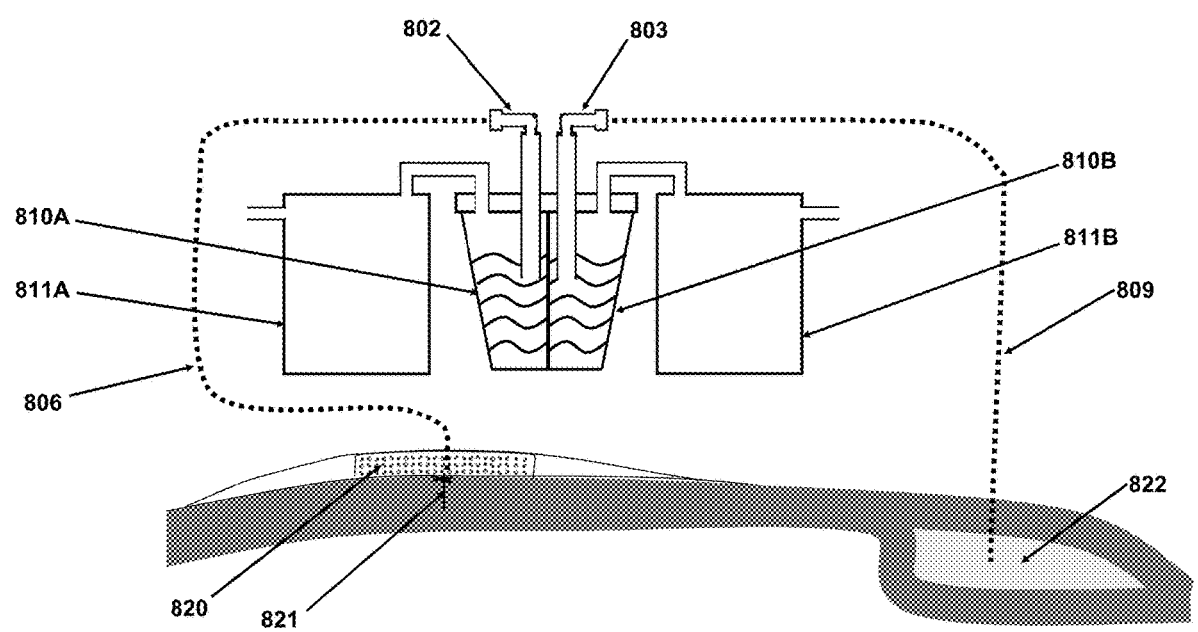
FIG. 69 is a side cross-sectional view of a complete belt/double air pump device with fluid removal lines leading to a patient's surface mastectomy wound and distant deep wound simultaneously.

FIGS. 67-69 show a side cross-sectional view of the utilization of a single type of pump with simultaneous drainage of two different wounds on a subject patient, in this situation with one wound a surface type and a second wound internal in a completely different and distinct region of the subject patient's body. FIG. 67 shows a peristaltic pump device 801 with a collection component 804 and two separate ports 802, 803 leading to two separate fluid removal/transfer lines 806, 809 for such a purpose. One line 806 leads to the aforementioned surface wound 820 having an incision below 821 and the other line 809 leads to the aforementioned internal wound 822. FIG. 68 is basically the same as FIG. 67, but the pump device 810 is a hydraulic vacuum with a collection tank 811. FIG. 69 shows two separated hydraulic pumps 810A, 810B, with two separate collection tanks 811A, 811B that accords the same simultaneous capabilities for fluid removal from the two different and distinct wounds and wound sites of the subject patient.

With these descriptions of the potential embodiments of the disclosure, it will be evident to the ordinarily skilled artisan that such a system and method described herein allows for effective fluid removal from all types and locations of wounds and wound sites on a subject patient utilizing a single pump device for such a purpose. This capability thus accords efficiencies and, for that matter, far less cumbersome, far more comfortable, far cleaner, and other far more reliable surgical/wound fluid removal than provided within the current state of the art. Whether in relation to the capabilities accorded the disclosed system and method as it pertains to actual drainage capacity for multiple wounds and wound sites with a single pump device, or the further ability to utilize a peristaltic pump device to provide more reliable trouble shooting as it concerns air leaks, clogs, and/or fluid removal completion, such a system and method has heretofore been unexplored within the medical industry.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A system for simultaneous collection of internal fluid from a plurality of wounds or incisions, said system comprising:
   a single device having:
   i) at least one pump unit comprising:
      a pump unit housing comprising:
         a first inlet port,
         a first outlet port,
         a first fluid pump in fluid communication with the first inlet port and the first outlet port,
         a second inlet port,
         a second outlet port, and
         a second fluid pump in fluid communication with the second inlet port and the second outlet port;
   ii) a first pressure sensor in communication with the first fluid pump and a second pressure sensor in communication with the second fluid pump;
   iii) a first drainage structure in fluid communication with the first fluid pump and the first inlet port and configured to collect fluid from deep wounds;
   iv) a first fluid reservoir in fluid communication with the first fluid pump via the first outlet so that the first fluid reservoir collects the fluid from the deep wounds;
   v) a second drainage structure in fluid communication with the second fluid pump and the second inlet port and configured to be introduced into and collect fluid from a surface wounds;
   vi) a second fluid reservoir in fluid communication with the second fluid pump via the second outlet port so that the second fluid reservoir collects the fluid from the surface wounds;
   wherein the at least one pump unit creates a continuous negative pressure between the first fluid pump and the first drainage structure to draw said fluid from the deep wounds through the first drainage structure into the first fluid pump through the first inlet port, and to create a positive pressure between the first fluid pump and the first fluid collector to transport the fluid from the first fluid pump to the first fluid collector through the first outlet port;
   wherein the first pressure sensor monitors the continuous negative pressure of the first fluid pump in a first pressure range;
   wherein the pump unit creates a continuous negative pressure between the second fluid pump and the second drainage structure to draw said fluid from the surface wounds through the second drainage structure into the second inlet port and to the second fluid collector through the second outlet port;
   wherein the second pressure sensor monitors the continuous negative pressure of the second fluid pump in a second pressure range that is different than the first pressure range; and
   wherein the system provides simultaneous fluid removal from the deep wounds and the surface wounds.

2. The system of claim 1, wherein the first fluid pump and the second fluid pump are selected from a peristaltic pump, a hydraulic pump, an air pump, and any combinations thereof.

3. The system of claim 1, further comprising the first and second drainage structures that include at least one diverter having a single port leading to the first or second drainage structures, and at least two ports attached to and leading from the other first or second drainage structure.

4. The system of claim 2, wherein the first fluid pump and the second fluid pump are peristaltic pumps.

5. The device of claim 1, wherein the first fluid reservoir and the second fluid reservoir are removably attached to said pump unit.

6. The system of claim 5, wherein the first fluid reservoir and the second fluid reservoir are disposable.

7. A method of simultaneous removal fluid from deep wounds and surface wounds from a single subject patient, said method comprising:
   i) providing the system of claim 1;
   ii) introducing the first drainage structure adjacent to the deep wounds and introducing the second drainage structure within the surface wounds, such that at least two different wounds or incisions are attached separately to the first drainage structure and the second drainage structure at the same time;
   iii) activating the first fluid pump and the second fluid pump, thereby initiating fluid removal from the deep wounds and the surface wounds respectively to which the first drainage structure and the second drainage structure are introduced; and
   iv) collecting said fluid from the deep wounds or the surface wounds respectively to which at least one of the first or second drainage structure is introduced.

8. A method of simultaneous removal fluid from deep wounds and surface wounds from a single subject patient, said method comprising:
   i) providing the system of claim 2;
   ii) introducing the first drainage structure adjacent to the deep wounds and introducing the second drainage structure within the surface wounds, such that at least two different wounds or incisions are attached separately to the first drainage structure and the second drainage structure at the same time;
   iii) activating the first fluid pump and the second fluid pump, thereby initiating fluid removal from the deep wounds and the surface wounds respectively to which the first drainage structure and the second drainage structure are introduced; and iv) collecting said fluid from the deep wounds or the surface wounds respectively to which at least one of the first or second drainage structure is introduced.

9. A method of simultaneous removal fluid from deep wounds and surface wounds from a single subject patient, said method comprising:

i) providing the system of claim 3;

ii) introducing the first drainage structure adjacent to the deep wounds and introducing the second drainage structure within the surface wounds, such that at least two different wounds or incisions are attached separately to the first drainage structure and the second drainage structure at the same time;

iii) activating the first fluid pump and the second fluid pump, thereby initiating fluid removal from the deep wounds and the surface wounds respectively to which the first drainage structure and the second drainage structure are introduced; and iv) collecting said fluid from the deep wounds or the surface wounds respectively to which at least one of the first or second drainage structure is introduced.

10. The system of claim 1, further comprising a first one-way valve in communication with the first inlet port to prevent backflow of the internal fluid back into the deep wounds, and a second one-way valve in communication with the second inlet port to prevent backflow of the internal fluid back into the surface wounds.

11. The method of claim 7, further comprising a step of preventing back flow of the internal fluid back into the deep wounds, and a step of preventing back flow of the internal fluid back into the surface wounds.

12. The system of claim 1, wherein the deep wounds are two deep wounds and the first fluid pump removes fluid from both of the two deep wounds.

13. The system of claim 12, further comprising a splitter device in communication with two of the first drain structures that are in communication the two deep wounds.

14. The system of claim 1, further comprising an abdominal binder that is configured to extend around an abdominal region of a user to connect the system to the user, wherein the at least one pump unit, the first fluid reservoir, and the second fluid reservoir are connected to the abdominal binder; and wherein the at least one pump unit and the first fluid reservoir and the second fluid reservoir are coplanar and extend circumferentially around the abdominal region of the user so that the at least one pump and the first fluid reservoir and the second fluid reservoir follow a direction of the abdominal binder.

15. The system of claim 10, further comprising an abdominal binder that is configured to extend around an abdominal region of a user to connect the system to the user, wherein the at least one pump unit, the first fluid reservoir, and the second fluid reservoir are connected to the abdominal binder;

wherein the at least one pump unit is in communication with the first fluid reservoir via the first one-way valve and the at least one pump unit is in communication with the second fluid reservoir via the second one-way valve; and wherein the at least one pump unit comprises a length and the first fluid reservoir and the second fluid reservoir each include a length, wherein the first fluid reservoir and the second fluid reservoir each include an inlet that points in a direction of the length of the first fluid reservoir, the length of the second fluid reservoir, and the length of the at least one pump unit so that the at least one pump unit and the first fluid reservoir and the second fluid reservoir are coplanar and extend circumferentially around the abdominal region of the user, wherein the length of the at least one pump unit extends in a direction circumferentially around the abdominal region of the user.

16. The system of claim 14, further comprising sensors in communication with the first drainage structures and the second drainage structures;

wherein some of the sensors are movable with the first drainage structure so that some of the sensors are movable into communication with the deep wounds and some of the sensors are movable with the second drain structures into communication with the surface wounds.

17. The system of claim 16, wherein the sensors are located within the first drainage structures or the second drainage structures.

18. The method of claim 7, further comprising sensors in the first drainage structures and the second drainage structures;

wherein the method includes a step of detecting with the sensors if the first drainage structures and the second drainage structures are vacuum locked, clogged, all of the fluid is removed, or a combination thereof; and wherein the method includes a step of placing the first drainage structure into a deep would along with some of the sensors.

19. The method of claim 18, further comprising a step of reversing the fluid pump if a clog is detected.

20. The system of claim 1, wherein the first pressure range is in a range of 200 mmHg to 700 mmHg below ambient pressure.

* * * * *